US007494788B2

(12) United States Patent
Dunker et al.

(10) Patent No.: US 7,494,788 B2
(45) Date of Patent: Feb. 24, 2009

(54) ENTROPIC BRISTLE DOMAIN SEQUENCES AND THEIR USE IN RECOMBINANT PROTEIN PRODUCTION

(75) Inventors: A. Keith Dunker, Indianapolis, IN (US); Vladimir N. Uversky, Carmel, IN (US); Marc S. Cortese, Indianapolis, IN (US); James Mueller, Indianapolis, IN (US)

(73) Assignee: Molecular Kinetics, Inc., Indianapolis, IN (US)

( * ) Notice: Subject to any disclaimer, the term of this patent is extended or adjusted under 35 U.S.C. 154(b) by 0 days.

(21) Appl. No.: 11/485,613

(22) Filed: Jul. 11, 2006

(65) Prior Publication Data

US 2007/0105195 A1 May 10, 2007

Related U.S. Application Data

(60) Provisional application No. 60/698,456, filed on Jul. 11, 2005.

(51) Int. Cl.
*C07K 14/00* (2006.01)
*C12P 21/04* (2006.01)
*C12N 15/62* (2006.01)
*C12N 5/02* (2006.01)
*C07K 19/00* (2006.01)

(52) U.S. Cl. ............... 435/69.7; 435/69.1; 435/320.1; 435/325; 536/23.4

(58) Field of Classification Search ............ None
See application file for complete search history.

(56) References Cited

U.S. PATENT DOCUMENTS

| 4,237,224 | A | 12/1980 | Cohen et al. ............... 435/68 |
| 4,683,195 | A | 7/1987 | Mullis et al. ............... 435/6 |
| 4,683,202 | A | 7/1987 | Mullis ....................... 435/91 |
| 4,751,180 | A | 6/1988 | Cousens et al. ............ 435/68 |
| 4,800,159 | A | 1/1989 | Mullis et al. ............ 435/172.3 |
| 4,883,750 | A | 11/1989 | Whiteley et al. ............ 435/6 |
| 4,935,233 | A | 6/1990 | Bell et al. ................ 424/85.5 |
| 5,837,458 | A | 11/1998 | Minshull et al. ............ 435/6 |

FOREIGN PATENT DOCUMENTS

| EP | 0320308 | A2 | 6/1989 |
| EP | 0329822 | A2 | 8/1989 |
| EP | 0519596 | B1 | 2/2005 |
| GB | 2202328 | A | 9/1988 |
| WO | 87/06270 | A1 | 10/1987 |
| WO | 88/10315 | A1 | 12/1988 |
| WO | 89/06700 | A1 | 7/1989 |
| WO | 89/09284 | A1 | 10/1989 |

OTHER PUBLICATIONS

Harris et al., Journal of Neuroscience Research, 30:47-62 (1991).*
Hoh, Proteins: Structure, Function and Genetics, 32: 223-228 (1998).*
Brown and Hoh, Biochemistry 36(49): 15035-15040 (1997).*
Abrahmsén et al., "Secretion of heterologous gene products to the culture medium of *Escherichia coli*," *Nucleic Acids Research* 14(18):7487-7500, 1986.
Altschul et al., "Basic local alignment search tool," *Journal of Molecular Biology* 215:403-410, 1990.
Altschul et al., "Gapped BLAST and PSI-BLAST: a new generation of protein database search programs," *Nucleic Acids Research* 25(17):3389-3402, 1997.
Bach et al., "*Escherichia coli* maltose-binding protein as a molecular chaperone for recombinant intracellular cytoplasmic single-chain antibodies," *Journal of Molecular Biology* 312:79-93, 2001.
Bitter et al., "Expression and secretion vectors for yeast," in Abelson and Simon (eds.), *Methods in Enzymology 153*, Academic Press, Inc., San Diego, California, 1987, pp. 516-544.
Braun et al., "Proteome-scale purification of human proteins from bacteria," *Proceedings of the National Academy of Sciences* 99(5):2654-2659, Mar. 5, 2002.
Broglie et al., "Light-regulated expression of a pea ribulose-1,5-bisphosphate carboxylase small subunit gene in transformed plant cells," *Science* 224:838-843, May 25, 1984.
Brown et al., "Tumor-specific genetically engineered murine/human chimeric monoclonal antibody," *Cancer Research* 47:3577-3583, Jul. 1, 1987.
Christendat et al., "Structural proteomics of an archaeon," *Nature Structural Biology* 7(10):903-909, Oct. 2000.
Christendat et al., "Structural proteomics: prospects for high throughput sample preparation," *Progress in Biophysics and Molecular Biology* 73:339-345, 2000.
Colbère-Garapin et al., "A new dominant hybrid selective marker for higher eukaryotic cells," *Journal of Molecular Biology* 150:1-14, 1981.
Coruzzi et al., "Tissue-specific and light-regulated expression of a pea nuclear gene encoding the small subunit of ribulose-1,5-bisphosphate carboxylase," *The EMBO Journal* 3(8):1671-1679, 1984.
Dayhoff et al., "A model of evolutionary change in proteins," *Atlas of Protein Sequence and Structure* 5(3):345-352, 1978.
Denning et al., "The *Saccharomyces cerevisiae* Nucleoporin Nup2p is a natively unfolded protein," *Journal of Biological Chemistry* 277(36):33447-33455, Sep. 6, 2002.
Dyson et al., "Production of soluble mammalian proteins in *Escherichia coli*: identification of protein features that correlate with successful expression," *BMC Biotechnology* 4:32, Dec. 14, 2004.
Engelhard et al., "The insect tracheal system: A conduit for the systemic spread of *Autographa californica* M nuclear polyhedrosis virus," *Proceedings of the National Academy of Sciences* 91:3224-3227, Apr. 1994.
Fox et al., "Maltodextrin-binding proteins from diverse bacteria and archaea are potent solubility enhancers," *FEBS Letters* 537:53-57, 2003.
GenBank Accession No. AF091342, Bos taurus neurofilament-M subunit (NF-M) mRNA, partial cds, Sep. 20, 1998.

(Continued)

*Primary Examiner*—John D Ulm
*Assistant Examiner*—Stacey MacFarlane
(74) *Attorney, Agent, or Firm*—Seed IP Law Group PLLC

(57) ABSTRACT

Compositions and methods for recombinant protein production and, more particularly, fusion polypeptides, polynucleotides encoding fusion polypeptides, expression vectors, kits, and related methods for recombinant protein production, are provided.

9 Claims, No Drawings

OTHER PUBLICATIONS

GenBank Accession No. BC073969, *Homo sapiens* neurofilament, heavy polypeptide 200kDa, mRNA (cDNA clone MGC:90283 Image:6137962), complete cds, Jun. 30, 2004.

GenBank Accession No. U08210, *Mus musculus* tropoelastin mRNA, complete cds, Oct. 31, 1995.

GenBank Accession No. V00604, Phage M13 genome, Nov. 14, 2006.

GenBank Accession No. X05558, Chicken mRNA for middle-molecular weight neurofilament fragment (NF-M), Apr. 18, 2005.

GenBank Accession No. X05640, Mouse NF-M gene for middle-molecular-mass neurofilament protein, Nov. 14, 2006.

GenBank Accession No. X69964, *S. cerevisiae* genes for nucleoporin and tRNAglu3, Mar. 26, 1993.

GenBank Accession No. Y00067, Human gene for neurofilament subunit M (NF-M), Nov. 14, 2006.

GenBank Accession No. Z12152, *R. norvegicus* mRNA for neurofilament protein middle (NF-M), Apr. 18, 2005.

GenBank Accession No. Z47378, *O.cuniculus* mRNA for neurofilament protein M., Apr. 18, 2005.

GenBank Acession No. M35131, Mouse neurofilament component (NF-H) mRNA, complete cds, Apr. 27, 1993.

Gottesman and Zipser, "Deg phenotype of *Escherichia coli lon* mutants," *Journal of Bacteriology* 133(2):844-851, Feb. 1978.

Hammarström et al., "Rapid screening for improved solubility of small human proteins produced as fusion in *Escherichia coli*," *Protein Science* 11:313-321, 2002.

Hartman and Mulligan, "Two dominant-acting selectable markers for gene transfer studies in mammalian cells," *Proceedings of the National Academy of Sciences* 85:8047-8051, Nov. 1988.

Hein, "Unified Approach to Alignment and Phylogenies," in Abelson and Simon (eds.), *Methods in Enzymology 183*, Academic Press, Inc., San Diego, California, 1990, pp. 626-645.

Higgins and Sharp, "Fast and sensitive multiple sequence alignments on a microcomputer," *CABIOS Communications* 5(2):151-153, 1989.

Hobbs or Murry, "Genetic Engineering," *McGraw Hill Yearbook of Science and Technology* McGraw Hill, New York, 1992, pp. 191-196.

Hoh, "Functional protein domains from the thermally driven motion of polypeptide chains: A proposal," *Proteins: Structure, Function, and Genetics* 32(2):223-228, 1998.

Itakura et al., "Expression in *Escherichia coli* of a chemically synthesized gene for the hormone somatostatin," *Science* 198:1056-1063, Dec. 9, 1977.

Jones et al., "Replacing the complementarity-determining regions in a human antibody with those from a mouse," *Nature* 321:522-525, May 29, 1986.

Kapust and Waugh, "*Escherichia coli* maltose-binding protein is uncommonly effective at promoting the solubility of polypeptides to which it is fused," *Protein Science* 8:1668-1674, 1999.

Köhler and Milstein, "Derivation of specific anitbody-producing tissue culture and tumor lines by cell fusion," *European Journal of Immunology* 6:511-519, 1976.

Kroll et al., "A multifunctional prokaryotic protein expression system: Overproduction, affinity purification, and selective detection," *DNA and Cell Biology* 12(5):441-453, 1993.

Kuhn et al., "Crystal structure of Thy1, a thymidylate synthase complementing protein from *Thermotoga maritima* at 2.25 Å Resolution," *Proteins: Structure, Function and Genetics* 49:142-145, 2002.

LoBuglio et al., "Mouse/human chimeric monoclonal antibody in man: Kinetics and immune response," *Proceedings of the National Academy of Sciences* 86:4220-4224, Jun. 1989.

Logan and Shenk, "Adenovirus tripartite leader sequence enhances translation of mRNAs late after infection," *Proceedings of the National Academy of Sciences* 81:3655-3659, Jun. 1984.

Lowy et al., "Isolation of transforming DNA: Cloning the hamster aprt gene," *Cell* 22:817-823, Dec. 1980.

Maddox et al., "Elevated serum levels in human pregnancy of a molecule immunochemically similar to eosinophil granule major basic protein," *Journal of Experimental Medicine* 158:1211-1226, Oct. 1, 1983.

Maratea et al., "Deletion and fusion analysis of the phage øX174 lysis gene E," *Gene* 40:39-46, 1985.

Merrifield, "Solid phase peptide synthesis. I. The Synthesis of a tetrapeptide," *Journal of the American Chemical Society* 85(14):2149-2154, Jul. 20, 1963.

Miller, "Appendix I. Formulas and Recipes," in *Experiments in Molecular Genetics*, Cold Spring Harbor Laboratory, New York, 1972, pp. 431-433.

Milner, "Polymer Brushes," *Science* 251:905-914, Feb. 22, 1991.

Murphy et al., "Genetic construction, expression, and melanoma-selective cytotoxicity of a diphtheria toxin-related α-melanocyte-stimulating hormone fusion protein," *Proceedings of the National Academy of Sciences* 83:8258-8262, Nov. 1986.

Myers and Miller, "Optimal alignments in linear space," *CABIOS* 4(1):11-17, 1988.

Nakielny and Dreyfuss, "Transport of proteins and RNAs in and out of the nucleus," *Cell* 99:677-690, Dec. 23, 1999.

Napper, "Stabilization by attached polymer: steric stabilization," in Ottewill and Rowell (eds.) *Polymeric Stabilization of Colloidal Dispersions*, Academic Press, New York, 1983, pp. 18-30.

Needleman and Wunsch, "A general method applicable to the search for similarities in the amino acid sequence of two proteins," *Journal of Molecular Biology* 48:443-453, 1970.

Nilsson et al., "Immobilization and purification of enzymes with staphylococcal protein A gene fusion vectors," *The EMBO Journal* 4(4):1075-1080, 1985.

Pearson and Lipman, "Improved tools for biological sequence comparison," *Proceedings of the National Academy of Sciences* 85:2444-2448, Apr. 1988.

Pemberton et al., "Transport routes through the nuclear pore complex," *Current Opinion in Cell Biology* 10:392-399, 1998.

Porath, "Immobilized metal ion affinity chromatography," *Protein Expression and Purification* 3:263-281, 1992.

Rhodes et al., "Transformation of maize by electroporation of embryos," in Nickoloff (ed.), *Methods in Molecular Biology 55*, Humana Press, Inc., Totowa, New Jersey, 1995, pp. 121-131.

Richarme and Caldas, "Chaperone properties of the bacterial periplasmic substrate-binding proteins," *Journal of Biological Chemistry* 272(25):15607-15612, Jun. 20, 1997.

Riechmann et al., "Reshaping human antibodies for therapy," *Nature* 332:323-327, Mar. 1988.

Robinson, "Comparison of Labeled Trees with Valency Three," *Journal of Combinatorial Theory B* 11(2):105-119, 1971.

Rout et al., "The yeast nuclear pore complex: Composition, architecture, and transport mechanism," *Journal of Cell Biology* 148(4):635-651, Feb. 21, 2000.

Rout and Aitchison, "The nuclear pore complex as a transport machine," *Journal of Biological Chemistry* 276(20):16593-16596, May 18, 2001.

Sachdev and Chirgwin, "Fusions to maltose-binding protein: Control of folding and solubility in protein purification," in Abelson and Simon (eds.), *Methods in Enzymology 326 Part A*, Academic Press, San Diego, California, 2000, pp. 312-321.

Saitou and Nei, "The neighbor-joining method: A new method for reconstructing phylogenetic trees," *Molecular Biology and Evolution* 4(4):406-425, 1987.

Scharf et al., "Heat stress promoters and transcription factors," *Results and Problems in Cell Differentiation* 20:125-162, 1994.

Shaw et al., "Characterization of a mouse/human chimeric monoclonal antibody (17-1A) to a colon cancer tumor-associated antigen," *Journal of Immunology* 138(12):4534-4538, Jun. 15, 1987.

Shen, "Multiple joined genes prevent product degradation in *Escherichia coli*," *Proceedings of the National Academy Sciences* 81:4627-4631, Aug. 1984.

Smith and Waterman, "Comparison of Biosequences," *Advances in Applied Mathematics* 2(4):482-489, Dec. 1981.

Smith, "Generating fusions to glutathione S-transferase for protein studies," in Abelson and Simon (eds.), *Methods in Enzymology 326 Part A*, Academic Press, San Diego, California, 2000, pp. 254-270.

Swiss-Prot Accession No. P12839, Neurofilament medium polypeptide, Oct. 1, 1989.

Swiss-Prot Accession No. P54938, Neurofilament medium polypeptide [Fragment], Oct. 1, 1996.

Swiss-Prot Accession No. P08553, Neurofilament medium polypeptide, Aug. 1, 1988.

Swiss-Prot Accession No. P32499, Nucleoporin NUP2, Oct. 1, 1993.

Swiss-Prot Accession No. O77788, Neurofilament medium polypeptide, Apr. 27, 2001.

Swiss-Prot Accession No. P07197, Neurofilament medium polypeptide, Apr. 1, 1988.

Swiss-Prot Accession No. P12036, Neurofilament heavy polypeptide, Oct. 1, 1989.

Swiss-Prot Accession No. P16053, Neurofilament medium polypeptide, Apr. 1, 1990.

Swiss-Prot Accession No. P19246, Neurofilament heavy polypeptide, Nov. 1, 1990.

Swiss-Prot Accession No. P54320, Elastin [Precursor], Oct. 1, 1996.

Swiss-Prot Accession No. P69168, Coat protein A [Precursor], Jul. 21, 1986.

Takamatsu et al., "Expression of bacterial chloramphenicol acetyltransferase gene in tobacco plants mediated by TMV-RNA," *The EMBO Journal* 6(2):307-311, 1987.

Vaillancourt et al., "Recovery of polypeptides cleaved from purified calmodulin-binding peptide fusion proteins," *Biotechniques* 22(3):451-453, Mar. 1997.

Van Heeke and Schuster, "Expression of human asparagine synthetase in *Escherichia coli*," *Journal of Biological Chemistry* 264(10):5503-5509, Apr. 5, 1989.

Verhoeyen et al., "Reshaping human antibodies: grafting an antilysozyme activity," *Science* 239:1534-1536, Mar. 25, 1988.

Wigler et al., "Transfer of purified herpes virus thymidine kinase gene to cultured mouse cells," *Cell* 11:223-232, May 1977.

Wigler et al., "Transformation of mammalian cells with an amplifiable dominant-acting gene," *Proceedings of the National Academy of Sciences* 77(6):3567-3570, Jun. 1980.

Wilbur and Lipman, "Rapid similarity searches of nucleic acid and protein data banks," *Proceedings of the National Academy Sciences* 80:726-730, Feb. 1983.

Winter and Milstein, "Man-made antibodies," *Nature* 349:293-299, Jan. 24, 1991.

Winter and Sinibaldi, "The expression of heat shock protein and cognate genes during plant development," *Results and Problems in Cell Differentiation* 17:86-105, 1991.

Yang et al., "Three-dimensional architecture of the isolated yeast nuclear pore complex: Functionional and evolutionary implications," *Molecular Cell* 1:223-234, Jan. 1998.

Zhan et al., "Structural analysis of regulatory protein domains using GST-fusion proteins," *Gene* 281:1-9, 2001.

\* cited by examiner

SEQUENCE LISTING

<160> NUMBER OF SEQ ID NOS: 144

<210> SEQ ID NO 1
<211> LENGTH: 1026
<212> TYPE: PRT
<213> ORGANISM: Homo sapiens

<400> SEQUENCE: 1

```
Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
```

-continued

```
                115                 120                 125
Ala Ala Ala Leu Arg Gln Gln Ala Gly Arg Ser Ala Met Gly Glu
            130                 135                 140
Leu Tyr Glu Arg Glu Val Arg Glu Met Arg Gly Ala Val Leu Arg Leu
145                 150                 155                 160
Gly Ala Ala Arg Gly Gln Leu Arg Leu Glu Gln Glu His Leu Leu Glu
                165                 170                 175
Asp Ile Ala His Val Arg Gln Arg Leu Asp Asp Glu Ala Arg Gln Arg
                180                 185                 190
Glu Glu Ala Glu Ala Ala Arg Ala Leu Ala Arg Phe Ala Gln Glu
                195                 200                 205
Ala Glu Ala Ala Arg Val Asp Leu Gln Lys Lys Ala Gln Ala Leu Gln
            210                 215                 220
Glu Glu Cys Gly Tyr Leu Arg Arg His His Gln Glu Glu Val Gly Glu
225                 230                 235                 240
Leu Leu Gly Gln Ile Gln Gly Ser Gly Ala Ala Gln Ala Gln Met Gln
                245                 250                 255
Ala Glu Thr Arg Asp Ala Leu Lys Cys Asp Val Thr Ser Ala Leu Arg
            260                 265                 270
Glu Ile Arg Ala Gln Leu Glu Gly His Ala Val Gln Ser Thr Leu Gln
                275                 280                 285
Ser Glu Glu Trp Phe Arg Val Arg Leu Asp Arg Leu Ser Glu Ala Ala
            290                 295                 300
Lys Val Asn Thr Asp Ala Met Arg Ser Ala Gln Glu Glu Ile Thr Glu
305                 310                 315                 320
Tyr Arg Arg Gln Leu Gln Ala Arg Thr Thr Glu Leu Glu Ala Leu Lys
                325                 330                 335
Ser Thr Lys Asp Ser Leu Glu Arg Gln Arg Ser Glu Leu Glu Asp Arg
                340                 345                 350
His Gln Ala Asp Ile Ala Ser Tyr Gln Glu Ala Ile Gln Gln Leu Asp
            355                 360                 365
Ala Glu Leu Arg Asn Thr Lys Trp Glu Met Ala Ala Gln Leu Arg Glu
            370                 375                 380
Tyr Gln Asp Leu Leu Asn Val Lys Met Ala Leu Asp Ile Glu Ile Ala
385                 390                 395                 400
Ala Tyr Arg Lys Leu Leu Glu Gly Glu Glu Cys Arg Ile Gly Phe Gly
                405                 410                 415
Pro Ile Pro Phe Ser Leu Pro Glu Gly Leu Pro Lys Ile Pro Ser Val
                420                 425                 430
Ser Thr His Ile Lys Val Lys Ser Glu Glu Lys Ile Lys Val Val Glu
            435                 440                 445
Lys Ser Glu Lys Glu Thr Val Ile Val Glu Glu Gln Thr Glu Glu Thr
            450                 455                 460
Gln Val Thr Glu Glu Val Thr Glu Glu Glu Lys Glu Ala Lys Glu
465                 470                 475                 480
Glu Glu Gly Lys Glu Glu Glu Gly Gly Glu Glu Glu Ala Glu Gly
                485                 490                 495
Gly Glu Glu Glu Thr Lys Ser Pro Pro Ala Glu Glu Ala Ala Ser Pro
                500                 505                 510
Glu Lys Glu Ala Lys Ser Pro Val Lys Glu Glu Ala Lys Ser Pro Ala
            515                 520                 525
Glu Ala Lys Ser Pro Glu Lys Glu Glu Ala Lys Ser Pro Ala Glu Val
            530                 535                 540
```

```
Lys Ser Pro Glu Lys Ala Lys Ser Pro Ala Lys Glu Ala Lys Ser
545                 550                 555                 560

Pro Pro Glu Ala Lys Ser Pro Glu Lys Glu Ala Lys Ser Pro Ala
                565                 570                 575

Glu Val Lys Ser Pro Glu Lys Ala Lys Ser Pro Ala Lys Glu Ala
                580                 585                 590

Lys Ser Pro Ala Glu Ala Lys Ser Pro Glu Lys Ala Lys Ser Pro Val
            595                 600                 605

Lys Glu Glu Ala Lys Ser Pro Ala Glu Ala Lys Ser Pro Val Lys Glu
        610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Ala Lys Ser Pro Glu Lys Glu Ala Lys Ser Pro Glu Lys Ala
                660                 665                 670

Lys Ser Pro Val Lys Ala Glu Ala Lys Ser Pro Glu Lys Ala Lys Ser
            675                 680                 685

Pro Val Lys Ala Glu Ala Lys Ser Pro Glu Lys Ala Lys Ser Pro Val
    690                 695                 700

Lys Glu Glu Ala Lys Ser Pro Glu Lys Ala Lys Ser Pro Val Lys Glu
705                 710                 715                 720

Glu Ala Lys Ser Pro Glu Lys Ala Lys Ser Pro Val Lys Glu Glu Ala
                725                 730                 735

Lys Thr Pro Glu Lys Ala Lys Ser Pro Val Lys Glu Glu Ala Lys Ser
                740                 745                 750

Pro Glu Lys Ala Lys Ser Pro Glu Lys Ala Lys Thr Leu Asp Val Lys
            755                 760                 765

Ser Pro Glu Ala Lys Thr Pro Ala Lys Glu Glu Ala Arg Ser Pro Ala
    770                 775                 780

Asp Lys Phe Pro Glu Lys Ala Lys Ser Pro Val Lys Glu Glu Val Lys
785                 790                 795                 800

Ser Pro Glu Lys Ala Lys Ser Pro Leu Lys Glu Asp Ala Lys Ala Pro
                805                 810                 815

Glu Lys Glu Ile Pro Lys Glu Glu Val Lys Ser Pro Val Lys Glu
                820                 825                 830

Glu Glu Lys Pro Gln Glu Val Lys Val Lys Glu Pro Pro Lys Lys Ala
            835                 840                 845

Glu Glu Glu Lys Ala Pro Ala Thr Pro Lys Thr Glu Glu Lys Lys Asp
850                 855                 860

Ser Lys Lys Glu Glu Ala Pro Lys Lys Glu Ala Pro Lys Pro Lys Val
865                 870                 875                 880

Glu Glu Lys Lys Glu Pro Ala Val Glu Lys Pro Lys Glu Ser Lys Val
                885                 890                 895

Glu Ala Lys Lys Glu Glu Ala Glu Asp Lys Lys Val Pro Thr Pro
                900                 905                 910

Glu Lys Glu Ala Pro Ala Lys Val Glu Val Lys Glu Asp Ala Lys Pro
            915                 920                 925

Lys Glu Lys Thr Glu Val Ala Lys Lys Glu Pro Asp Asp Ala Lys Ala
            930                 935                 940

Lys Glu Pro Ser Lys Pro Ala Glu Lys Lys Glu Ala Ala Pro Glu Lys
945                 950                 955                 960
```

```
Lys Asp Thr Lys Glu Glu Lys Ala Lys Lys Pro Glu Lys Pro Lys
                965                 970                 975
Thr Glu Ala Lys Ala Lys Glu Asp Asp Lys Thr Leu Ser Lys Glu Pro
            980                 985                 990
Ser Lys Pro Lys Ala Glu Lys Ala Glu Lys Ser Ser Thr Asp Gln
        995                1000                1005
Lys Asp Ser Lys Pro Pro Glu Lys Ala Thr Glu Asp Lys Ala Ala Lys
    1010                1015                1020
Gly Lys
1025

<210> SEQ ID NO 2
<211> LENGTH: 3081
<212> TYPE: DNA
<213> ORGANISM: Homo sapiens

<400> SEQUENCE: 2
```

| | | | | | |
|---|---|---|---|---|---|
| atgatgagct | tcggcggcgc | ggacgcgctg | ctgggcgccc | cgttcgcgcc | gctgcatggc | 60 |
| ggcggcagcc | tccactacgc | gctagcccga | aagggtggcg | caggcgggac | gcgctccgcc | 120 |
| gctggctcct | ccagcggctt | ccactcgtgg | acacggacgt | ccgtgagctc | cgtgtccgcc | 180 |
| tcgcccagcc | gcttccgtgg | cgcaggcgcc | gcctcaagca | ccgactcgct | ggacacgctg | 240 |
| agcaacgggc | cggagggctg | catggtggcg | gtggccacct | cacgcagtga | aaggagcag | 300 |
| ctgcaggcgc | tgaacgaccg | cttcgccggg | tacatcgaca | aggtgcggca | gctggaggcg | 360 |
| cacaaccgca | gcctggaggg | cgaggctgcg | gcgctgcggc | agcagcaggc | gggccgctcc | 420 |
| gctatgggcg | agctgtacga | gcgcgaggtc | cgcgagatgc | gcggcgcggt | gctgcgcctg | 480 |
| ggcgcggcgc | gcggtcagct | acgcctggag | caggagcacc | tgctcgagga | catcgcgcac | 540 |
| gtgcgccagc | gcctagacga | cgaggcccgg | cagcgagagg | aggccgaggc | ggcggcccgc | 600 |
| gcgctggcgc | gcttcgcgca | ggaggccgag | gcggcgcgcg | tggacctgca | aagaaggcg | 660 |
| caggcgctgc | aggaggagtg | cggctacctg | cggcgccacc | accaggaaga | ggtgggcgag | 720 |
| ctgctcggca | agatccaggg | ctccggcgcc | gcgcaggcgc | agatgcaggc | cgagacgcgc | 780 |
| gacgccctga | agtgcgacgt | gacgtcggcg | ctgcgcgaga | ttcgcgcgca | gcttgaaggc | 840 |
| cacgcggtgc | agagcacgct | gcagtccgag | gagtggttcc | gagtgaggct | ggaccgactg | 900 |
| tcggaggcag | ccaaggtgaa | cacagacgct | atgcgctcag | cgcaggagga | gataactgag | 960 |
| taccggcgtc | agctgcaggc | caggaccaca | gagctggagg | cactgaaaag | caccaaggac | 1020 |
| tcactggaga | ggcagcgctc | tgagctggag | gaccgtcatc | aggccgacat | tgcctcctac | 1080 |
| caggaagcca | ttcagcagct | ggacgctgag | ctgaggaaca | ccaagtggga | gatggccgcc | 1140 |
| cagctgcgag | aataccagga | cctgctcaat | gtcaagatgg | ctctggatat | agagatagcc | 1200 |
| gcttacagaa | aactcctgga | aggtgaagag | tgtcggattg | ctttggccc | aattcctttc | 1260 |
| tcgcttccag | aaggactccc | caaaattccc | tctgtgtcca | ctcacataaa | ggtgaaaagc | 1320 |
| gaagagaaga | tcaaagtggt | ggagaagtct | gagaaagaaa | ctgtgattgt | ggaggaacag | 1380 |
| acagaggaga | cccaagtgac | tgaagaagtg | actgaagaag | aggagaaaga | ggccaaagag | 1440 |
| gaggagggca | aggaggaaga | aggggtgaa | gaagaggagg | cagaagggg | agaagaagaa | 1500 |
| acaaagtctc | ccccagcaga | gaggctgca | tccccagaga | aggaagccaa | gtcaccagta | 1560 |
| aaggaagagg | caaagtcacc | ggctgaggcc | aagtccccag | agaaggagga | agcaaaatcc | 1620 |
| ccagccgaag | tcaagtcccc | tgagaaggcc | aagtctccag | caaaggaaga | ggcaaagtca | 1680 |

-continued

```
ccgcctgagg ccaagtcccc agagaaggag gaagcaaaat ctccagctga ggtcaagtcc    1740
cccgagaagg ccaagtcccc agcaaaggaa gaggcaaagt caccggctga ggccaagtct    1800
ccagagaagg ccaagtcccc agtgaaggaa gaagcaaagt caccggctga ggccaagtcc    1860
ccagtgaagg aagaagcaaa atctccagct gaggtcaagt ccccggaaaa ggccaagtct    1920
ccaacgaagg aggaagcaaa gtcccctgag aaggccaagt ccctgagaaa ggccaagtcc    1980
ccagagaagg aagaggccaa gtcccctgag aaggccaagt ccccagtgaa ggcagaagca    2040
aagtcccctg agaaggccaa gtccccagtg aaggcagaag caaagtcccc tgagaaggcc    2100
aagtccccag tgaaggaaga agcaaagtcc cctgagaagg ccaagtcccc agtgaaggaa    2160
gaagcaaagt cccctgagaa ggccaagtcc ccagtgaagg aagaagcaaa gaccccgag    2220 aaggccaagt ccccagtgaa ggaagaagcc aagtccccag agaaggccaa gtccccagag    2280
aaggccaaga ctcttgatgt gaagtctcca gaagccaaga ctccagcgaa ggaggaagca    2340
aggtcccctg cagacaaatt ccctgaaaag gccaaaagcc ctgtcaagga ggaggtcaag    2400
tccccagaga aggcgaaatc tcccctgaag gaggatgcca aggcccctga aggagatc     2460 ccaaaaaagg aagaggtgaa gtccccagtg aaggaggagg agaagcccca ggaggtgaaa    2520
gtcaaagagc ccccaaagaa ggcagaggaa gagaaagccc ctgccacacc aaaaacagag    2580
gagaagaagg acagcaagaa agaggaggca cccaagaagg aggctccaaa gcccaaggtg    2640
gaggagaaga aggaacctgc tgtcgaaaag cccaaagaat ccaaagttga agccaagaag    2700
gaagaggctg aagataagaa aaaagtcccc accccagaga aggaggctcc tgccaaggtg    2760
gaggtgaagg aagacgctaa acccaaagaa aagacagagg tggccaagaa ggaaccagat    2820
gatgccaagg ccaaggaacc cagcaaacca gcagagaaga aggaggcagc accggagaaa    2880
aaagacacca aggaggagaa ggccaagaag cctgaggaga acccaagac agaggccaaa    2940 gccaaggaag atgacaagac cctctcaaaa gagcctagca agcctaaggc agaaaaggct    3000
gaaaaatcct ccagcacaga ccaaaaagac agcaagcctc cagagaaggc cacagaagac    3060
aaggccgcca aggggaagta a                                             3081
```

<210> SEQ ID NO 3
<211> LENGTH: 1087
<212> TYPE: PRT
<213> ORGANISM: Mus musculus

<400> SEQUENCE: 3

```
Met Ser Phe Gly Ser Ala Asp Ala Leu Leu Gly Ala Pro Phe Ala Pro
 1               5                  10                  15

Leu His Gly Gly Gly Ser Leu His Tyr Ser Leu Ser Arg Lys Ala Gly
             20                  25                  30

Pro Gly Gly Thr Arg Ser Ala Ala Gly Ser Ser Ser Gly Phe His Ser
         35                  40                  45

Trp Ala Arg Thr Ser Val Ser Val Ser Ala Ser Pro Ser Arg Phe
     50                  55                  60

Arg Gly Ala Ala Ser Ser Thr Asp Ser Leu Asp Thr Leu Ser Asn Gly
 65                  70                  75                  80

Pro Glu Gly Cys Val Val Ala Val Ala Ala Arg Ser Glu Lys Glu
                 85                  90                  95

Gln Leu Gln Ala Leu Asn Asp Arg Phe Ala Gly Tyr Ile Asp Lys Val
            100                 105                 110

Arg Gln Leu Glu Ala His Asn Arg Ser Leu Glu Gly Glu Ala Ala Ala
        115                 120                 125
```

```
Leu Arg Gln Gln Lys Gly Arg Ala Ala Met Gly Glu Leu Tyr Glu Arg
    130                 135                 140
Glu Val Arg Glu Met Arg Gly Ala Val Leu Arg Leu Gly Ala Ala Arg
145                 150                 155                 160
Gly Gln Leu Arg Leu Glu Gln Glu His Leu Leu Glu Asp Ile Ala His
                165                 170                 175
Val Arg Gln Arg Leu Asp Glu Glu Ala Arg Gln Arg Glu Glu Ala Glu
            180                 185                 190
Ala Ala Ala Arg Ala Leu Ala Phe Ala Gln Glu Ala Glu Ala Ala Arg
        195                 200                 205
Val Glu Leu Gln Lys Lys Ala Gln Ala Leu Gln Glu Glu Cys Gly Tyr
    210                 215                 220
Leu Arg Arg His His Gln Glu Val Gly Glu Leu Leu Gly Gln Ile
225                 230                 235                 240
Gln Gly Cys Gly Ala Ala Gln Ala Gln Ala Glu Ala Arg Asp
                245                 250                 255
Ala Leu Lys Cys Asp Val Thr Ser Ala Leu Arg Glu Ile Arg Ala Gln
            260                 265                 270
Leu Glu Gly His Ala Val Gln Ser Ser Leu Gln Ser Glu Glu Trp Phe
        275                 280                 285
Arg Val Arg Leu Asp Arg Leu Ser Glu Ala Ala Lys Val Asn Thr Asp
    290                 295                 300
Ala Met Arg Ser Ala Gln Glu Glu Ile Thr Glu Tyr Arg Arg Gln Leu
305                 310                 315                 320
Gln Ala Arg Thr Thr Glu Leu Glu Ala Leu Lys Ser Thr Lys Glu Ser
                325                 330                 335
Leu Glu Arg Gln Arg Ser Glu Leu Glu Asp Arg His Gln Ala Asp Ile
            340                 345                 350
Ala Ser Tyr Gln Asp Ala Ile Gln Gln Leu Asp Ser Glu Leu Arg Asn
        355                 360                 365
Thr Lys Trp Glu Met Ala Ala Gln Leu Arg Glu Tyr Gln Asp Leu Leu
    370                 375                 380
Asn Val Lys Met Ala Leu Asp Ile Glu Ile Ala Ala Tyr Arg Lys Leu
385                 390                 395                 400
Leu Glu Gly Glu Glu Cys Arg Ile Gly Phe Gly Pro Ser Pro Phe Ser
                405                 410                 415
Leu Thr Glu Gly Leu Pro Lys Ile Pro Ser Ile Ser Thr His Ile Lys
            420                 425                 430
Val Lys Ser Glu Glu Met Ile Lys Val Val Glu Lys Ser Glu Lys Glu
        435                 440                 445
Thr Val Ile Val Glu Gly Gln Thr Glu Glu Ile Arg Val Thr Glu Gly
    450                 455                 460
Val Thr Glu Glu Glu Asp Lys Glu Ala Gln Gly Gln Glu Gly Glu Glu
465                 470                 475                 480
Ala Glu Glu Gly Glu Glu Lys Glu Glu Glu Leu Ala Ala Ala Thr
                485                 490                 495
Ser Pro Pro Ala Glu Glu Ala Ala Ser Pro Glu Lys Glu Thr Lys Ser
            500                 505                 510
Arg Val Lys Glu Glu Ala Lys Ser Pro Gly Glu Ala Lys Ser Pro Gly
        515                 520                 525
Glu Ala Lys Ser Pro Ala Glu Ala Lys Ser Pro Gly Glu Ala Lys Ser
    530                 535                 540
```

```
Pro Gly Glu Ala Lys Ser Pro Gly Glu Ala Lys Ser Pro Ala Glu Pro
545                 550                 555                 560
Lys Ser Pro Ala Glu Pro Lys Ser Pro Ala Glu Ala Lys Ser Pro Ala
                565                 570                 575
Glu Pro Lys Ser Pro Ala Thr Val Lys Ser Pro Gly Glu Ala Lys Ser
            580                 585                 590
Pro Ser Glu Ala Lys Ser Pro Ala Glu Ala Lys Ser Pro Ala Glu Ala
        595                 600                 605
Lys Ser Pro Ala Glu Ala Lys Ser Pro Ala Glu Ala Lys Ser Pro Ala
    610                 615                 620
Glu Ala Lys Ser Pro Ala Glu Ala Lys Ser Pro Ala Thr Val Lys Ser
625                 630                 635                 640
Pro Gly Glu Ala Lys Ser Pro Ser Glu Ala Lys Ser Pro Ala Glu Ala
                645                 650                 655
Lys Ser Pro Ala Glu Ala Lys Ser Pro Ala Glu Ala Lys Ser Pro Ala
                660                 665                 670
Glu Val Lys Ser Pro Gly Glu Ala Lys Ser Pro Ala Glu Pro Lys Ser
            675                 680                 685
Pro Ala Glu Ala Lys Ser Pro Ala Glu Val Lys Ser Pro Ala Glu Ala
        690                 695                 700
Lys Ser Pro Ala Glu Val Lys Ser Pro Gly Glu Ala Lys Ser Pro Ala
705                 710                 715                 720
Ala Val Lys Ser Pro Ala Glu Ala Lys Ser Pro Ala Ala Val Lys Ser
                725                 730                 735
Pro Gly Glu Ala Lys Ser Pro Gly Glu Ala Lys Ser Pro Ala Glu Ala
                740                 745                 750
Lys Ser Pro Ala Glu Ala Lys Ser Pro Ile Glu Val Lys Ser Pro Glu
                755                 760                 765
Lys Ala Lys Thr Pro Val Lys Glu Gly Ala Lys Ser Pro Ala Glu Ala
            770                 775                 780
Lys Ser Pro Glu Lys Ala Lys Ser Pro Val Lys Glu Asp Ile Lys Pro
785                 790                 795                 800
Pro Ala Glu Ala Lys Ser Pro Glu Lys Ala Lys Ser Pro Val Lys Glu
                805                 810                 815
Gly Ala Lys Pro Pro Glu Lys Ala Lys Pro Leu Asp Val Lys Ser Pro
            820                 825                 830
Glu Ala Gln Thr Pro Val Gln Glu Ala Thr Val Pro Thr Asp Ile
        835                 840                 845
Arg Pro Pro Glu Gln Val Lys Ser Pro Ala Lys Glu Lys Ala Lys Ser
    850                 855                 860
Pro Glu Lys Glu Ala Lys Thr Ser Glu Lys Val Ala Pro Lys Lys
865                 870                 875                 880
Glu Glu Val Lys Ser Pro Val Lys Glu Val Lys Ala Lys Glu Pro
                885                 890                 895
Pro Lys Lys Val Glu Glu Lys Thr Leu Pro Thr Pro Lys Thr Glu
        900                 905                 910
Ala Lys Glu Ser Lys Lys Asp Glu Ala Pro Lys Glu Ala Pro Lys Pro
            915                 920                 925
Lys Val Glu Glu Lys Lys Glu Thr Pro Thr Lys Pro Lys Asp Ser
    930                 935                 940
Thr Ala Glu Ala Lys Lys Glu Glu Ala Gly Glu Lys Lys Lys Ala Val
945                 950                 955                 960
Ala Ser Glu Glu Glu Thr Pro Ala Lys Leu Gly Val Lys Glu Glu Ala
```

-continued

```
                965                 970                 975
Lys Pro Lys Glu Lys Thr Glu Thr Thr Lys Thr Glu Ala Glu Asp Thr
            980                 985                 990
Lys Ala Lys Glu Pro Ser Lys Pro Thr Glu Thr Glu Lys Pro Lys Lys
            995                 1000                1005
Glu Glu Met Pro Ala Ala Pro Glu Lys Lys Asp Thr Lys Glu Glu Lys
            1010                1015                1020
Thr Thr Glu Ser Arg Lys Pro Glu Glu Lys Pro Lys Met Glu Ala Lys
1025                1030                1035                1040
Val Lys Glu Asp Asp Lys Ser Leu Ser Lys Glu Pro Ser Lys Pro Lys
                1045                1050                1055
Thr Glu Lys Ala Glu Lys Ser Ser Ser Thr Asp Gln Lys Glu Ser Gln
                1060                1065                1070
Pro Pro Glu Lys Thr Thr Glu Asp Lys Ala Thr Lys Gly Glu Lys
                1075                1080                1085

<210> SEQ ID NO 4
<211> LENGTH: 3219
<212> TYPE: DNA
<213> ORGANISM: Mus musculus

<400> SEQUENCE: 4
atgatgagct tcggcagcgc cgatgcgctg ctgggcgccc cgttcgcgcc gctgcacgga     60
ggcggcagcc tgcactactc gctgagccgc aaggcaggcc cgggcggcac gcgctccgcg    120
gccggctcct ccagcggctt ccactcgtgg gcgcggacgt ccgtgagctc cgtgtccgcc    180
tcacccagcc gcttccgcgg cgccgcctcg agcaccgact cgctagacac cctaagcaac    240
ggcccagagg gctgcgtggt ggcggcggtg gcggcgcgca gcgagaagga gcagctgcag    300
gctctgaacg accgcttcgc gggctacatc gacaaggtga ggcagctcga ggcgcacaac    360
cgcagcctgg agggcgaggc ggcggcgctg cggcagcaac aagccggccg cgccgccatg    420
ggcgagctgt acgagcgcga ggtgcgcgag atgcgcggcg ccgtgctgcg cctcggggcg    480
gcgcgcgggc agctgcgcct ggagcaggag cacctgctgg aggacatcgc tcacgtccgc    540
cagcggctgg acgaggaggc ccggcagcgt gaggaggcgg aggcggcggc gcgcgccctg    600
gcgcgcttcg cgcaggaggc ggaagcggcg cgcgtggagc tgcagaagaa ggcgcaggcg    660
ctgcaggagg agtgcggcta cctgcggcgc caccaccagg aggaggtggg cgagctgctc    720
ggtcagatcc agggctgcgg ggccgcgcag gcgcaggctc aggccgaggc tcgcgacgcc    780
ctcaagtgcg acgtgacgtc ggcgctgcgg gagatccgcg cgcagctcga aggccacgcg    840
gtgcagagca cgctgcagtc cgaggagtgg ttccgagtga ggttggaccg actctcagag    900
gcagccaaag tgaacacaga tgctatgcgc tcggcccaag aggagataac tgagtaccgg    960
cggcagctgc aagccaggac cacagagttg gaggccctga aaagcaccaa ggagtcactg   1020
gagaggcagc gctctgagct agaggaccgt catcaggcag acattgcctc ctaccaggac   1080
gctattcagc agctggacag tgagctgaga acaccaagt gggagatggc tgcacagctc   1140
cgagagtacc aggacctgct caacgtcaag atggccctgg acattgagat tgccgcttac   1200
agaaagctcc tggaaggcga agagtgtcgg attggctttg gtccgagtcc cttctctctt   1260
actgaaggac tcccaaaaat tccctccata tccacgcaca taaagtcaa agcgaagag    1320 atgataaagg tagtagagaa atccgagaag gaaactgtga ttgtagaagg acagacagaa   1380
gagatccggg tgacggaagg agtgacagaa gaggaggaca aagaggccca aggtcaggaa   1440
```

```
ggagaagaag cagaagaggg agaagaaaaa gaaggagcagc agctacatct      1500 cccctgcag aagaggctgc atctccagaa aaagaaacca agtctcgtgt gaaagaagag      1560
gccaagtccc caggtgaggc caagtcccca ggtgaggcca agtccccagg tgaggccaag      1620
tccccagctg aggccaagtc cccaggtgag gccaagtccc cacgtgaggc caagtcccca      1680
ggtgaggcca agtctccagc tgagcccaag tctccagctg agcccaagtc tccagctgag      1740
gccaagtcac cagctgagcc caagtctcca gctacagtga agtctccagg tgaggccaag      1800
tcaccatctg aggccaaatc tccagctgaa gccaaatctc agctgaggc caaatctcca      1860 gctgaggcca atctccagc tgaggccaag tcaccagctg aagccaagtc accagctgaa      1920
gccaaatctc agctacagt gaagtctcca ggtgaggcca agtcaccatc tgaggccaaa      1980
tctccagctg aagccaaatc tccagctgag gccaaatctc agctgaggc caaatctcca      2040 gctgaggtca agtcaccagg tgaggccaag tctccagctg agcccaagtc accagctgag      2100
gccaaatctc agctgcagt gaagtcacca gctgaggcca agtctccagc tgcagtcaag      2160
tccccaggtg aggccaagtc cccaggtgag gccaagtcac cagctgaggc caaatctcca      2220
gctgaggcca agtcaccaat tgaggtaaaa tctccagaga aggccaagac ccccgtcaag      2280
gaaggagcaa atctccagc tgaggccaag tctcctgaga aggccaagtc ccccgtgaag      2340
gaagatatca gcccccagc tgaggcgaaa tcccctgaga aggccaagag ccccatgaag      2400
gaaggagcaa agcctcctga gaaggccaag cctctagatg tgaagtctcc ggaagcccag      2460
actccagtac aggaggaagc gaacgacccc acagacatca gacccctga gcaggtgaaa      2520 agtcctgcca aggagaaggc caagtcccct gagaaggaag aagccaagac ttctgaaaag      2580
gtggctccca gaaggaaga ggtgaagtcc cctgtgaagg aggaggtaaa agccaaagaa      2640 ccccaaaga aggtagaaga agagaagaca ctgcctacac caaagacaga ggcgaaggag      2700
agtaagaaag acgaagctcc caaggaggcc ccgaagccca aggtggagga gaagaaggaa      2760
actcccacgg aaaagcccaa ggactctaca gcagaagcca gaaggaaga ggctggagag      2820 aagaagaaag ccgtgccctc agaggaggag actcctgcca agtgggtgt gaaggaagaa      2880 gctaaaccca agagaagac agagacaacc aagacagaag cagaagacac caaggccaaa      2940
gaacctagca aacccacaga gacggaaaag ccaaagaaag aggagatgcc agcggcacca      3000
gagaagaaag acaccaagga ggagaagacc acagagtcca ggaagcctga ggagaagccc      3060
aaaatggagg ccaaggtcaa ggaggatgac aagagccttt ccaaagagcc tagcaaaccc      3120
aagacagaaa aggctgaaaa atcctctagc acagaccaga agaaagcca gccccagag      3180 aagaccacag aggacaaggc caccaaggga gagaagtaa                           3219
```

<210> SEQ ID NO 5
<211> LENGTH: 925
<212> TYPE: PRT
<213> ORGANISM: Bos taurus

<400> SEQUENCE: 5

```
Ser Tyr Thr Leu Asp Ser Leu Gly Asn Pro Ser Ala Tyr Arg Arg Val
 1               5                   10                  15

Thr Glu Thr Arg Ser Ser Phe Ser Arg Ile Ser Gly Ser Pro Ser Ser
            20                  25                  30

Gly Phe Arg Ser Gln Ser Trp Ser Arg Gly Ser Pro Ser Thr Val Ser
        35                  40                  45

Ser Ser Tyr Lys Arg Ser Ala Leu Ala Pro Arg Leu Thr Tyr Ser Ser
    50                  55                  60
```

-continued

```
Ala Met Leu Ser Ser Ala Glu Ser Ser Leu Asp Phe Ser Gln Ser Ser
 65                  70                  75                  80

Ser Leu Leu Asp Gly Ser Gly Pro Gly Gly Asp Tyr Lys Leu Ser
                 85                  90                  95

Arg Ser Asn Glu Lys Glu Gln Ile Gln Gly Leu Asn Asp Arg Phe Ala
            100                 105                 110

Gly Tyr Ile Glu Lys Val His Tyr Leu Glu Gln Gln Asn Lys Glu Ile
                115                 120                 125

Glu Ala Glu Ile Gln Ala Leu Arg Gln Lys Gln Ala Ser His Ala Gln
130                 135                 140

Leu Gly Asp Ala Tyr Asp Gln Glu Ile Arg Glu Leu Arg Ala Thr Leu
145                 150                 155                 160

Glu Met Val Asn His Glu Lys Ala Gln Val Gln Leu Asp Ser Asp His
                165                 170                 175

Leu Glu Glu Asp Ile His Arg Leu Lys Glu Arg Phe Glu Glu Glu Ala
                180                 185                 190

Arg Leu Arg Asp Asp Thr Glu Ala Ala Ile Arg Ala Leu Arg Lys Asp
            195                 200                 205

Ile Glu Glu Ser Ser Leu Val Lys Val Glu Leu Asp Lys Lys Val Gln
210                 215                 220

Ser Leu Gln Asp Glu Val Ala Phe Leu Arg Ser Asn His Glu Glu Glu
225                 230                 235                 240

Val Ala Asp Leu Leu Ala Gln Ile Gln Ala Ser His Ile Thr Val Glu
                245                 250                 255

Arg Lys Asp Tyr Leu Lys Thr Asp Ile Ser Thr Ala Leu Lys Glu Ile
            260                 265                 270

Arg Ser Gln Leu Glu Ser His Ser Asp Gln Asn Met His Gln Ala Glu
        275                 280                 285

Glu Trp Phe Lys Cys Arg Tyr Ala Lys Leu Thr Glu Ala Ala Glu Gln
290                 295                 300

Asn Lys Glu Ala Ile Arg Ser Ala Lys Glu Glu Ile Ala Glu Tyr Arg
305                 310                 315                 320

Arg Gln Leu Gln Ser Lys Ser Ile Glu Leu Glu Ser Val Arg Gly Thr
                325                 330                 335

Lys Glu Ser Leu Glu Arg Gln Leu Ser Asp Ile Glu Glu Arg His Asn
            340                 345                 350

His Asp Leu Ser Ser Tyr Gln Asp Thr Ile Gln Gln Leu Glu Asn Glu
        355                 360                 365

Leu Arg Gly Thr Lys Trp Glu Met Ala Arg His Leu Arg Glu Tyr Gln
370                 375                 380

Asp Leu Leu Asn Val Lys Met Ala Leu Asp Ile Glu Ile Ala Ala Tyr
385                 390                 395                 400

Arg Lys Leu Leu Glu Gly Glu Glu Thr Arg Phe Ser Thr Phe Ala Gly
                405                 410                 415

Ser Ile Thr Gly Pro Leu Tyr Thr His Arg Gln Pro Ser Ile Ala Ile
            420                 425                 430

Ser Ser Lys Ile Gln Lys Thr Lys Val Glu Ala Pro Lys Leu Lys Val
        435                 440                 445

Gln His Lys Phe Val Glu Glu Ile Ile Glu Glu Thr Lys Val Glu Asp
    450                 455                 460

Glu Lys Ser Glu Met Glu Glu Ala Leu Thr Ala Ile Thr Glu Glu Leu
465                 470                 475                 480
```

-continued

```
Ala Val Ser Val Lys Glu Val Lys Glu Glu Ala Glu Lys
            485             490             495
Glu Glu Lys Glu Glu Ala Glu Glu Val Ala Ala Lys Lys Ser
            500             505             510
Pro Val Lys Ala Thr Ala Pro Glu Leu Lys Glu Glu Gly Glu Lys
            515             520             525
Glu Glu Glu Glu Gly Gln Glu Glu Glu Glu Glu Glu Ala Ala
            530             535             540
Lys Ser Asp Gln Ala Glu Gly Gly Ser Glu Lys Glu Gly Ser Ser
545             550             555             560
Glu Lys Glu Glu Gly Glu Gln Glu Glu Gly Glu Thr Glu Ala Glu
            565             570             575
Gly Glu Gly Glu Glu Ala Ala Glu Ala Lys Glu Glu Lys Lys Met
            580             585             590
Glu Glu Lys Ala Glu Glu Val Ala Pro Lys Glu Glu Leu Ala Ala Glu
            595             600             605
Ala Lys Val Glu Lys Pro Glu Lys Ala Lys Ser Pro Val Ala Lys Ser
            610             615             620
Pro Thr Thr Lys Ser Pro Thr Ala Lys Ser Pro Glu Ala Lys Ser Pro
625             630             635             640
Glu Ala Lys Ser Pro Thr Ala Lys Ser Pro Thr Ala Lys Ser Pro Val
            645             650             655
Ala Lys Ser Pro Thr Ala Lys Ser Pro Glu Ala Lys Ser Pro Glu Ala
            660             665             670
Lys Ser Pro Thr Ala Lys Ser Pro Thr Ala Lys Ser Pro Ala Ala Lys
            675             680             685
Ser Pro Ala Pro Lys Ser Pro Val Glu Val Lys Pro Lys Ala Glu
            690             695             700
Ala Gly Ala Glu Lys Gly Glu Gln Lys Glu Lys Val Glu Glu Glu Lys
705             710             715             720
Lys Glu Ala Lys Glu Ser Pro Lys Glu Glu Lys Ala Glu Lys Lys Glu
            725             730             735
Glu Lys Pro Lys Asp Val Pro Glu Lys Lys Ala Glu Ser Pro Val
            740             745             750
Lys Ala Glu Ser Pro Val Lys Glu Glu Val Pro Ala Lys Pro Val Lys
            755             760             765
Val Ser Pro Glu Lys Glu Ala Lys Glu Glu Lys Pro Gln Glu Lys
770             775             780
Glu Lys Glu Lys Glu Lys Val Glu Lys Val Gly Lys Glu Glu Gly
785             790             795             800
Gly Leu Lys Glu Ser Arg Lys Glu Asp Ile Ala Ile Asn Gly Glu Val
            805             810             815
Glu Gly Lys Glu Glu Gln Glu Thr Lys Glu Lys Gly Ser Gly Gly
            820             825             830
Glu Glu Glu Lys Gly Val Val Thr Asn Gly Leu Asp Val Ser Pro Gly
            835             840             845
Asp Glu Lys Lys Gly Gly Asp Lys Ser Glu Glu Lys Val Val Val Thr
850             855             860
Lys Met Val Glu Lys Ile Thr Ser Glu Gly Gly Asp Gly Ala Thr Lys
865             870             875             880
Tyr Ile Thr Lys Ser Val Thr Val Thr Gln Lys Val Glu Glu His Glu
            885             890             895
Glu Thr Phe Glu Glu Lys Leu Val Ser Thr Lys Lys Val Glu Lys Val
```

|  |  |  |  |  |  |
|---|---|---|---|---|---|
| Thr | Ser | His | Ala | Ile | Val | Lys | Glu | Val | Thr | Gln | Ser | Asp |
| 900 | | | | 905 | | | | 910 | | | | |
| | | 915 | | | | 920 | | | | 925 | | |

<210> SEQ ID NO 6
<211> LENGTH: 2433
<212> TYPE: DNA
<213> ORGANISM: Bos Taurus

<400> SEQUENCE: 6

```
gagaaggtcc actacctgga gcagcagaac aaggagatcg aggcagagat ccaggcgctg      60
cggcagaagc aggcctcgca cgcccagctg ggcgacgcgt acgaccagga aatccgcgag     120
ctacgcgcca ccctggagat ggtgaaccat gagaaggctc aggtacagct ggactcggac     180
cacctggaag aggatatcca ccggctcaag gagcgcttcg aggaggaggc acggctgcgc     240
gacgacaccg aggcggctat ccgcgcgctg cgcaaagata tcgaggagtc gtcgctggtc     300
aaggtggagc tggacaagaa ggtgcagtcg ctgcaggatg aggtggcctt cctgcggagc     360
aatcacgagg aggaggtggc cgacctgctg gcccagatcc aagcgtcgca catcacggtg     420
gagcgcaaag actacctgaa gacggacatc tcgacggcgc tgaaagagat ccgctcccag     480
ctcgagagtc actccgacca gaacatgcac caggccgaag agtggtttaa gtgccgctac     540
gccaagctca ccgaggcggc cgagcagaac aaggaagcca tccgctccgc caaggaagag     600
atcgccgagt accggcgcca gctgcagtcc aagagcatcg agctcgagtc agtgcgcggc     660
accaaggagt ccctggagcg gcagctcagc gacatcgagg agcgccacaa ccacgacctt     720
agcagctacc aggacaccat ccagcagctg gaaaatgagc ttcggggcac aaagtgggaa     780
atggctcgtc atctgcgaga ataccaggat ctcctcaacg tcaagatggc tctggatatt     840
gagatcgcgg cgtacaggaa actcctggag ggtgaagaga ccagatttag cacatttgcg     900
ggtagcatca ctgggccact gtatacacac cgacagccct ccatcgccat atccagtaag     960
attcagaaaa ccaaggtaga ggctcccaag ctaaaggtcc aacacaaatt tgttgaggag    1020
attatagagg aaaccaaggt ggaagatgag aaatcagaaa tggaagaagc cctgacggcc    1080
attaccgagg aattggccgt ttccgtgaaa gaggaggtca aggaagagga ggctgaagaa    1140
aaggaggaga agaagaagc cgaagaagaa gttgttgctg ccaaaaagtc tccagtgaaa    1200
gctactgcac ctgaacttaa agaagaggaa ggagaaaagg aggaggaaga gggccaagag    1260
gaagaggaag aggaagaaga ggctgctaag tcagaccaag ccgaggaagg aggatctgag    1320
aaggaaggtt ctagtgaaaa agaggaaggt gagcaagaag aggaaggaga aacagaggct    1380
gagggggaag agaggaagc cgctgccgaa gctaaggagg aaaagaaaat ggaggaaaag    1440
gctgaagaag tggctccaaa ggaggagctg gcggcagaag ccaaggtgga aagccagag     1500
aaagccaagt cccagtggc caagtcccca acaacaaagt ccccaacggc caagtcccca    1560
gaggcaaagt cccagagc aaagtcccca acagcaaaat cccgacggc caagtcccca    1620
gtggccaagt cccgacggc caagtcccca gaggcaaagt cccagaggc aaagtcccca    1680
acagcaaaat cccgacggc caagtcccca gcagcaaagt cccagcgcc aaaatcacct    1740
gtggaggaag tgaaacccaa agcagaagct ggagctgaga aggaaaca gaaggagaag     1800
gtggaggaag aaaagaaaga agcaaaggaa tctcccaagg aagagaaggc agagaaaaag    1860
gaggagaagc caaggatgt gccagagaag aagaaggctg aatccccagt gaaggctgag    1920
tccccagtga aggaggaggt gcctgccaag ccagtaaagg tgagcccaga gaaggaagcc    1980
```

```
aaagaggagg agaagccaca ggagaaagag aaggagaagg agaaagtgga agaggtggga    2040
gggaaggagg agggaggttt gaaggaatcc aggaaggaag acatagccat caatggggag    2100
gtggaaggga aggaggaaga acaggaaact aaggagaaag gcagtggggg agaaagaggag   2160 aaaggagtcg tcaccaacgg cctagacgtg agcccagggg atgaaaagaa gggcggtgat    2220
aaaagtgagg agaaagtggt ggtaaccaaa atggtggaaa aaatcaccag tgagggggga    2280
gatggtgcta ccaagtatat caccaaatct gtaaccgtca ctcaaaaggt cgaagagcat    2340
gaagagacct ttgaggagaa actagtgtct actaaaaagg tagagaaagt cacttcacac    2400
gccatagtaa aggaagtcac ccagagtgac taa                                 2433
```

<210> SEQ ID NO 7
<211> LENGTH: 857
<212> TYPE: PRT
<213> ORGANISM: Gallus gallus

<400> SEQUENCE: 7

```
Ser Tyr Thr Met Glu Pro Leu Gly Asn Pro Ser Tyr Arg Arg Val Met
 1               5                  10                  15

Thr Glu Thr Arg Ala Thr Tyr Ser Arg Ala Ser Ala Ser Pro Ser Ser
             20                  25                  30

Gly Phe Arg Ser Gln Ser Trp Ser Arg Gly Ser Gly Ser Thr Val Ser
         35                  40                  45

Ser Ser Tyr Lys Arg Thr Asn Leu Gly Ala Pro Arg Thr Ala Tyr Gly
     50                  55                  60

Ser Thr Val Leu Ser Ser Ala Glu Ser Leu Asp Val Ser Gln Ser Ser
 65                  70                  75                  80

Leu Leu Asn Gly Ala Ala Glu Leu Lys Leu Ser Arg Ser Asn Glu Lys
                 85                  90                  95

Glu Gln Leu Gln Gly Leu Asn Asp Arg Phe Ala Gly Tyr Ile Glu Lys
            100                 105                 110

Val His Tyr Leu Glu Gln Gln Asn Lys Glu Ile Glu Ala Glu Leu Ala
        115                 120                 125

Ala Leu Arg Gln Lys His Ala Gly Arg Ala Gln Leu Gly Asp Ala Tyr
    130                 135                 140

Glu Gln Glu Leu Arg Glu Leu Arg Gly Ala Leu Glu Gln Val Ser His
145                 150                 155                 160

Glu Lys Ala Gln Ile Gln Leu Asp Ser Glu His Ile Glu Glu Asp Ile
                165                 170                 175

Gln Arg Leu Arg Glu Arg Phe Glu Asp Glu Ala Arg Leu Arg Asp Glu
            180                 185                 190

Thr Glu Ala Thr Ile Ala Ala Leu Arg Lys Glu Met Glu Glu Ala Ser
        195                 200                 205

Leu Met Arg Ala Glu Leu Asp Lys Lys Val Gln Ser Leu Gln Asp Glu
    210                 215                 220

Val Ala Phe Leu Arg Gly Asn His Glu Glu Glu Val Ala Glu Leu Leu
225                 230                 235                 240

Ala Gln Leu Gln Ala Ser His Ala Thr Val Glu Arg Lys Asp Tyr Leu
                245                 250                 255

Lys Thr Asp Leu Thr Thr Ala Leu Lys Glu Ile Arg Ala Gln Leu Glu
            260                 265                 270

Cys Gln Ser Asp His Asn Met His Gln Ala Glu Glu Trp Phe Lys Cys
        275                 280                 285

Arg Tyr Ala Lys Leu Thr Glu Ala Ala Glu Gln Asn Lys Glu Ala Ile
```

-continued

```
            290                 295                 300
Arg Ser Ala Lys Glu Glu Ile Ala Glu Tyr Arg Arg Gln Leu Gln Ser
305                 310                 315                 320

Lys Ser Ile Glu Leu Glu Ser Val Arg Gly Thr Lys Glu Ser Leu Glu
                325                 330                 335

Arg Gln Leu Ser Asp Ile Glu Glu Arg His Asn Asn Asp Leu Thr Thr
                340                 345                 350

Tyr Gln Asp Thr Ile His Gln Leu Glu Asn Glu Leu Arg Gly Thr Lys
                355                 360                 365

Trp Glu Met Ala Arg His Leu Arg Glu Tyr Gln Asp Leu Leu Asn Val
370                 375                 380

Lys Met Ala Leu Asp Ile Glu Ile Ala Ala Tyr Arg Lys Leu Leu Glu
385                 390                 395                 400

Gly Glu Glu Thr Arg Phe Ser Ala Phe Ser Gly Ser Ile Thr Gly Pro
                405                 410                 415

Ile Phe Thr His Arg Gln Pro Ser Val Thr Ile Ala Ser Thr Lys Ile
                420                 425                 430

Gln Lys Thr Lys Ile Glu Pro Pro Lys Leu Lys Val Gln His Lys Phe
                435                 440                 445

Val Glu Glu Ile Ile Glu Glu Thr Lys Val Glu Asp Glu Lys Ser Glu
                450                 455                 460

Met Glu Asp Ala Leu Ser Ala Ile Ala Glu Glu Met Ala Lys Ala
465                 470                 475                 480

Gln Glu Glu Glu Gln Glu Glu Lys Ala Glu Glu Ala Val Glu
                485                 490                 495

Glu Glu Ala Val Ser Glu Lys Ala Ala Glu Gln Ala Ala Glu Glu Glu
                500                 505                 510

Glu Lys Glu Glu Glu Ala Glu Glu Ala Ala Lys Ser Asp
                515                 520                 525

Ala Ala Glu Glu Gly Gly Ser Lys Lys Glu Glu Ile Glu Glu Lys Glu
                530                 535                 540

Glu Gly Glu Glu Ala Glu Glu Glu Ala Glu Ala Lys Gly Lys Ala
545                 550                 555                 560

Glu Glu Ala Gly Ala Lys Val Glu Lys Val Lys Ser Pro Ala Lys
                565                 570                 575

Ser Pro Pro Lys Ser Pro Lys Ser Pro Val Thr Glu Gln Ala Lys
                580                 585                 590

Ala Val Gln Lys Ala Ala Ala Glu Val Gly Lys Asp Gln Lys Ala Glu
                595                 600                 605

Lys Ala Ala Glu Lys Ala Ala Lys Glu Glu Lys Ala Ala Ser Pro Glu
                610                 615                 620

Lys Pro Ala Thr Pro Lys Val Thr Ser Pro Glu Lys Pro Ala Thr Pro
625                 630                 635                 640

Glu Lys Pro Pro Thr Pro Glu Lys Ala Ile Thr Pro Glu Lys Val Arg
                645                 650                 655

Ser Pro Glu Lys Pro Thr Thr Pro Glu Lys Val Val Ser Pro Glu Lys
                660                 665                 670

Pro Ala Ser Pro Glu Lys Pro Arg Thr Pro Glu Lys Pro Ala Ser Pro
                675                 680                 685

Glu Lys Pro Ala Thr Pro Glu Lys Pro Arg Thr Pro Glu Lys Pro Ala
                690                 695                 700

Thr Pro Glu Lys Pro Arg Ser Pro Glu Lys Pro Ser Ser Pro Leu Lys
705                 710                 715                 720
```

```
Asp Glu Lys Ala Val Val Glu Glu Ser Ile Thr Val Thr Lys Val Thr
                725                 730                 735

Lys Val Thr Ala Glu Val Glu Val Ser Lys Glu Ala Arg Lys Glu Asp
            740                 745                 750

Ile Ala Val Asn Gly Glu Val Glu Glu Lys Lys Asp Glu Ala Lys Glu
        755                 760                 765

Lys Glu Ala Glu Glu Glu Glu Lys Gly Val Val Thr Asn Gly Leu Asp
    770                 775                 780

Val Ser Pro Val Asp Glu Lys Gly Glu Lys Val Val Thr Lys Lys
785                 790                 795                 800

Ala Glu Lys Ile Thr Ser Glu Gly Gly Asp Ser Thr Thr Tyr Ile
                805                 810                 815

Thr Lys Ser Val Thr Val Thr Gln Lys Val Glu His Glu Ser
                820                 825                 830

Phe Glu Glu Lys Leu Val Ser Thr Lys Lys Val Glu Lys Val Thr Ser
            835                 840                 845

His Ala Val Val Lys Glu Ile Lys Glu
    850                 855
```

<210> SEQ ID NO 8
<211> LENGTH: 1530
<212> TYPE: DNA
<213> ORGANISM: Gallus gallus

<400> SEQUENCE: 8

```
gacctcacca cctatcagga cacgatccat cagctggaaa atgagctcag aggaacgaag    60
tgggagatgg cacgtcattt gagggagtac caggatctcc tcaatgtcaa gatggccctg   120
gatatcgaaa ttgctgcata caggaagctg ctggagggtg aggagacaag attcagtgcc   180
ttctctggaa gcatcactgg acccatattc acacacagac aaccatcggt cacaatagca   240
tccactaaaa tacagaaaac caaaatcgag ccaccaaagc tgaaggtcca gcacaaattt   300
gtagaagaaa tcattgaaga acgaaagta gaggatgaga agtctgaaat ggaagatgcc   360
ctctcagcca ttgcagaaga aatggcagca aaggctcagg aggaagaaca ggaggaggaa   420
aaggcagaag aagaagctgt agaggaagaa gctgtttctg agaaggctgc agaacaggca   480
gctgaggaag aagagaagga ggaagaagaa gcagaggagg aagaagctgc aaaatcagac   540
gctgcagaag aaggaggctc taaaaaggaa gaaatagagg aaaaggaaga aagggaggag   600
gctgaagaag aagaagctga agccaagggc aaagctgaag aggcaggtgc aaaggtagaa   660
aaagtgaaat cacctcctgc aaagtcaccc cctaaatccc cctaaatc cctgtaaca     720
gagcaagcca aggccgtcca gaaagcagca gcagaggtag aaaggatca gaaagcagag   780
aaagctgctg agaaggcagc caaggaggag aaggcagcat ccccagagaa gccggcgaca   840
ccaaaggtga cctccccgga gaaccagcg actccggaga accaccaac cccagagaaa   900
gcgatcaccc cggagaaggt ccgttcccca gaaaaaccaa caccccgga aaaagtggtg   960
agcccagaga accagcaag cccagagaag ccccgaaccc cagagaaacc agcaagcccc  1020
gaaaaaccgg caacaccaga gaagccccgc actcctgaaa agccagcgac gccggagaag  1080
ccccgttctc cagagaagcc atcctccccg ctcaaagatg aaaaggctgt ggtggaggag  1140
agcatcactg tcacaaaggt aacaaaagtc actgcagagg tggaggtgtc gaaggaagcc  1200
aggaaagaag acattgcggt gaatggtgaa gtggaggaga gaaggatga gcgaaggag  1260
aaggaggctg aggaggaaga gaagggcgtt gtcaccaatg gctcgatgt gagccccgtc  1320
```

-continued

```
gatgagaagg gtgagaaagt tgtagtaacc aaaaaagcag agaaaatcac aagtgaagga    1380
ggggacagta ctaccacgta catcacgaag tcggtgacgg tcactcagaa ggtggaggaa    1440
cacgaagaga gctttgagga gaaattggtg tccactaaga aagtggagaa agttacttca    1500
catgctgtag taaagagat taaagaatga                                      1530
```

<210> SEQ ID NO 9
<211> LENGTH: 915
<212> TYPE: PRT
<213> ORGANISM: Homo sapiens

<400> SEQUENCE: 9

```
Ser Tyr Thr Leu Asp Ser Leu Gly Asn Pro Ser Ala Tyr Arg Arg Val
  1               5                  10                  15

Thr Glu Thr Arg Ser Ser Phe Ser Arg Val Ser Gly Ser Pro Ser Ser
                 20                  25                  30

Gly Phe Arg Ser Gln Ser Trp Ser Arg Gly Ser Pro Ser Thr Val Ser
             35                  40                  45

Ser Ser Tyr Lys Arg Ser Met Leu Ala Pro Arg Leu Ala Tyr Ser Ser
         50                  55                  60

Ala Met Leu Ser Ser Ala Glu Ser Ser Leu Asp Phe Ser Gln Ser Ser
 65                  70                  75                  80

Ser Leu Leu Asn Gly Gly Ser Gly Pro Gly Gly Asp Tyr Lys Leu Ser
                 85                  90                  95

Arg Ser Asn Glu Lys Glu Gln Leu Gln Gly Leu Asn Asp Arg Phe Ala
            100                 105                 110

Gly Tyr Ile Glu Lys Val His Tyr Leu Glu Gln Gln Asn Lys Glu Ile
        115                 120                 125

Glu Ala Glu Ile Gln Ala Leu Arg Gln Lys Gln Ala Ser His Ala Gln
    130                 135                 140

Leu Gly Asp Ala Tyr Asp Gln Glu Ile Arg Glu Leu Arg Ala Thr Leu
145                 150                 155                 160

Glu Met Val Asn His Glu Lys Ala Gln Val Gln Leu Asp Ser Asp His
                165                 170                 175

Leu Glu Glu Asp Ile His Arg Leu Lys Glu Arg Phe Glu Glu Glu Ala
            180                 185                 190

Arg Leu Arg Asp Asp Thr Glu Ala Ala Ile Arg Ala Leu Arg Lys Asp
        195                 200                 205

Ile Glu Glu Ala Ser Leu Val Lys Val Glu Leu Asp Lys Lys Val Gln
    210                 215                 220

Ser Leu Gln Asp Glu Val Ala Phe Leu Arg Ser Asn His Glu Glu Glu
225                 230                 235                 240

Val Ala Asp Leu Leu Ala Gln Ile Gln Ala Ser His Ile Thr Val Glu
                245                 250                 255

Arg Lys Asp Tyr Leu Lys Thr Asp Ile Ser Thr Ala Leu Lys Glu Ile
            260                 265                 270

Arg Ser Gln Leu Glu Ser His Ser Asp Gln Asn Met His Gln Ala Glu
        275                 280                 285

Glu Trp Phe Lys Cys Arg Tyr Ala Lys Leu Thr Glu Ala Ala Glu Gln
    290                 295                 300

Asn Lys Glu Ala Ile Arg Ser Ala Lys Glu Glu Ile Ala Glu Tyr Arg
305                 310                 315                 320

Arg Gln Leu Gln Ser Lys Ser Ile Glu Leu Glu Ser Val Arg Gly Thr
                325                 330                 335
```

-continued

```
Lys Glu Ser Leu Glu Arg Gln Leu Ser Asp Ile Glu Arg His Asn
            340                 345                 350

His Asp Leu Ser Ser Tyr Gln Asp Thr Ile Gln Gln Leu Glu Asn Glu
            355                 360                 365

Leu Arg Gly Thr Lys Trp Glu Met Ala Arg His Leu Arg Glu Tyr Gln
            370                 375                 380

Asp Leu Leu Asn Val Lys Met Ala Leu Asp Ile Glu Ile Ala Ala Tyr
385                 390                 395                 400

Arg Lys Leu Leu Glu Gly Glu Glu Thr Arg Phe Ser Thr Phe Ala Gly
                405                 410                 415

Ser Ile Thr Gly Pro Leu Tyr Thr His Arg Pro Pro Ile Thr Ile Ser
                420                 425                 430

Ser Lys Ile Gln Lys Thr Lys Val Glu Ala Pro Lys Leu Lys Val Gln
                435                 440                 445

His Lys Phe Val Glu Glu Ile Ile Glu Glu Thr Lys Val Glu Asp Glu
            450                 455                 460

Lys Ser Glu Met Glu Glu Ala Leu Thr Ala Ile Thr Glu Glu Leu Ala
465                 470                 475                 480

Ala Ser Met Lys Glu Glu Lys Lys Glu Ala Ala Glu Lys Glu Glu
                485                 490                 495

Glu Pro Glu Ala Glu Glu Glu Val Ala Ala Lys Lys Ser Pro Val
                500                 505                 510

Lys Ala Thr Ala Pro Glu Val Lys Glu Glu Gly Glu Lys Glu Glu
                515                 520                 525

Glu Glu Gly Gln Glu Glu Glu Glu Asp Glu Gly Ala Lys Ser
            530                 535                 540

Asp Gln Ala Glu Glu Gly Gly Ser Glu Lys Glu Gly Ser Ser Glu Lys
545                 550                 555                 560

Glu Glu Gly Glu Gln Glu Glu Gly Glu Thr Glu Ala Glu Ala Glu Gly
                565                 570                 575

Glu Glu Ala Glu Ala Lys Glu Glu Lys Lys Val Glu Glu Lys Ser Glu
            580                 585                 590

Glu Val Ala Thr Lys Glu Glu Leu Val Ala Asp Ala Lys Val Glu Lys
                595                 600                 605

Pro Glu Lys Ala Lys Ser Pro Val Pro Lys Ser Pro Val Glu Glu Lys
            610                 615                 620

Gly Lys Ser Pro Val Pro Lys Ser Pro Val Glu Glu Lys Gly Lys Ser
625                 630                 635                 640

Pro Val Pro Lys Ser Pro Val Glu Glu Lys Gly Lys Ser Pro Val Pro
                645                 650                 655

Lys Ser Pro Val Glu Glu Lys Gly Lys Ser Pro Val Ser Lys Ser Pro
                660                 665                 670

Val Glu Glu Lys Ala Lys Ser Pro Val Pro Lys Ser Pro Val Glu Glu
            675                 680                 685

Ala Lys Ser Lys Ala Glu Val Gly Lys Gly Glu Gln Lys Glu Glu Glu
            690                 695                 700

Glu Lys Glu Val Lys Glu Ala Pro Lys Glu Glu Lys Val Glu Lys Lys
705                 710                 715                 720

Glu Glu Lys Pro Lys Asp Val Pro Glu Lys Lys Ala Glu Ser Pro
                725                 730                 735

Val Lys Glu Glu Ala Val Ala Glu Val Val Thr Ile Thr Lys Ser Val
                740                 745                 750
```

-continued

```
Lys Val His Leu Glu Lys Glu Thr Lys Glu Glu Gly Lys Pro Leu Gln
        755                 760                 765

Gln Glu Lys Glu Lys Glu Lys Ala Gly Gly Glu Gly Gly Ser Glu Glu
    770                 775                 780

Glu Gly Ser Asp Lys Gly Ala Lys Gly Ser Arg Lys Glu Asp Ile Ala
785                 790                 795                 800

Val Asn Gly Glu Val Glu Gly Lys Glu Val Glu Gln Glu Thr Lys
                805                 810                 815

Glu Lys Gly Ser Gly Arg Glu Glu Lys Gly Val Val Thr Asn Gly
    820                 825                 830

Leu Asp Leu Ser Pro Ala Asp Glu Lys Lys Gly Gly Asp Lys Ser Glu
    835                 840                 845

Glu Lys Val Val Val Thr Lys Thr Val Glu Lys Ile Thr Ser Glu Gly
    850                 855                 860

Gly Asp Gly Ala Thr Lys Tyr Ile Thr Lys Ser Val Thr Val Thr Gln
865                 870                 875                 880

Lys Val Glu Glu His Glu Thr Phe Glu Glu Lys Leu Val Ser Thr
                885                 890                 895

Lys Lys Val Glu Lys Val Thr Ser His Ala Ile Val Lys Glu Val Thr
    900                 905                 910

Gln Ser Asp
    915

<210> SEQ ID NO 10
<211> LENGTH: 2751
<212> TYPE: DNA
<213> ORGANISM: Homo sapiens

<400> SEQUENCE: 10
atgagctaca cgttggactc gctgggcaac ccgtccgcct accggcgggt aaccgagacc      60
cgctcgagct tcagccgcgt cagcggctcc ccgtccagtg gcttccgctc gcagtcgtgg     120
tcccgcggct cgcccagcac cgtgtcctcc tcctataagc gcagcatgct cgccccgcgc     180
ctcgcttaca gctcggccat gctcagctcc gccgagagca gccttgactt cagccagtcc     240
tcgtccctgc tcaacggcgg ctccggaccc ggcggcgact acaagctgtc ccgctccaac     300
gagaaggagc agctgcaggg gctgaacgac cgctttgccg gctacataga gaaggtgcac     360
tacctggagc agcagaataa ggagattgag gcggagatcc aggcgctgcg cagaagcag      420 gcctcgcacg cccagctggg cgacgcgtac gaccaggaga tccgcgagct cgcgccacc      480 ctggagatgg tgaaccacga gaaggctcag gtgcagctgg actcggacca cctggaggaa     540
gacatccacc ggctcaagga cgctttgag gaggaggcgc ggttgcggga cgacactgag     600
gcggccatcc gggcgctgcg caaagacatc gaggaggcgt cgctggtcaa ggtggagctg     660
gacaagaagg tgcagtcgct gcaggatgag gtggccttcc tgcggagcaa ccacgaggag     720
gaggtggccg accttctggc ccagatccag gcatcgcaca tcacggtgga cgcaaagac     780 tacctgaaga cagacatctc gacggcgctg aaggaaatcc gctcccagct cgaaagccac     840
tcagaccaga atatgcacca ggccgaagag tggttcaaat gccgctacgc caagctcacc     900
gaggcggccg agcagaacaa ggaggccatc cgctccgcca aggaagagat cgccgagtac     960
cggcgccagc tgcagtccaa gagcatcgag ctagagtcgg tgcgcggcac caaggagtcc    1020
ctggagcggc agctcagcga catcgaggag cgccacaacc acgacctcag cagctaccag    1080
gacaccatcc agcagctgga aaatgagctt cggggcacaa agtgggaaat ggctcgtcat    1140
```

-continued

```
ttgcgcgaat accaggacct cctcaacgtc aagatggctc tggatataga aatcgctgcg    1200
tacagaaaac tcctggaggg tgaagagact agatttagca catttgcagg aagcatcact    1260
gggccactgt atacacaccg accccccaatc acaatatcca gtaagattca gaaaaccaag    1320
gtggaagctc ccaagcttaa ggtccaacac aaatttgtcg aggagatcat agaggaaacc    1380
aaagtggagg atgagaagtc agaaatggaa gaggccctga cagccattac agaggaattg    1440
gccgcttcca tgaaggaaga aagaaagaa gcagcagaag aaaaggaaga ggaacccgaa    1500
gctgaagaag aagaagtagc tgccaaaaag tctccagtga agcaactgc acctgaagtt    1560
aaagaagagg aaggggaaaa ggaggaagaa gaaggccagg aagaagagga ggaagaagat    1620
gagggagcta agtcagacca agccgaagag ggaggatccg agaaggaagg ctctagtgaa    1680
aaagaggaag gtgagcagga agaaggaaaa acagaagctg aagctgaagg agaggaagcc    1740
gaagctaaag aggaaaagaa agtggaggaa aagagtgagg aagtggctac caaggaggag    1800
ctggtggcag atgccaaggt ggaaaagcca gaaaaagcca agtctcctgt gccaaaatca    1860
ccagtggaag agaaaggcaa gtctcctgtg cccaagtcac cagtggaaga gaaaggcaag    1920
tctcctgtgc ccaagtcacc agtggaagag aaaggcaagt ctcctgtgcc gaaatcacca    1980
gtggaagaga aaggcaagtc tcctgtgtca aaatcaccag tggaagagaa agccaaatct    2040
cctgtgccaa atcaccagt ggaagaggca agtcaaaag cagaagtggg aaaggtgaa    2100
cagaaagagg aagaagaaaa ggaagtcaag gaagctccca aggaagagaa ggtagagaaa    2160
aaggaagaga accaaaagga tgtgccagag aagaagaaag ctgagtcccc tgtaaaggag    2220
gaagctgtgg cagaggtggt caccatcacc aaatcggtaa aggtgcactt ggagaaagag    2280
accaaagaag agggggaagcc actgcagcag gagaaagaga aggagaaagc gggaggagag    2340
ggaggaagtg aggaggaagg gagtgataaa ggtgccaagg gatccaggaa ggaagacata    2400
gctgtcaatg gggaggtaga aggaaagag gaggtagagc aggagaccaa ggaaaaggc    2460
agtggagggg aagaggagaa aggcgttgtc accaatggcc tagacttgag cccagcagat    2520
gaaaagaagg gggtgataa agtgaggag aaagtggtgg tgaccaaaac ggtagaaaa    2580
atcaccagtg agggggaga tggtgctacc aaatacatca ctaaatctgt aaccgtcact    2640
caaaaggttg aagagcatga agagaccttt gaggagaaac tagtgtctac taaaaaggta    2700
gaaaagtca cttcacacgc catagtaaag gaagtcaccc agagtgacta a            2751
```

<210> SEQ ID NO 11
<211> LENGTH: 848
<212> TYPE: PRT
<213> ORGANISM: Mus musculus

<400> SEQUENCE: 11

```
Ser Tyr Thr Leu Asp Ser Leu Gly Asn Pro Ser Ala Tyr Arg Arg Val
  1               5                  10                  15

Pro Thr Glu Thr Arg Ser Ser Phe Ser Arg Val Ser Gly Ser Pro Ser
                 20                  25                  30

Ser Gly Phe Arg Ser Gln Ser Trp Ser Arg Gly Ser Pro Ser Thr Val
             35                  40                  45

Ser Ser Ser Tyr Thr Arg Ser Ala Val Ala Pro Arg Leu Ala Tyr Ser
         50                  55                  60

Ser Ala Met Leu Ser Ser Ala Glu Ser Ser Leu Asp Phe Ser Gln Ser
 65                  70                  75                  80

Ser Ser Leu Leu Asn Gly Gly Ser Gly Gly Asp Tyr Lys Leu Ser Arg
                 85                  90                  95
```

```
Ser Asn Glu Lys Glu Gln Leu Gln Gly Leu Asn Asp Arg Phe Ala Gly
            100                 105                 110

Tyr Ile Glu Lys Val His Tyr Leu Glu Gln Gln Asn Lys Glu Ile Glu
        115                 120                 125

Ala Glu Ile Gln Ala Leu Arg Gln Lys Gln Ala Ser His Ala Gln Leu
    130                 135                 140

Gly Asp Ala Tyr Asp Gln Glu Ile Arg Glu Leu Arg Ala Thr Leu Glu
145                 150                 155                 160

Met Val Asn His Glu Lys Ala Gln Val Gln Leu Asp Ser Asp His Leu
                165                 170                 175

Glu Glu Asp Ile His Arg Leu Lys Glu Arg Phe Glu Glu Ala Arg
            180                 185                 190

Leu Arg Asp Asp Thr Glu Ala Ala Ile Arg Ala Leu Arg Lys Asp Ile
        195                 200                 205

Glu Glu Ser Ser Met Val Lys Val Glu Leu Asp Lys Lys Val Gln Ser
    210                 215                 220

Leu Gln Asp Glu Val Ala Phe Leu Arg Arg Asn His Glu Glu Glu Val
225                 230                 235                 240

Ala Asp Leu Leu Ala Gln Ile Gln Ala Ser His Ile Thr Val Glu Arg
                245                 250                 255

Lys Asp Tyr Leu Lys Thr Asp Ile Ser Thr Ala Leu Lys Glu Ile Arg
            260                 265                 270

Ser Gln Leu Glu Cys His Ser Asp Gln Asn Met His Gln Ala Glu Glu
        275                 280                 285

Trp Phe Lys Cys Arg Tyr Ala Lys Leu Thr Glu Ala Ala Glu Gln Asn
    290                 295                 300

Lys Glu Ala Ile Arg Ser Ala Lys Glu Glu Ile Ala Glu Tyr Arg Arg
305                 310                 315                 320

Gln Leu Gln Ser Lys Ser Ile Glu Leu Glu Ser Val Arg Gly Thr Lys
                325                 330                 335

Glu Ser Leu Glu Arg Gln Leu Ser Asp Ile Glu Glu Arg His Asn His
            340                 345                 350

Asp Leu Ser Ser Tyr Gln Asp Thr Ile Gln Gln Leu Glu Asn Glu Leu
        355                 360                 365

Arg Gly Thr Lys Trp Glu Met Ala Arg His Leu Arg Glu Tyr Gln Asp
    370                 375                 380

Leu Leu Asn Val Lys Met Ala Leu Asp Ile Glu Ile Ala Ala Tyr Arg
385                 390                 395                 400

Lys Leu Leu Glu Gly Glu Glu Thr Arg Phe Ser Thr Phe Ser Gly Ser
                405                 410                 415

Ile Thr Gly Pro Leu Tyr Thr His Arg Gln Pro Ser Val Thr Ile Ser
            420                 425                 430

Ser Lys Ile Gln Lys Thr Lys Val Glu Ala Pro Lys Leu Lys Val Gln
        435                 440                 445

His Lys Phe Val Glu Glu Ile Ile Glu Glu Thr Lys Val Glu Asp Glu
    450                 455                 460

Lys Ser Glu Met Glu Glu Thr Leu Thr Ala Ile Ala Glu Glu Leu Ala
465                 470                 475                 480

Ala Ser Ala Lys Glu Glu Lys Glu Glu Ala Glu Glu Lys Glu Glu Glu
                485                 490                 495

Pro Glu Ala Glu Lys Ser Pro Val Lys Ser Pro Glu Ala Lys Glu Glu
            500                 505                 510
```

-continued

| | | | | | | | | | | | |
|---|---|---|---|---|---|---|---|---|---|---|---|
|Glu|Glu|Glu|Gly|Glu|Lys|Glu|Glu|Glu|Gly|Gln|Glu|Glu|Glu|
| | |515| | |520| | | |525| | | |

Glu Glu Glu Asp Glu Gly Val Lys Ser Asp Gln Ala Glu Glu Gly Gly
              530                 535                 540

Ser Glu Lys Glu Gly Ser Ser Glu Lys Asp Glu Gly Glu Gln Glu Glu
545                 550                 555                 560

Glu Glu Gly Glu Thr Glu Ala Glu Gly Glu Gly Glu Ala Glu Ala
              565                 570                 575

Lys Glu Glu Lys Lys Ile Glu Gly Lys Val Glu Glu Val Ala Val Lys
              580                 585                 590

Glu Glu Ile Lys Val Glu Lys Pro Glu Lys Ala Lys Ser Pro Met Pro
              595                 600                 605

Lys Ser Pro Val Glu Glu Val Lys Pro Lys Pro Glu Ala Lys Ala Gly
610                 615                 620

Lys Gly Glu Gln Lys Glu Glu Lys Val Glu Glu Lys Lys Glu
625                 630                 635                 640

Val Thr Lys Glu Ser Pro Lys Glu Glu Lys Val Glu Lys Lys Glu Glu
              645                 650                 655

Lys Pro Lys Asp Val Ala Asp Lys Lys Ala Glu Ser Pro Val Lys
              660                 665                 670

Glu Lys Ala Val Glu Glu Val Ile Thr Ile Ser Lys Ser Val Lys Val
              675                 680                 685

Ser Leu Glu Lys Asp Thr Lys Glu Glu Lys Pro Gln Pro Gln Glu Lys
              690                 695                 700

Val Lys Glu Lys Ala Glu Glu Gly Gly Ser Glu Glu Gly Ser
705                 710                 715                 720

Asp Arg Ser Pro Gln Glu Ser Lys Lys Glu Asp Ile Ala Ile Asn Gly
              725                 730                 735

Glu Val Glu Gly Lys Glu Glu Glu Gln Glu Thr Gln Glu Lys Gly
              740                 745                 750

Ser Gly Arg Glu Glu Glu Lys Gly Val Val Thr Asn Gly Leu Asp Val
              755                 760                 765

Ser Pro Ala Glu Glu Lys Lys Gly Glu Asp Ser Ser Asp Asp Lys Val
770                 775                 780

Val Val Thr Lys Lys Val Glu Lys Ile Thr Ser Glu Gly Gly Asp Gly
785                 790                 795                 800

Ala Thr Lys Tyr Ile Thr Lys Ser Val Thr Val Thr Gln Lys Val Glu
              805                 810                 815

Glu His Glu Glu Thr Phe Glu Glu Lys Leu Val Ser Thr Lys Lys Val
              820                 825                 830

Glu Lys Val Thr Ser His Ala Ile Val Lys Glu Val Thr Gln Gly Asp
              835                 840                 845

<210> SEQ ID NO 12
<211> LENGTH: 2550
<212> TYPE: DNA
<213> ORGANISM: Mus musculus

<400> SEQUENCE: 12
atgagctaca cgctggactc gctgggcaac ccgtccgcct accggcgcgt tccaaccgag      60
acccggtcca gcttcagccg cgtgagcggt tccccgtcca gcggcttccg ctcgcagtcc     120
tggtcccgcg gctcgcccag caccgtgtcc tcctcctaca cgcgcagcgc ggtcgcccg     180 cgtctcgcct acagctcggc tatgctcagc tcggccgaga gcagcctcga cttcagccag     240

-continued

```
tcctcgtcgc tgctcaacgg cggctccggc ggcgactaca aactgtcccg ctctaacgag      300
aaagagcagc tgcaggggct gaacgaccgc ttcgccggct acatcgagaa agtgcactac      360
ttggaacaac agaacaagga gatcgaagca gagatccagg cactgcggca gaagcaggcc      420
tcgcacgccc agctgggtga tgcttacgac caggagatcc gagagctgcg cgccaccctc      480
gagatggtga accacgagaa ggctcaagtg cagctggact ccgatcactt ggaggaagac      540
atccaccggc tcaaggagcg cttcgaggag gaggcgcggc tgcgggacga caccgaggct      600
gccattcgcg cgctgcgcaa agacatcgaa gagtcgtcga tggttaaggt ggagctggac      660
aagaaggtgc agtcgctgca ggatgaggtg gctttcctgc ggcgtaatca cgaagaggag      720
gtggccgacc tgctggctca gatccaggcg tcgcacatca cggtagagcg caaagattac      780
ctgaagacag acatctccac ggcgctgaag gagatccgct cccagctcga gtgtcactca      840
gaccagaaca tgcaccaggc cgaagagtgg ttcaaatgcc gctacgccaa gctcaccgag      900
gcggccgagc agaacaagga ggccattcgc tctgccaagg aagagatcgc cgagtaccgg      960
cgccagctgc agtccaagag catcgagctc gagtcggtgc gaggcactaa ggagtccctg     1020
gaacggcagc tcagcgacat cgaggagcgc cacaaccacg acctcagcag ctaccaggac     1080
accatccagc agttggaaaa tgaacttcgg ggaaccaagt gggaaatggc tcgtcatttg     1140
cgagaatacc aggatctcct taacgtcaag atggccctgg acatcgagat cgccgcgtac     1200
aggaaactcc tagaggggga agagaccaga tttagcacat tttcaggaag catcaccggg     1260
cctctgtaca cacaccgaca gccctcagtc acaatatcca gtaagattca gaagaccaaa     1320
gtcgaggccc ccaagctcaa ggtccaacac aaatttgtgg aggagatcat cgaagaaact     1380
aaagtggaag atgagaagtc agaaatggaa gaaaccctca cagccatcgc agaggagttg     1440
gcagcctccg ccaaagagga gaaggaagag gccgaagaaa aggaggagga accagaagcc     1500
gaaaagtctc ccgtgaagtc tcctgaggct aaggaagagg aggaggaagg ggaaaaggag     1560
gaagaagagg aaggccagga ggaagaagag gaggaagatg aaggtgtcaa gtcagaccag     1620
gcagaagagg ggggatctga gaaggaaggc tccagtgaaa aagatgaagg tgagcaggaa     1680
gaagaagaag gagaaaccga ggcagaaggt gaaggagagg aagcagaagc taaggaggaa     1740
aagaaaattg agggaaaggt tgaggaagtg gctgtcaagg aggaaatcaa ggtcgagaag     1800
cctgagaaag ccaaatcccc tatgcccaaa tcacccgtgg aagaagtaaa gccaaaacca     1860
gaggccaagg ccgggaaggg tgagcagaag gaggaagaga agttgaggga agagaagaag     1920
gaagtcacca agaatcacc caaggaagag aaggtggaga aaaggagga gaagccaaaa      1980 gatgttgcag ataaaaagaa ggccgagtcc ccggtgaaag agaaggctgt ggaggaggtg     2040
atcaccatca gcaagtcggt aaaggtgagc ctggagaaag acaccaaaga ggagaagccg     2100
cagccgcagg agaaggtgaa ggagaaggca gaggaggagg ggggcagtga ggaggaaggg     2160
agtgaccgta gcccgcagga gtccaagaag gaagacatag ctatcaatgg ggaggtggaa     2220
ggaaaagagg aggaggagca ggaaactcag gagaagggca gtgggcggga ggaggagaaa     2280
ggggtggtca ctaatggctt agatgtgagc cctgcagagg agaagaaagg agaggatagc     2340
agtgatgata aagtggtggt caccaagaag gtagaaaaga tcaccagcga gggaggcgat     2400
ggtgctacca aatacatcac caaatctgta accgtcactc aaaaggttga agagcatgag     2460
gagacctttg aggagaagct ggtctcaact aaaaaggtag aaaaggtcac ttcacacgcc     2520
atagtcaagg aagtcaccca gggtgactaa                                      2550
```

<210> SEQ ID NO 13
<211> LENGTH: 845
<212> TYPE: PRT
<213> ORGANISM: Rattus Norvegicus

<400> SEQUENCE: 13

| | | | | | | | | | | | | | | |
|---|---|---|---|---|---|---|---|---|---|---|---|---|---|---|
| Ser | Tyr | Thr | Leu | Asp | Ser | Leu | Gly | Asn | Pro | Ser | Ala | Tyr | Arg | Arg | Val |
| 1 | | | | 5 | | | | | 10 | | | | | 15 | |
| Pro | Thr | Glu | Thr | Arg | Ser | Ser | Phe | Ser | Arg | Val | Ser | Gly | Ser | Pro | Ser |
| | | | 20 | | | | | 25 | | | | | 30 | | |
| Ser | Gly | Phe | Arg | Ser | Gln | Ser | Trp | Ser | Arg | Gly | Ser | Pro | Ser | Thr | Val |
| | | 35 | | | | | 40 | | | | | 45 | | | |
| Ser | Ser | Ser | Tyr | Lys | Arg | Ser | Ala | Leu | Ala | Pro | Arg | Leu | Ala | Tyr | Ser |
| | 50 | | | | | 55 | | | | | 60 | | | | |
| Ser | Ala | Met | Leu | Ser | Ser | Ala | Glu | Ser | Ser | Leu | Asp | Phe | Ser | Gln | Ser |
| 65 | | | | | 70 | | | | | 75 | | | | | 80 |
| Ser | Ser | Leu | Leu | Asn | Gly | Gly | Ser | Gly | Gly | Asp | Tyr | Lys | Leu | Ser | Arg |
| | | | | 85 | | | | | 90 | | | | | 95 | |
| Ser | Asn | Glu | Lys | Glu | Gln | Leu | Gln | Gly | Leu | Asn | Asp | Arg | Phe | Ala | Gly |
| | | | 100 | | | | | 105 | | | | | 110 | | |
| Tyr | Ile | Glu | Lys | Val | His | Tyr | Leu | Glu | Gln | Gln | Asn | Lys | Glu | Ile | Glu |
| | | 115 | | | | | 120 | | | | | 125 | | | |
| Ala | Glu | Ile | His | Ala | Leu | Arg | Gln | Lys | Gln | Ala | Ser | His | Ala | Gln | Leu |
| | 130 | | | | | 135 | | | | | 140 | | | | |
| Gly | Asp | Ala | Tyr | Asp | Gln | Glu | Ile | Arg | Glu | Leu | Arg | Ala | Thr | Leu | Glu |
| 145 | | | | | 150 | | | | | 155 | | | | | 160 |
| Met | Val | Asn | His | Glu | Lys | Ala | Gln | Val | Gln | Leu | Asp | Ser | Asp | His | Leu |
| | | | | 165 | | | | | 170 | | | | | 175 | |
| Glu | Glu | Asp | Ile | His | Arg | Leu | Lys | Glu | Arg | Phe | Glu | Glu | Glu | Ala | Arg |
| | | | 180 | | | | | 185 | | | | | 190 | | |
| Leu | Arg | Asp | Asp | Thr | Glu | Ala | Ala | Ile | Arg | Ala | Val | Arg | Lys | Asp | Ile |
| | | 195 | | | | | 200 | | | | | 205 | | | |
| Glu | Glu | Ser | Ser | Met | Val | Lys | Val | Glu | Leu | Asp | Lys | Lys | Val | Gln | Ser |
| | 210 | | | | | 215 | | | | | 220 | | | | |
| Leu | Gln | Asp | Glu | Val | Ala | Phe | Leu | Arg | Ser | Asn | His | Glu | Glu | Glu | Val |
| 225 | | | | | 230 | | | | | 235 | | | | | 240 |
| Ala | Asp | Leu | Leu | Ala | Gln | Ile | Gln | Ala | Ser | His | Ile | Thr | Val | Glu | Arg |
| | | | | 245 | | | | | 250 | | | | | 255 | |
| Lys | Asp | Tyr | Leu | Lys | Thr | Asp | Ile | Ser | Thr | Ala | Leu | Lys | Glu | Ile | Arg |
| | | | 260 | | | | | 265 | | | | | 270 | | |
| Ser | Gln | Leu | Glu | Cys | His | Ser | Asp | Gln | Asn | Met | His | Gln | Ala | Glu | Glu |
| | | 275 | | | | | 280 | | | | | 285 | | | |
| Trp | Phe | Lys | Cys | Arg | Tyr | Ala | Lys | Leu | Thr | Glu | Ala | Ala | Glu | Gln | Asn |
| | 290 | | | | | 295 | | | | | 300 | | | | |
| Lys | Glu | Ala | Ile | Arg | Ser | Ala | Lys | Glu | Glu | Ile | Ala | Glu | Tyr | Arg | Arg |
| 305 | | | | | 310 | | | | | 315 | | | | | 320 |
| Gln | Leu | Gln | Ser | Lys | Ser | Ile | Glu | Leu | Glu | Ser | Val | Arg | Gly | Thr | Lys |
| | | | | 325 | | | | | 330 | | | | | 335 | |
| Glu | Ser | Leu | Glu | Arg | Gln | Leu | Ser | Asp | Ile | Glu | Glu | Arg | His | Asn | His |
| | | | 340 | | | | | 345 | | | | | 350 | | |
| Asp | Leu | Ser | Ser | Tyr | Gln | Asp | Thr | Ile | Gln | Gln | Leu | Glu | Asn | Glu | Leu |
| | | 355 | | | | | 360 | | | | | 365 | | | |
| Arg | Gly | Thr | Lys | Trp | Glu | Met | Ala | Arg | His | Leu | Arg | Glu | Tyr | Gln | Asp |
| | 370 | | | | | 375 | | | | | 380 | | | | |

-continued

```
Leu Leu Asn Val Lys Met Ala Leu Asp Ile Glu Ile Ala Ala Tyr Arg
385                 390                 395                 400

Lys Leu Leu Glu Gly Glu Thr Arg Phe Ser Thr Phe Ser Gly Ser
            405                 410                 415

Ile Thr Gly Pro Leu Tyr Thr His Arg Gln Pro Ser Val Thr Ile Ser
            420                 425                 430

Ser Lys Ile Gln Lys Thr Lys Val Glu Ala Pro Lys Leu Lys Val Gln
            435                 440                 445

His Lys Phe Val Glu Glu Ile Ile Glu Thr Lys Val Glu Asp Glu
    450                 455                 460

Lys Ser Glu Met Glu Asp Ala Leu Thr Val Ile Ala Glu Glu Leu Ala
465                 470                 475                 480

Ala Ser Ala Lys Glu Glu Lys Glu Ala Glu Glu Lys Glu Glu
            485                 490                 495

Pro Glu Val Glu Lys Ser Pro Val Lys Ser Pro Glu Ala Lys Glu Glu
            500                 505                 510

Glu Glu Gly Glu Lys Glu Glu Glu Glu Gly Gln Glu Glu Glu
            515                 520                 525

Glu Glu Asp Glu Gly Val Lys Ser Asp Gln Ala Glu Glu Gly Gly Ser
    530                 535                 540

Glu Lys Glu Gly Ser Ser Glu Lys Asp Glu Gly Glu Gln Glu Glu Glu
545                 550                 555                 560

Gly Glu Thr Glu Ala Glu Gly Glu Gly Glu Glu Ala Glu Ala Lys Glu
            565                 570                 575

Glu Lys Lys Thr Glu Gly Lys Val Glu Glu Met Ala Ile Lys Glu Glu
            580                 585                 590

Ile Lys Val Glu Lys Pro Glu Lys Ala Lys Ser Pro Val Pro Lys Ser
    595                 600                 605

Pro Val Glu Glu Val Lys Pro Lys Pro Glu Ala Lys Ala Gly Lys Asp
    610                 615                 620

Glu Gln Lys Glu Glu Glu Lys Val Glu Lys Lys Glu Val Ala Lys
625                 630                 635                 640

Glu Ser Pro Lys Glu Glu Lys Val Glu Lys Lys Glu Glu Lys Pro Lys
            645                 650                 655

Asp Val Pro Asp Lys Lys Lys Ala Glu Ser Pro Val Lys Glu Lys Ala
    660                 665                 670

Val Glu Glu Met Ile Thr Ile Thr Lys Ser Val Lys Val Ser Leu Glu
    675                 680                 685

Lys Asp Thr Lys Glu Glu Lys Pro Gln Gln Gln Glu Lys Val Lys Glu
    690                 695                 700

Lys Ala Glu Glu Glu Gly Gly Ser Glu Glu Val Gly Asp Lys Ser
705                 710                 715                 720

Pro Gln Glu Ser Lys Lys Glu Asp Ile Ala Ile Asn Gly Glu Val Glu
            725                 730                 735

Gly Lys Glu Glu Glu Glu Gln Glu Thr Gln Glu Lys Gly Ser Gly Gln
            740                 745                 750

Glu Glu Glu Lys Gly Val Val Thr Asn Gly Leu Asp Val Ser Pro Ala
            755                 760                 765

Glu Glu Lys Lys Gly Glu Asp Arg Ser Asp Lys Val Val Thr
    770                 775                 780

Lys Lys Val Glu Lys Ile Thr Ser Glu Gly Gly Asp Gly Ala Thr Lys
785                 790                 795                 800

Tyr Ile Thr Lys Ser Val Thr Val Thr Gln Lys Val Glu Glu His Glu
```

|   |   | 805 |   |   | 810 |   |   | 815 |   |   |
|---|---|---|---|---|---|---|---|---|---|---|
| Glu | Thr | Phe | Glu | Glu | Lys | Leu | Val | Ser | Thr | Lys | Lys | Val | Glu | Lys | Val |
|   |   | 820 |   |   | 825 |   |   | 830 |   |   |
| Thr | Ser | His | Ala | Ile | Val | Lys | Glu | Val | Thr | Gln | Gly | Asp |
|   |   | 835 |   |   | 840 |   |   | 845 |   |   |

<210> SEQ ID NO 14
<211> LENGTH: 2538
<212> TYPE: DNA
<213> ORGANISM: Rattus norvegicus

<400> SEQUENCE: 14

| atgagctaca cgctggactc gctgggcaac ccgtccgcct accggcgcgt caccgagacc | 60 |
| ccgtccagct tcagtcgtgt gagcggttcc ccgtccagcg gcttccgctc gcagtcctgg | 120 |
| tcccgcggct cgcccagcac cgtgtcctcc tcctacaagc gcagcgcgct cgccccgcgc | 180 |
| ctcgcctaca gctcggctat gctcagctcg gccgagagca gcctcgactt cagccagtcc | 240 |
| tcttcgctgc ttaacggcgg ctccggcggc gactacaagc tgtcccgctc aaacgagaaa | 300 |
| gagcagctgc aggggctgaa cgaccgtttc gccggctaca tcgagaaagt gcactacttg | 360 |
| gaacaacaga acaaggagat cgaggcagag atccacgcgc tgcggcagaa gcaggcctcg | 420 |
| cacgcccagc tgggtgacgc ttacgaccag gagatccgag agctgcgcgc caccctggag | 480 |
| atggtgaatc acgagaaggc tcaagtgcag ctggactctg atcacttgga ggaagacatc | 540 |
| caccggctca aggagcgctt cgaggaggag gcgcggctgc gggacgacac cgaggctgcc | 600 |
| atccgggcgc tgcgcaaaga catagaggag tcgtcgatgg ttaaggtgga gctggacaag | 660 |
| aaggtgcagt cgctgcagga tgaggtggcc ttcctgcgga gcaatcacga agaggaggtg | 720 |
| gccgacctgc tggcccagat ccaggcgtcg cacatcaccg tagagcgcaa agactacctg | 780 |
| aagacagaca tctccacggc gctgaaagag atccgctccc agctcgagtg tcactccgac | 840 |
| cagaacatgc accaggccga agagtggttc aaatgccgct acgccaagct caccgaggcg | 900 |
| gccgagcaga acaaggaggc catccgctcc gctaaagaag atcgccga gtaccggcgc | 960 |
| cagctgcagt ccaagagcat tgagctcgag tcggtgcgag gcactaagga gtccctggaa | 1020 |
| cggcagctca gcgacatcga ggagcgccac aaccacgacc tcagcagcta ccaggacacc | 1080 |
| atccagcagc tggaaaatga gcttcgggga acaaagtggg aaatggctcg tcatttgcga | 1140 |
| gaataccagg atctccttaa cgtcaagatg gctctggaca tcgagatcgc cgcatataag | 1200 |
| aaactactgg agggtgaaga gaccagattt agcacatttt caggaagcat cactgggcct | 1260 |
| ctgtacacac accgacagcc ctcagtcaca atatccagta agattcagaa gaccaaagtc | 1320 |
| gaggccccca agctcaaggt ccaacacaaa tttgtggagg gatcattga ggagactaaa | 1380 |
| gtggaagatg agaagtcaga atggaagac gccctcacag tcattgcaga ggaattggca | 1440 |
| gcctctgcca agaggagaa agaagaggca aagaaaagg aagaggaacc ggaagttgaa | 1500 |
| aagtctcccg tgaagtctcc tgaggctaag gagaggagg aagggaaaa ggaggaagaa | 1560 |
| gaggaaggcc aagaggaaga agaggaggaa gatgaaggtg tcaagtcaga ccaggcagaa | 1620 |
| gagggaggat ctgagaagga aggctcgagt gaaaaggatg aaggtgagca agaagaagaa | 1680 |
| gggaaactg aggcagaagg tgaaggagag gagcagaag ctaaggagga aaagaaaaca | 1740 |
| gagggaaagg tcgaggaaat ggctatcaag gaggaaatca aggtcgagaa gcccgagaaa | 1800 |
| gccaagtccc ctgtgccaaa atcacccgtg gaagaagtaa agccaaaacc agaagccaaa | 1860 |
| gccggaaagg atgagcagaa ggaggaagag aaagttgagg agaagaagga ggtagccaag | 1920 |

-continued

```
gaatcaccca aggaagagaa ggtggagaaa aaggaggaga agccaaaaga tgtcccagat      1980
aaaaagaagg ctgagtcccc agtgaaagaa aaggccgtag aggaaatgat caccattact      2040
aagtcggtaa aggtgagcct ggagaaagac accaaagagg agaagcctca gcagcaggag      2100
aaggtgaagg agaaggcaga ggaggagggg ggtagtgagg aggaagtggg tgacaaaagc      2160
ccgcaagaat ccaagaagga agacatagct atcaatgggg aggtggaagg aaaagaggag      2220
gaggagcagg aaactcagga agggcagt gggcaagagg aggagaaagg ggtggtcact         2280
aatggcttag atgtgagccc tgcggaggaa agaaagggg aggatagaag tgatgacaaa       2340
gtggtggtga ccaagaaggt agaaaaaatc accagcgagg gaggcgatgg tgctaccaaa      2400
tacatcacca aatctgttac tgtcactcaa aaggttgaag agcatgagga gacctttgag      2460
gagaagctgg tgtcaactaa aaaggtagaa aaggtcactt cacatgccat agtcaaggaa      2520
gtcacccagg gtgactaa                                                    2538
```

<210> SEQ ID NO 15
<211> LENGTH: 644
<212> TYPE: PRT
<213> ORGANISM: Oryctolagus cuniculus

<400> SEQUENCE: 15

```
Val Lys Val Glu Leu Asp Lys Lys Val Gln Ser Leu Gln Asp Glu Val
  1               5                  10                  15

Ala Phe Leu Arg Thr Asn His Glu Glu Glu Val Ala Asp Leu Leu Ala
             20                  25                  30

Gln Ile Gln Ala Ser His Ile Thr Val Glu Arg Lys Asp Tyr Leu Lys
         35                  40                  45

Thr Asp Ile Ser Ser Ala Leu Lys Glu Ile Arg Ser Gln Leu Glu Cys
     50                  55                  60

His Ser Asp Gln Asn Met His Gln Ala Glu Glu Trp Phe Lys Cys Arg
 65                  70                  75                  80

Tyr Ala Lys Leu Thr Glu Ala Ala Glu Gln Asn Lys Glu Ala Ile Arg
                 85                  90                  95

Ser Ala Lys Glu Glu Ile Ala Glu Tyr Arg Arg Gln Leu Gln Ser Lys
            100                 105                 110

Ser Ile Glu Leu Glu Ser Val Ala Trp His Lys Glu Ser Leu Glu Arg
        115                 120                 125

His Val Ser Asp Ile Glu Glu Arg His Asn His Asp Leu Ser Ser Tyr
    130                 135                 140

Gln Asp Thr Ile Gln Gln Leu Glu Asn Glu Leu Arg Gly Thr Lys Trp
145                 150                 155                 160

Glu Met Ala Arg His Leu Arg Glu Tyr Gln Asp Leu Leu Asn Val Lys
                165                 170                 175

Met Ala Leu Asp Ile Glu Ile Ala Ala Tyr Arg Lys Leu Leu Glu Gly
            180                 185                 190

Glu Glu Thr Arg Phe Ser Thr Phe Ser Gly Ser Ile Thr Gly Pro Leu
        195                 200                 205

Tyr Thr His Arg Gln Pro Ser Val Thr Ile Ser Ser Lys Ile Gln Lys
    210                 215                 220

Thr Lys Val Glu Ala Pro Lys Leu Lys Val Gln His Lys Phe Val Glu
225                 230                 235                 240

Glu Ile Ile Glu Glu Thr Lys Val Glu Asp Glu Lys Ser Glu Met Glu
                245                 250                 255
```

```
Asp Ala Leu Thr Ala Ile Ala Glu Glu Leu Ala Val Ser Val Lys Glu
            260                 265                 270
Glu Glu Lys Glu Glu Glu Ala Glu Gly Lys Glu Glu Gln Glu Ala
        275                 280                 285
Glu Glu Glu Val Ala Ala Lys Lys Ser Pro Val Lys Ala Thr Thr
        290                 295                 300
Pro Glu Ile Lys Glu Glu Gly Glu Lys Glu Glu Gly Gln Glu
305                 310                 315                 320
Glu Glu Glu Glu Glu Asp Glu Gly Val Lys Ser Asp Gln Ala Glu
                325                 330                 335
Glu Gly Gly Ser Glu Lys Glu Gly Ser Ser Lys Asn Glu Gly Gln
                340                 345                 350
Glu Glu Gly Glu Thr Glu Ala Glu Gly Glu Val Glu Glu Ala Glu Ala
                355                 360                 365
Lys Glu Glu Lys Lys Thr Glu Glu Lys Ser Glu Glu Val Ala Ala Lys
    370                 375                 380
Glu Glu Pro Val Thr Glu Ala Lys Val Gly Lys Pro Glu Lys Ala Lys
385                 390                 395                 400
Ser Pro Val Pro Lys Ser Pro Val Glu Glu Val Lys Pro Lys Ala Glu
                405                 410                 415
Ala Thr Ala Gly Lys Gly Glu Gln Lys Glu Glu Glu Lys Val Glu
                420                 425                 430
Glu Glu Lys Lys Lys Ala Ala Lys Glu Ser Pro Lys Glu Glu Lys Val
            435                 440                 445
Glu Lys Lys Glu Glu Lys Pro Lys Asp Val Pro Lys Lys Ala Glu
        450                 455                 460
Ser Pro Val Lys Glu Glu Ala Glu Glu Ala Ala Thr Ile Thr Lys
465                 470                 475                 480
Pro Thr Lys Val Gly Leu Glu Lys Glu Thr Lys Glu Gly Glu Lys Pro
                485                 490                 495
Leu Gln Gln Glu Lys Glu Lys Glu Lys Ala Gly Glu Gly Gly Ser
                500                 505                 510
Glu Glu Glu Gly Ser Asp Gln Gly Ser Lys Arg Ala Lys Lys Glu Asp
            515                 520                 525
Ile Ala Val Asn Gly Glu Gly Gly Lys Glu Glu Glu Pro Glu
        530                 535                 540
Thr Lys Glu Lys Gly Ser Gly Arg Glu Glu Lys Gly Val Thr
545                 550                 555                 560
Asn Gly Leu Asp Leu Ser Pro Ala Asp Glu Lys Lys Gly Gly Asp Arg
                565                 570                 575
Ser Glu Glu Lys Val Val Val Thr Lys Lys Val Glu Lys Ile Thr Thr
                580                 585                 590
Glu Gly Gly Asp Gly Ala Thr Lys Tyr Ile Thr Lys Ser Val Thr Ala
                595                 600                 605
Gln Lys Val Glu Glu His Glu Glu Thr Phe Glu Glu Lys Leu Val Ser
        610                 615                 620
Thr Lys Lys Val Glu Lys Val Thr Ser His Ala Ile Val Lys Glu Val
625                 630                 635                 640

Thr Gln Ser Asp

<210> SEQ ID NO 16
<211> LENGTH: 1938
<212> TYPE: DNA
<213> ORGANISM: Oryctolagus cuniculus
```

<400> SEQUENCE: 16

```
tggtcaaggt ggagctggac aagaaggtcc agtcgctgca ggatgaggtg gccttcctgc      60
ggacgaacca cgaggaggag gtagcggacc tgctggccca gatccaggcg tcgcacatca     120
cggtggagcg caaagactac ctgaagacgg acatctcgtc ggcgctgaag gagatccgct     180
cccagctcga gtgccactcc gaccagaaca tgcatcaggc cgaagagtgg tttaagtgcc     240
gctacgccaa gctcaccgaa gccgccgagc agaacaagga ggccatccgc tccgccaagg     300
aagagatcgc cgagtaccgg cgccagctgc agtccaagag catcgagctc gagtcggtcg     360
cgtggcacaa ggagtccctg gagcggcacg tcagcgacat cgaggagcgc cacaaccacg     420
acctcagcag ctaccaggac accattcagc agctggaaaa tgagcttcgg ggaacgaagt     480
gggaaatggc ccgccacttg cgagagtacc aggatctcct caatgtcaag atggctctgg     540
atatcgagat cgcagcctac agaaaactcc tggagggtga agagaccaga ttcagcacat     600
tttcaggaag catcactggg ccactgtata cacaccgaca gccctcagtc accatatcca     660
gtaagattca gaagacaaag gtggaagctc ccaagctcaa agtccaacac aaatttgttg     720
aggagatcat agaggaaacc aaagtggagg atgagaagtc agaaatggaa gatgcactga     780
cagccattgc agaggaactg gccgtgtctg tgaaggaaga ggagaaggaa gaagaggcag     840
aaggaaagga agaggagcaa gaagctgaag aagaagttgc agctgccaag aagtctccag     900
tgaaggctac cacacccgag attaaagagg aagaagggga aaggaagaa gaaggccagg     960
aggaggaaga gaggaagaa gatgaaggtg ttaagtcaga ccaagctgaa gagggaggat    1020
cagagaagga aggctctagc aagaacgagg gtgagcagga agaaggagaa accgaggctg    1080
aaggtgaagt agaagaagca gaagccaagg aggaaaagaa aaccgaggag aagagtgaag    1140
aagtggctgc taaagaggag ccagtgacag aagccaaggt gggaaagcca gagaaagcca    1200
agtcccctgt gccaaaatca ccagtggaag aggtgaagcc aaaagctgaa gccacagcag    1260
ggaaagggga gcagaaagag gaagaagaga aggttgagga agaaaagaaa aaggcagcca    1320
aggaatctcc aaaggaagag aaggtggaga gaaggaggagaaaccaaaa gatgtgccaa    1380
agaagaaagc tgaatccccg gtaaaagagg aggccgcaga agaggctgcc accatcacca    1440
aacccacaaa ggtgggcttg gagaaagaga ccaaagaagg ggagaagccg ctgcagcagg    1500
agaaggaaaa ggagaaagca ggagaggagg gagggagtga ggaggaaggg agcgaccagg    1560
ggtcaaagag ggccaagaag gaagacatag cagtcaatgg ggagggcgaa gggaaagagg    1620
aggaagagcc ggagaccaag gaaaagggca gtgggcgaga agaggagaaa ggcgtcgtca    1680
ccaatgggtt agacctgagc ccagcagacg agaagaaggg gggtgacaga agcgaggaga    1740
aagtggtggt gaccaaaaag gtagaaaaaa tcaccactga gggggcgat ggtgctacca    1800
aatacatcac taaatctgta accgctcaaa aggtcgaaga gcatgaagag acctttgagg    1860
agaaactagt gtctactaaa aaggtagaaa aagtcacttc acacgccatt gtaaaggaag    1920
tcacccagag tgactaag                                                  1938
```

<210> SEQ ID NO 17
<211> LENGTH: 424
<212> TYPE: PRT
<213> ORGANISM: Enterobacteria phage M13

<400> SEQUENCE: 17

```
Met Lys Lys Leu Leu Phe Ala Ile Pro Leu Val Val Pro Phe Tyr Ser
 1               5                  10                  15
```

-continued

```
His Ser Ala Glu Thr Val Glu Ser Cys Leu Ala Lys Pro His Thr Glu
             20                  25                  30
Asn Ser Phe Thr Asn Val Trp Lys Asp Asp Lys Thr Leu Asp Arg Tyr
         35                  40                  45
Ala Asn Tyr Glu Gly Cys Leu Trp Asn Ala Thr Gly Val Val Val Cys
     50                  55                  60
Thr Gly Asp Glu Thr Gln Cys Tyr Gly Thr Trp Val Pro Ile Gly Leu
 65                  70                  75                  80
Ala Ile Pro Glu Asn Glu Gly Gly Ser Glu Gly Gly Ser Glu
                 85                  90                  95
Gly Gly Gly Ser Glu Gly Gly Thr Lys Pro Pro Glu Tyr Gly Asp
                100                 105                 110
Thr Pro Ile Pro Gly Tyr Thr Tyr Ile Asn Pro Leu Asp Gly Thr Tyr
                115                 120                 125
Pro Pro Gly Thr Glu Gln Asn Pro Ala Asn Pro Asn Pro Ser Leu Glu
                130                 135                 140
Glu Ser Gln Pro Leu Asn Thr Phe Met Phe Gln Asn Asn Arg Phe Arg
145                 150                 155                 160
Asn Arg Gln Gly Ala Leu Thr Val Tyr Thr Gly Thr Val Thr Gln Gly
                165                 170                 175
Thr Asp Pro Val Lys Thr Tyr Tyr Gln Tyr Thr Pro Val Ser Ser Lys
                180                 185                 190
Ala Met Tyr Asp Ala Tyr Trp Asn Gly Lys Phe Arg Asp Cys Ala Phe
                195                 200                 205
His Ser Gly Phe Asn Glu Asp Pro Phe Val Cys Glu Tyr Gln Gly Gln
                210                 215                 220
Ser Ser Asp Leu Pro Gln Pro Val Asn Ala Gly Gly Gly Ser Gly
225                 230                 235                 240
Gly Gly Ser Gly Gly Gly Ser Glu Gly Gly Ser Glu Gly Gly Gly
                245                 250                 255
Ser Glu Gly Gly Gly Ser Glu Gly Gly Ser Gly Gly Gly Ser Gly
                260                 265                 270
Ser Gly Asp Phe Asp Tyr Glu Lys Met Ala Asn Ala Asn Lys Gly Ala
                275                 280                 285
Met Thr Glu Asn Ala Asp Glu Asn Ala Leu Gln Ser Asp Ala Lys Gly
                290                 295                 300
Lys Leu Asp Ser Val Ala Thr Asp Tyr Gly Ala Ala Ile Asp Gly Phe
305                 310                 315                 320
Ile Gly Asp Val Ser Gly Leu Ala Asn Gly Asn Gly Ala Thr Gly Asp
                325                 330                 335
Phe Ala Gly Ser Asn Ser Gln Met Ala Gln Val Gly Asp Gly Asp Asn
                340                 345                 350
Ser Pro Leu Met Asn Asn Phe Arg Gln Tyr Leu Pro Ser Leu Pro Gln
                355                 360                 365
Ser Val Glu Cys Arg Pro Phe Val Phe Ser Ala Gly Lys Pro Tyr Glu
                370                 375                 380
Phe Ser Ile Asp Cys Asp Lys Ile Asn Leu Phe Arg Gly Val Phe Ala
385                 390                 395                 400
Phe Leu Leu Tyr Val Ala Thr Phe Met Tyr Val Phe Ser Thr Phe Ala
                405                 410                 415
Asn Ile Leu Arg Asn Lys Glu Ser
                420
```

<210> SEQ ID NO 18
<211> LENGTH: 1275
<212> TYPE: DNA
<213> ORGANISM: Enterobacteria phage M13

<400> SEQUENCE: 18

| | | | | | |
|---|---|---|---|---|---|
| atgaaaaaat | tattattcgc | aattcccttta | gttgttcctt | tctattctca | ctccgctgaa | 60 |
| actgttgaaa | gttgtttagc | aaaacccat | acagaaaatt | catttactaa | cgtctggaaa | 120 |
| gacgacaaaa | ctttagatcg | ttacgctaac | tatgagggtt | gtctgtggaa | tgctacaggc | 180 |
| gttgtagttt | gtactggtga | cgaaactcag | tgttacggta | catgggttcc | tattgggctt | 240 |
| gctatccctg | aaaatgaggg | tggtggctct | gagggtggcg | gttctgaggg | tggcggttct | 300 |
| gagggtggcg | gtactaaacc | tcctgagtac | ggtgatacac | ctattccggg | ctatacttat | 360 |
| atcaaccctc | tcgacggcac | ttatccgcct | ggtactgagc | aaaaccccgc | taatcctaat | 420 |
| ccttctcttg | aggagtctca | gcctcttaat | actttcatgt | ttcagaataa | taggttccga | 480 |
| aataggcagg | gggcattaac | tgtttatacg | ggcactgtta | ctcaaggcac | tgaccccgtt | 540 |
| aaaacttatt | accagtacac | tcctgtatca | tcaaaagcca | tgtatgacgc | ttactggaac | 600 |
| ggtaaattca | gagactgcgc | tttccattct | ggctttaatg | aggatccatt | cgtttgtgaa | 660 |
| tatcaaggcc | aatcgtctga | cctgcctcaa | cctcctgtca | atgctggcgg | cggctctggt | 720 |
| ggtggttctg | gtggcggctc | tgagggtggt | ggctctgagg | gtggcggttc | tgagggtggc | 780 |
| ggctctgagg | gaggcggttc | cggtggtggc | tctggttccg | gtgatttga | ttatgaaaag | 840 |
| atggcaaacg | ctaataaggg | ggctatgacc | gaaaatgccg | atgaaaacgc | gctacagtct | 900 |
| gacgctaaag | gcaaacttga | ttctgtcgct | actgattacg | gtgctgctat | cgatggtttc | 960 |
| attggtgacg | tttccggcct | tgctaatggt | aatggtgcta | ctggtgattt | tgctggctct | 1020 |
| aattcccaaa | tggctcaagt | cggtgacggt | gataattcac | ctttaatgaa | taatttccgt | 1080 |
| caatatttac | cttccctccc | tcaatcggtt | gaatgtcgcc | cttttgtctt | tagcgctggt | 1140 |
| aaaccatatg | aattttctat | tgattgtgac | aaaataaact | tattccgtgg | tgtctttgcg | 1200 |
| tttcttttat | atgttgccac | ctttatgtat | gtattttcta | cgtttgctaa | catactgcgt | 1260 |
| aataaggagt | cttaa | | | | | 1275 |

<210> SEQ ID NO 19
<211> LENGTH: 720
<212> TYPE: PRT
<213> ORGANISM: Saccharomyces cerevisiae

<400> SEQUENCE: 19

Met Ala Lys Arg Val Ala Asp Ala Gln Ile Gln Arg Glu Thr Tyr Asp
  1               5                  10                  15

Ser Asn Glu Ser Asp Asp Val Thr Pro Ser Thr Lys Val Ala Ser
                 20                  25                  30

Ser Ala Val Met Asn Arg Arg Lys Ile Ala Met Pro Lys Arg Met
         35                  40                  45

Ala Phe Lys Pro Phe Gly Ser Ala Lys Ser Asp Glu Thr Lys Gln Ala
     50                  55                  60

Ser Ser Phe Ser Phe Leu Asn Arg Ala Asp Gly Thr Gly Glu Ala Gln
 65                  70                  75                  80

Val Asp Asn Ser Pro Thr Thr Glu Ser Asn Ser Arg Leu Lys Ala Leu
                 85                  90                  95

Asn Leu Gln Phe Lys Ala Lys Val Asp Asp Leu Val Leu Gly Lys Pro

-continued

```
            100                 105                 110
Leu Ala Asp Leu Arg Pro Leu Phe Thr Arg Tyr Glu Leu Tyr Ile Lys
            115                 120                 125
Asn Ile Leu Glu Ala Pro Val Lys Ser Ile Glu Asn Pro Thr Gln Thr
            130                 135                 140
Lys Gly Asn Asp Ala Lys Pro Ala Lys Val Glu Asp Val Gln Lys Ser
145                 150                 155                 160
Ser Asp Ser Ser Ser Glu Asp Glu Val Lys Val Glu Gly Pro Lys Phe
                        165                 170                 175
Thr Ile Asp Ala Lys Pro Pro Ile Ser Asp Ser Val Phe Ser Phe Gly
                180                 185                 190
Pro Lys Lys Glu Asn Arg Lys Lys Asp Glu Ser Asp Ser Glu Asn Asp
            195                 200                 205
Ile Glu Ile Lys Gly Pro Glu Phe Lys Phe Ser Gly Thr Val Ser Ser
            210                 215                 220
Asp Val Phe Lys Leu Asn Pro Ser Thr Asp Lys Asn Glu Lys Lys Thr
225                 230                 235                 240
Glu Thr Asn Ala Lys Pro Phe Ser Phe Ser Ser Ala Thr Ser Thr Thr
                        245                 250                 255
Glu Gln Thr Lys Ser Lys Asn Pro Leu Ser Leu Thr Glu Ala Thr Lys
                260                 265                 270
Thr Asn Val Asp Asn Asn Ser Lys Ala Glu Ala Ser Phe Thr Phe Gly
            275                 280                 285
Thr Lys His Ala Ala Asp Ser Gln Asn Lys Pro Ser Phe Val Phe
            290                 295                 300
Gly Gln Ala Ala Ala Lys Pro Ser Leu Glu Lys Ser Ser Phe Thr Phe
305                 310                 315                 320
Gly Ser Thr Thr Ile Glu Lys Lys Asn Asp Glu Asn Ser Thr Ser Asn
                        325                 330                 335
Ser Lys Pro Glu Lys Ser Ser Asp Ser Asn Asp Ser Asn Pro Ser Phe
                340                 345                 350
Ser Phe Ser Ile Pro Ser Lys Asn Thr Pro Asp Ala Ser Lys Pro Ser
            355                 360                 365
Phe Ser Phe Gly Val Pro Asn Ser Ser Lys Asn Glu Thr Ser Lys Pro
            370                 375                 380
Val Phe Ser Phe Gly Ala Ala Thr Pro Ser Ala Lys Glu Ala Ser Gln
385                 390                 395                 400
Glu Asp Asp Asn Asn Val Glu Lys Pro Ser Ser Lys Pro Ala Phe
                        405                 410                 415
Asn Leu Ile Ser Asn Ala Gly Thr Glu Lys Glu Lys Glu Ser Lys Lys
                420                 425                 430
Asp Ser Lys Pro Ala Phe Ser Phe Gly Ile Ser Asn Gly Ser Glu Ser
            435                 440                 445
Lys Asp Ser Asp Lys Pro Ser Leu Pro Ser Ala Val Asp Gly Glu Asn
            450                 455                 460
Asp Lys Lys Glu Ala Thr Lys Pro Ala Phe Ser Phe Gly Ile Asn Thr
465                 470                 475                 480
Asn Thr Thr Lys Thr Ala Asp Thr Lys Ala Pro Thr Phe Thr Phe Gly
                        485                 490                 495
Ser Ser Ala Leu Ala Asp Asn Lys Glu Asp Val Lys Lys Pro Phe Ser
                500                 505                 510
Phe Gly Thr Ser Gln Pro Asn Asn Thr Pro Ser Phe Ser Phe Gly Lys
            515                 520                 525
```

```
Thr Thr Ala Asn Leu Pro Ala Asn Ser Ser Thr Ser Pro Ala Pro Ser
    530                 535                 540

Ile Pro Ser Thr Gly Phe Lys Phe Ser Leu Pro Phe Glu Gln Lys Gly
545                 550                 555                 560

Ser Gln Thr Thr Thr Asn Asp Ser Lys Glu Glu Ser Thr Thr Glu Ala
                565                 570                 575

Thr Gly Asn Glu Ser Gln Asp Ala Thr Lys Val Asp Ala Thr Pro Glu
            580                 585                 590

Glu Ser Lys Pro Ile Asn Leu Gln Asn Gly Glu Glu Asp Glu Val Ala
        595                 600                 605

Leu Phe Ser Gln Lys Ala Lys Leu Met Thr Phe Asn Ala Glu Thr Lys
    610                 615                 620

Ser Tyr Asp Ser Arg Gly Val Gly Glu Met Lys Leu Leu Lys Lys Lys
625                 630                 635                 640

Asp Asp Pro Ser Lys Val Arg Leu Leu Cys Arg Ser Asp Gly Met Gly
                645                 650                 655

Asn Val Leu Leu Asn Ala Thr Val Val Asp Ser Phe Lys Tyr Glu Pro
            660                 665                 670

Leu Ala Pro Gly Asn Asp Asn Leu Ile Lys Ala Pro Thr Val Ala Ala
        675                 680                 685

Asp Gly Lys Leu Val Thr Tyr Ile Val Lys Phe Lys Gln Lys Glu Glu
    690                 695                 700

Gly Arg Ser Phe Thr Lys Ala Ile Glu Asp Ala Lys Lys Glu Met Lys
705                 710                 715                 720

<210> SEQ ID NO 20
<211> LENGTH: 2163
<212> TYPE: DNA
<213> ORGANISM: Saccharomyces cerevisiae

<400> SEQUENCE: 20
atggccaaaa gagttgccga tgcgcaaata cagagagaaa cgtacgattc taacgagtct      60
gacgatgacg tgactccctc cactaaggtt gcgtcatctg ctgtgatgaa tagaagaaaa     120
attgccatgc caaagcgcag gatggcgttc aaacctttg gttctgcaaa atcggatgaa      180
accaagcagg ctagttcctt tagcttcctg aaccgggcgg acggcactgg agaagctcag     240
gttgataata gccctaccac agaaagcaat tccagactaa agcattgaa cctccagttc      300 aaggctaagg ttgatgactt agttctaggc aagccgttag cggacttgag gccccttttc     360
accaggtacg aattatacat aaagaatatc ttagaagctc ccgtgaaatt tatcgagaat     420
ccaacgcaga caagggaaa tgatgctaaa cctgccaaag tagaagatgt ccaaaaaagt      480
tccgattctt catctgaaga tgaggttaag gtggagggc ccaagttcac aatagatgct      540
aaaccgccta tttcagattc cgtttttctca tttggcccaa aaaagaaaa tcgcaagaaa     600 gatgaaagtg atagcgaaaa cgatatagaa tcaagggcc ctgaatttaa atttctgga      660 actgtatcaa gtgatgtatt taagctgaat ccaagcaccg ataaaaatga aagaaaacc     720 gagactaatg ctaaaccatt tcatttttct tcggccactt caactactga acaaacgaag    780
agtaaaaatc cccttcatt gacagaagct accaagacca atgtggacaa caacagtaaa     840
gccgaggctt ccttcacttt tggaacaaaa catgctgcgg attctcaaaa taataaacca     900
tcttttgtat ttggtcaagc agctgcaaaa ccatcgctag aaagagctc attcacgttt      960 ggttcaacaa caattgaaaa aaaaaatgac gaaaactcaa cctctaactc aaaacctgaa    1020
```

```
aagtctagtg atagcaatga ttcaaaccca tcttttcct tttccatacc cagtaagaat    1080
acacctgatg catctaagcc atcttttaat tttggggtcc caaactcttc caaaaacgaa    1140
acttcaaaac cggtattttc gtttggtgca gcaacaccat cggccaaaga agctagtcag    1200
gaagatgaca acaacaacgt tgaaaaacct tcctctaagc ctgccttcaa tttcatatct    1260
aacgctggta ccgagaaaga gaaggaaagt aaaaaggact caaagccagc ttttcattt    1320 ggcatatcaa acggaagtga aagcaaagac tctgacaaac cctctttacc ctctgcggtt    1380
gatggtgaaa atgacaagaa agaagcaaca aaacctgctt tttcgtttgg aataaataca    1440
aatactacta aaccgcgga tactaaagct ccaactttta catttggctc ctctgcactc    1500
gctgacaata aagaggatgt taagaaacct ttttcattcg gtacctccca gcctaataat    1560
actccatcct tctcattcgg aaaaacaaca gcaaacttgc ctgctaattc ttcaacatct    1620
cctgctccct ctataccatc gacggggttc aaattttctt tgccatttga caaaaaggt    1680 agtcaaacaa ctacaaatga tagcaaggaa gaatcaacaa cagaagcaac tggaaatgag    1740
tcgcaagatg caaccaaagt agatgctacc ccagaagaat caaagccaat aaacttgcaa    1800
aacggtgagg aagacgaagt ggctttattt tcgcaaaaag caaaattaat gacattcaat    1860
gctgaaacca atcgtacga ttcaagaggc gtaggcgaaa tgaagctttt gaagaaaaag    1920
gacgatcctt ctaaagtgcg cctactttgt aggtctgacg gtatgggtaa tgtattacta    1980
aatgcaactg ttgtagactc cttcaaatat gagcctttag ctcccggaaa tgataatctc    2040
attaaagctc ctactgttgc ggctgatggg aaacttgtaa cttatatcgt caagtttaag    2100
cagaaggaag aaggccgctc atttacgaaa gctattgaag atgctaaaaa agaaatgaaa    2160
taa                                                                  2163
```

<210> SEQ ID NO 21
<211> LENGTH: 860
<212> TYPE: PRT
<213> ORGANISM: Mus musculus

<400> SEQUENCE: 21

```
Met Ala Gly Leu Thr Ala Val Val Pro Gln Pro Gly Val Leu Leu Ile
 1               5                  10                  15

Leu Leu Asn Leu His Pro Ala Gln Pro Gly Gly Val Pro Gly
            20                  25                  30

Ala Val Pro Gly Gly Leu Pro Gly Gly Val Pro Gly Gly Val Tyr Tyr
        35                  40                  45

Pro Gly Ala Gly Ile Gly Gly Leu Gly Gly Gly Gly Ala Leu Gly
    50                  55                  60

Pro Gly Gly Lys Pro Pro Lys Pro Gly Ala Gly Leu Leu Gly Thr Phe
65                  70                  75                  80

Gly Ala Gly Pro Gly Gly Leu Gly Gly Ala Pro Gly Ala Gly Leu
                85                  90                  95

Gly Ala Phe Pro Ala Gly Thr Phe Pro Gly Ala Gly Ala Leu Val Pro
            100                 105                 110

Gly Gly Ala Ala Gly Ala Ala Ala Tyr Lys Ala Ala Ala Lys Ala
        115                 120                 125

Gly Ala Gly Leu Gly Gly Val Gly Gly Val Pro Gly Gly Val Gly Val
    130                 135                 140

Gly Gly Val Pro Gly Gly Val Gly Val Gly Gly Val Pro Gly Gly Val
145                 150                 155                 160

Gly Val Gly Gly Val Pro Gly Gly Val Gly Gly Ile Gly Gly Ile Gly
```

-continued

```
                165                 170                 175
Gly Leu Gly Val Ser Thr Gly Ala Val Pro Gln Val Gly Ala Gly
            180                 185                 190
Ile Gly Ala Gly Gly Lys Pro Gly Lys Val Pro Gly Val Gly Leu Pro
            195                 200                 205
Gly Val Tyr Pro Gly Gly Val Leu Pro Gly Thr Gly Ala Arg Phe Pro
            210                 215                 220
Gly Val Gly Val Leu Pro Gly Val Pro Thr Gly Thr Gly Val Lys Ala
225                 230                 235                 240
Lys Ala Pro Gly Gly Gly Ala Phe Ser Gly Ile Pro Gly Val Gly
            245                 250                 255
Pro Phe Gly Gly Gln Gln Pro Gly Val Pro Leu Gly Tyr Pro Ile Lys
            260                 265                 270
Ala Pro Lys Leu Pro Gly Gly Tyr Gly Leu Pro Tyr Thr Asn Gly Lys
            275                 280                 285
Leu Pro Tyr Gly Val Ala Gly Ala Gly Lys Ala Gly Tyr Pro Thr
            290                 295                 300
Gly Thr Gly Val Gly Ser Gln Ala Ala Ala Ala Ala Lys Ala Ala
305                 310                 315                 320
Lys Tyr Gly Ala Gly Gly Ala Gly Val Leu Pro Gly Val Gly Gly
            325                 330                 335
Gly Ile Pro Gly Gly Ala Gly Ala Ile Pro Gly Ile Gly Gly Ile Ala
            340                 345                 350
Gly Ala Gly Thr Pro Ala Ala Ala Ala Ala Lys Ala Ala Ala Lys
            355                 360                 365
Ala Ala Lys Tyr Gly Ala Ala Gly Gly Leu Val Pro Gly Gly Pro Gly
            370                 375                 380
Val Arg Leu Pro Gly Ala Gly Ile Pro Gly Val Gly Gly Ile Pro Gly
385                 390                 395                 400
Val Gly Gly Ile Pro Gly Val Gly Gly Pro Gly Ile Gly Gly Pro Gly
            405                 410                 415
Ile Val Gly Gly Pro Gly Ala Val Ser Pro Ala Ala Ala Ala Lys Ala
            420                 425                 430
Ala Ala Lys Ala Ala Lys Tyr Gly Ala Arg Gly Gly Val Gly Ile Pro
            435                 440                 445
Thr Tyr Gly Val Gly Ala Gly Gly Phe Pro Gly Tyr Gly Val Gly Ala
            450                 455                 460
Gly Ala Gly Leu Gly Gly Ala Ser Pro Ala Ala Ala Ala Ala Ala
465                 470                 475                 480
Lys Ala Ala Lys Tyr Gly Ala Gly Gly Ala Gly Ala Leu Gly Gly Leu
            485                 490                 495
Val Pro Gly Ala Val Pro Gly Ala Leu Pro Gly Ala Val Pro Ala Val
            500                 505                 510
Pro Gly Ala Gly Gly Val Pro Gly Ala Gly Thr Pro Ala Ala Ala Ala
            515                 520                 525
Ala Ala Ala Ala Ala Lys Ala Ala Lys Ala Gly Leu Gly Pro Gly
            530                 535                 540
Val Gly Gly Val Pro Gly Gly Val Gly Gly Ile Pro Gly Gly
545                 550                 555                 560
Val Gly Val Gly Gly Val Pro Gly Gly Val Gly Pro Gly Gly Val Thr
            565                 570                 575
Gly Ile Gly Ala Gly Pro Gly Gly Leu Gly Gly Ala Gly Ser Pro Ala
            580                 585                 590
```

```
Ala Ala Lys Ser Ala Ala Lys Ala Ala Lys Ala Gln Tyr Arg Ala
        595                 600                 605
Ala Ala Gly Leu Gly Ala Gly Val Pro Gly Phe Gly Ala Gly Ala
        610                 615                 620
Val Pro Gly Phe Gly Ala Gly Ala Gly Val Pro Gly Phe Gly Ala Gly
625                 630                 635                 640
Ala Gly Val Pro Gly Phe Gly Ala Gly Ala Gly Val Pro Gly Phe Gly
                645                 650                 655
Ala Gly Ala Val Pro Gly Ser Leu Ala Ala Ser Lys Ala Ala Lys Tyr
            660                 665                 670
Gly Ala Ala Gly Gly Leu Gly Gly Pro Gly Gly Leu Gly Gly Pro Gly
        675                 680                 685
Gly Leu Gly Gly Pro Gly Gly Leu Gly Gly Ala Gly Val Pro Gly Arg
        690                 695                 700
Val Ala Gly Ala Ala Pro Pro Ala Ala Ala Ala Ala Ala Lys Ala
705                 710                 715                 720
Ala Ala Lys Ala Ala Gln Tyr Gly Leu Gly Gly Ala Gly Gly Leu Gly
                725                 730                 735
Ala Gly Gly Leu Gly Ala Gly Gly Leu Gly Ala Gly Gly Leu Gly Ala
            740                 745                 750
Gly Gly Leu Gly Ala Gly Gly Leu Gly Ala Gly Gly Leu Gly Ala Gly
        755                 760                 765
Gly Leu Gly Ala Gly Gly Val Ser Pro Ala Ala Ala Ala Lys Ala
        770                 775                 780
Ala Lys Tyr Gly Ala Ala Gly Leu Gly Gly Val Leu Gly Ala Arg Pro
785                 790                 795                 800
Phe Pro Gly Gly Gly Val Ala Ala Arg Pro Gly Phe Gly Leu Ser Pro
                805                 810                 815
Ile Tyr Pro Gly Gly Gly Ala Gly Gly Leu Val Gly Gly Lys Pro
            820                 825                 830
Pro Lys Pro Tyr Gly Gly Ala Leu Gly Ala Leu Gly Tyr Gln Gly Gly
        835                 840                 845
Gly Cys Phe Gly Lys Ser Cys Gly Arg Lys Arg Lys
        850                 855                 860

<210> SEQ ID NO 22
<211> LENGTH: 2583
<212> TYPE: DNA
<213> ORGANISM: Mus musculus

<400> SEQUENCE: 22
atggcgggtc tgacagcggt agtcccgcag cctggcgtct tgctgatcct cttgctcaac      60
ctcctccatc ccgcgcagcc tggaggggtt ccaggagctg tgcctggcgg acttcctggt     120
ggagttcccg gtgagtcta ttatccaggg gctggtattg gaggcctggg aggaggagga     180
ggagctctgg gacctggagg aaaaccacct aagccaggtg ccggacttct gggaacgttt     240
ggagcaggtc ctggaggact ggaggtgct ggcccgggtg caggtctcgg ggcctttcct     300
gcaggcacct tcccaggggc aggagctctg gtgcccgggg agcagcaggg gctgctgcc      360 gcttataaag ctgccgccaa agctgggct gggcttggtg gcgttggcgg agtcccaggt      420
ggtgttggcg ttggtggagt ccaggtggt gttggagttg gcggagtccc aggtggtgtt      480
ggagttggtg gagtccctgg cggtgttggt ggtattggtg gcatcggtgg cttaggagtc     540
tcgacaggtg ctgtggtgcc ccaagtcgga gctggcatcg gagctggagg aaagcctggg     600
```

-continued

```
aaagttcctg gtgttggtct tccaggtgta tacccaggcg gagtgctccc aggaacagga    660
gctcggttcc ctggtgtggg ggtgctccct ggagttccca ctggcacagg agtcaaagcc    720
aaggctccag gtgaggtgg tgctttttct ggaatcccag gggtcggacc ctttgggggt    780
cagcagcctg gtgtcccact gggttatccc atcaaagcac caaagctgcc aggtggctac    840
ggactgccct ataccaatgg gaaattgccc tatggagtag ctggtgcagg ggcaaggct    900
ggctacccaa cagggacagg ggtcggatcc caggcggcgg cggcagcagc taaagcagcc    960
aagtatggtg ctgggggagc tggagtcctc cctggtgttg gaggggtgg cattcctggt   1020
ggtgctggcg caattcctgg gattggaggc attgcaggcg ctggaactcc tgcagcagca   1080
gctgctgcaa aggctgctgc taaggctgct aagtatggag ctgctggagg tttagtgcct   1140
ggtggaccag gagttaggct cccaggtgct ggaatcccag gtgttggtgg cattcctggt   1200
gttggtggca tcccaggtgt tgggggcccct ggtattggag gtccaggcat tgtgggtgga   1260
ccaggagctg tgtcaccagc tgctgctgct aaagctgctg ccaaagctgc caaatacgga   1320
gccagaggtg gagttggcat cccgacatat ggggttggtg ctggtggctt tcctggctat   1380
ggtgttggag ctggagcagg acttggaggt gcaagcccag ctgctgctgc tgccgccgcc   1440
aaagctgcta agtatggtgc tggaggagct ggagccctgg gaggcctggt gccaggtgca   1500
gtaccaggtg cactgccagg tgcagtacca gctgtgccgg gagctggtgg agtgccagga   1560
gcaggtaccc ctgcagctgc agctgctgcc gccgccgcta aagcagccgc caaagcaggt   1620
ttgggtcctg gtgttggtgg ggttcctggt ggagttggtt tggtgggat cccggtgga   1680
gttggtgttg gtggggttcc tggtggagtt ggccctggtg gtgttactgg tattggagct   1740
ggtcctggcg gtcttggagg agcagggtca ccggctgccg ctaaatctgc tgctaaggca   1800
gctgccaaag cccagtacag agctgccgct gggcttggag ctggtgtccc tggatttggg   1860
gctggtgctg gtgtccccgg atttggggct ggtgctggtg tccccggatt tggggctggt   1920
gctggtgtcc ccggatttgg ggctggtgct ggtgtccctg gatttggagc tggagcagta   1980
cctggatcgc tggctgcatc caaagctgct aaatatggag cagcaggtgg ccttggtggc   2040
cctggaggtc tcggtggccc tggaggtctc ggtggacctg gaggacttgg tggggctggt   2100
gttcccggta gagtagcagg agctgcaccc cctgctgctg ccgctgctgc tgccaaagct   2160
gctgctaagg ctgcccagta tggccttggt ggagccggag gattgggagc cggtggactg   2220
ggggccggtg gactgggagc cggtggactg gagctggtg gactgggagc cggtggactg   2280
ggagctggtg gactgggagc cggtggactg ggagctggtg gaggtgtgtc ccctgctgca   2340
gctgctaagg cagccaaata tggtgctgct ggccttggag gtgtcctagg agccaggcca   2400
ttcccaggtg gaggagttgc agcaagacct ggctttggac tttctcccat ttatccaggt   2460
ggtggtgctg ggggcctggg agttggtgga aaaccccga agccctatgg aggagccctt   2520
ggagccctgg gataccaagg tggggggctgc tttgggaaat cctgtgggcg aagagaaag   2580
tga                                                                 2583
```

<210> SEQ ID NO 23
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

```
<400> SEQUENCE: 23

Ser Pro Glu Ala Glu Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 24

Ser Pro Ala Ala Val Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 25

Ser Pro Ala Glu Ala Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 26

Ser Pro Ala Glu Pro Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 27

Ser Pro Ala Glu Val Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 28

Ser Pro Ala Thr Val Lys
1               5
```

```
<210> SEQ ID NO 29
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 29

Ser Pro Glu Lys Ala Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 30

Ser Pro Gly Glu Ala Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 31

Ser Pro Ile Glu Val Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 32

Ser Pro Pro Glu Ala Lys
1               5

<210> SEQ ID NO 33
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 33

Ser Pro Ser Glu Ala Lys
1               5

<210> SEQ ID NO 34
<211> LENGTH: 7
```

```
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 34

Ser Pro Glu Lys Glu Ala Lys
 1               5

<210> SEQ ID NO 35
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 35

Ser Pro Ala Lys Glu Lys Ala Lys
 1               5

<210> SEQ ID NO 36
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 36

Ser Pro Glu Lys Glu Glu Ala Lys
 1               5

<210> SEQ ID NO 37
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 37

Ser Pro Thr Lys Glu Glu Ala Lys
 1               5

<210> SEQ ID NO 38
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 38

Ser Pro Val Lys Glu Glu Ala Lys
 1               5

<210> SEQ ID NO 39
<211> LENGTH: 8
<212> TYPE: PRT
<213> ORGANISM: Artificial Sequence
<220> FEATURE:
<223> OTHER INFORMATION: Entropic bristle domain (EBD) sequence derived
``` from human or mouse neurofilament NF-H proteins
(SEQ ID Nos. 1 and 3)

<400> SEQUENCE: 39

Ser Pro Val Lys Ala Glu Ala Lys
1               5

<210> SEQ ID NO 40
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 40

Ser Pro Val Lys Glu Glu Ala Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 41

Ser Pro Val Lys Glu Glu Val Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 42

Ser Pro Val Lys Glu Glu Glu Lys Pro
1               5

<210> SEQ ID NO 43
<211> LENGTH: 11
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 43

Ser Pro Glu Lys Ala Lys Thr Leu Asp Val Lys
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 44

```
Ser Pro Ala Asp Lys Phe Pro Glu Lys Ala Lys
 1               5                  10
```

<210> SEQ ID NO 45
<211> LENGTH: 13
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 45

```
Ser Pro Glu Ala Lys Thr Pro Ala Lys Glu Glu Ala Arg
 1               5                  10
```

<210> SEQ ID NO 46
<211> LENGTH: 14
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 46

```
Ser Pro Glu Lys Ala Lys Thr Pro Val Lys Glu Gly Ala Lys
 1               5                  10
```

<210> SEQ ID NO 47
<211> LENGTH: 14
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 47

```
Ser Pro Val Lys Glu Glu Ala Lys Thr Pro Glu Lys Ala Lys
 1               5                  10
```

<210> SEQ ID NO 48
<211> LENGTH: 19
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 48

```
Ser Pro Val Lys Glu Gly Ala Lys Pro Pro Glu Lys Ala Lys Pro Leu
 1               5                  10                  15

Asp Val Lys
```

<210> SEQ ID NO 49
<211> LENGTH: 20
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 49

```
Ser Pro Val Lys Glu Asp Ile Lys Pro Pro Ala Glu Ala Lys Ser Pro
```

```
                1               5                  10                 15
Glu Lys Ala Lys
             20

<210> SEQ ID NO 50
<211> LENGTH: 21
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 50

Ser Pro Leu Lys Glu Asp Ala Lys Ala Pro Glu Lys Glu Ile Pro Lys
  1               5                  10                 15

Lys Glu Glu Val Lys
             20

<210> SEQ ID NO 51
<211> LENGTH: 21
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 51

Ser Pro Glu Lys Glu Glu Ala Lys Thr Ser Glu Lys Val Ala Pro Lys
  1               5                  10                 15

Lys Glu Glu Val Lys
             20

<210> SEQ ID NO 52
<211> LENGTH: 25
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 52

Ser Pro Glu Ala Gln Thr Pro Val Gln Glu Glu Ala Thr Val Pro Thr
  1               5                  10                 15

Asp Ile Arg Pro Pro Glu Gln Val Lys
             20                 25

<210> SEQ ID NO 53
<211> LENGTH: 36
<212> TYPE: PRT
<213> ORGANISM: Artificial Sequence
<220> FEATURE:
<223> OTHER INFORMATION: Entropic bristle domain (EBD) sequence derived
      from human or mouse neurofilament NF-H proteins
      (SEQ ID Nos. 1 and 3)

<400> SEQUENCE: 53

Ser Pro Val Lys Glu Glu Val Lys Ala Lys Glu Pro Pro Lys Lys Val
  1               5                  10                 15

Glu Glu Glu Lys Thr Leu Pro Thr Pro Lys Thr Glu Ala Lys Glu Ser
             20                 25                 30

Lys Lys Asp Glu
             35
```

```
<210> SEQ ID NO 54
<211> LENGTH: 4
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 54

Ser Pro Pro Lys
  1

<210> SEQ ID NO 55
<211> LENGTH: 4
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 55

Ser Pro Val Lys
  1

<210> SEQ ID NO 56
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 56

Ser Pro Ala Ala Lys
  1               5

<210> SEQ ID NO 57
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 57

Ser Pro Ala Pro Lys
  1               5

<210> SEQ ID NO 58
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 58

Ser Pro Glu Ala Lys
```

```
1               5

<210> SEQ ID NO 59
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 59

Ser Pro Met Pro Lys
1               5

<210> SEQ ID NO 60
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 60

Ser Pro Pro Ala Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 61

Ser Pro Thr Ala Lys
1               5

<210> SEQ ID NO 62
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 62

Ser Pro Thr Thr Lys
1               5

<210> SEQ ID NO 63
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 63
```

```
<210> SEQ ID NO 64
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 64

Ser Pro Val Ala Lys
 1               5

<210> SEQ ID NO 65
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 65

Ser Pro Val Pro Lys
 1               5

<210> SEQ ID NO 66
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 66

Ser Pro Val Ser Lys
 1               5

<210> SEQ ID NO 67
<211> LENGTH: 6
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 67

Ser Pro Glu Lys Pro Ala
 1               5

<210> SEQ ID NO 68
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 68
```

Ser Pro Val Glu Glu Lys Ala Lys
1               5

<210> SEQ ID NO 69
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 69

Ser Pro Val Glu Glu Lys Gly Lys
1               5

<210> SEQ ID NO 70
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 70

Ser Pro Val Glu Glu Val Lys Pro
1               5

<210> SEQ ID NO 71
<211> LENGTH: 11
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 71

Ser Pro Glu Lys Pro Ala Thr Pro Lys Val Thr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 72

Ser Pro Glu Lys Pro Arg Thr Pro Glu Lys Pro Ala
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

```
<400> SEQUENCE: 73

Ser Pro Glu Lys Pro Thr Thr Pro Glu Lys Val Val
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 74

Ser Pro Glu Lys Pro Ser Ser Pro Leu Lys Asp Glu Lys Ala
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 75

Ser Pro Val Lys Glu Lys Ala Val Glu Glu Met Ile Thr Ile Thr
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 76

Ser Pro Val Lys Glu Glu Ala Ala Glu Glu Ala Ala Thr Ile Thr Lys
1               5                   10                  15

<210> SEQ ID NO 77
<211> LENGTH: 20
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 77

Ser Pro Val Pro Lys Ser Pro Val Glu Glu Val Lys Pro Lys Ala Glu
1               5                   10                  15

Ala Thr Ala Gly
            20

<210> SEQ ID NO 78
<211> LENGTH: 20
<212> TYPE: PRT
<213> ORGANISM: Artificial Sequence
<220> FEATURE:
<223> OTHER INFORMATION: Entropic bristle domain (EBD) sequence derived
``` from bovine, chicken, human, mouse, rat and rabbit
        neurofilament NF-M proteins (SEQ ID Nos.
        5,7,9,11,13 and 15)

<400> SEQUENCE: 78

Ser Pro Val Lys Ala Glu Ser Pro Val Lys Glu Glu Val Pro Ala Lys
1               5                   10                  15

Pro Val Lys Val
            20

<210> SEQ ID NO 79
<211> LENGTH: 21
<212> TYPE: PRT
<213> ORGANISM: Artificial Sequence
<220> FEATURE:
<223> OTHER INFORMATION: Entropic bristle domain (EBD) sequence derived
        from bovine, chicken, human, mouse, rat and rabbit
        neurofilament NF-M proteins (SEQ ID Nos.
        5,7,9,11,13 and 15)

<400> SEQUENCE: 79

Ser Pro Glu Lys Glu Ala Lys Glu Glu Glu Lys Pro Gln Glu Lys Glu
1               5                   10                  15

Lys Glu Lys Glu Lys
            20

<210> SEQ ID NO 80
<211> LENGTH: 23
<212> TYPE: PRT
<213> ORGANISM: Artificial Sequence
<220> FEATURE:
<223> OTHER INFORMATION: Entropic bristle domain (EBD) sequence derived
        from bovine, chicken, human, mouse, rat and rabbit
        neurofilament NF-M proteins (SEQ ID Nos.
        5,7,9,11,13 and 15)

<400> SEQUENCE: 80

Ser Pro Val Lys Ala Thr Thr Pro Glu Ile Lys Glu Glu Glu Gly Glu
1               5                   10                  15

Lys Glu Glu Glu Gly Gln Glu
            20

<210> SEQ ID NO 81
<211> LENGTH: 22
<212> TYPE: PRT
<213> ORGANISM: Artificial Sequence
<220> FEATURE:
<223> OTHER INFORMATION: Entropic bristle domain (EBD) sequence derived
        from bovine, chicken, human, mouse, rat and rabbit
        neurofilament NF-M proteins (SEQ ID Nos.
        5,7,9,11,13 and 15)

<400> SEQUENCE: 81

Ser Pro Val Glu Glu Val Lys Pro Lys Pro Glu Ala Lys Ala Gly Lys
1               5                   10                  15

Gly Glu Gln Lys Glu Glu
            20

<210> SEQ ID NO 82
<211> LENGTH: 24
<212> TYPE: PRT
<213> ORGANISM: Artificial Sequence
<220> FEATURE:
<223> OTHER INFORMATION: Entropic bristle domain (EBD) sequence derived
        from bovine, chicken, human, mouse, rat and rabbit
        neurofilament NF-M proteins (SEQ ID Nos.
        5,7,9,11,13 and 15)

-continued

```
<400> SEQUENCE: 82

Ser Pro Glu Lys Pro Ala Thr Pro Glu Lys Pro Pro Thr Pro Glu Lys
1               5                   10                  15

Ala Ile Thr Pro Glu Lys Val Arg
            20

<210> SEQ ID NO 83
<211> LENGTH: 24
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 83

Ser Pro Glu Lys Pro Ala Thr Pro Glu Lys Pro Arg Thr Pro Glu Lys
1               5                   10                  15

Pro Ala Thr Pro Glu Lys Pro Arg
            20

<210> SEQ ID NO 84
<211> LENGTH: 23
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 84

Ser Pro Lys Glu Glu Lys Val Glu Lys Glu Glu Lys Pro Lys Asp
1               5                   10                  15

Val Pro Lys Lys Lys Ala Glu
            20

<210> SEQ ID NO 85
<211> LENGTH: 24
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 85

Ser Pro Lys Glu Glu Lys Ala Glu Lys Lys Glu Glu Lys Pro Lys Asp
1               5                   10                  15

Val Pro Glu Lys Lys Lys Ala Glu
            20

<210> SEQ ID NO 86
<211> LENGTH: 24
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 86
```

-continued

```
Ser Pro Val Glu Glu Ala Lys Ser Lys Ala Glu Val Gly Lys Gly Glu
1               5                   10                  15

Gln Lys Glu Glu Glu Glu Lys Glu
            20

<210> SEQ ID NO 87
<211> LENGTH: 24
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 87

Ser Pro Lys Glu Glu Lys Val Glu Lys Lys Glu Glu Lys Pro Lys Asp
1               5                   10                  15

Val Pro Asp Lys Lys Lys Ala Glu
            20

<210> SEQ ID NO 88
<211> LENGTH: 26
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 88

Ser Pro Val Lys Glu Glu Ala Val Ala Glu Val Val Thr Ile Thr Lys
1               5                   10                  15

Ser Val Lys Val His Leu Glu Lys Glu Thr
            20                  25

<210> SEQ ID NO 89
<211> LENGTH: 31
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 89

Ser Ser Glu Lys Asp Glu Gly Glu Gln Glu Glu Glu Glu Gly Glu Thr
1               5                   10                  15

Glu Ala Glu Gly Glu Gly Glu Glu Ala Glu Ala Lys Glu Glu Lys
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 90

Ser Pro Val Glu Glu Val Lys Pro Lys Ala Glu Ala Gly Ala Glu Lys
1               5                   10                  15
```

-continued

```
Gly Glu Gln Lys Glu Lys Val Glu Glu Lys Lys Glu Ala Lys Glu
            20                  25                  30
```

<210> SEQ ID NO 91
<211> LENGTH: 37
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 91

```
Ser Pro Val Thr Glu Gln Ala Lys Ala Val Gln Lys Ala Ala Ala Glu
1               5                   10                  15

Val Gly Lys Asp Gln Lys Ala Glu Lys Ala Ala Glu Lys Ala Ala Lys
            20                  25                  30

Glu Glu Lys Ala Ala
        35
```

<210> SEQ ID NO 92
<211> LENGTH: 44
<212> TYPE: PRT
<213> ORGANISM: Artificial Sequence
<220> FEATURE:
<223> OTHER INFORMATION: Entropic bristle domain (EBD) sequence derived
      from bovine, chicken, human, mouse, rat and rabbit
      neurofilament NF-M proteins (SEQ ID Nos.
      5,7,9,11,13 and 15)

<400> SEQUENCE: 92

```
Ser Pro Glu Ala Lys Glu Glu Glu Glu Gly Glu Lys Glu Glu Glu
1               5                   10                  15

Glu Glu Gly Gln Glu Glu Glu Glu Glu Asp Glu Gly Val Lys Ser
            20                  25                  30

Asp Gln Ala Glu Glu Gly Gly Ser Glu Lys Glu Gly
        35                  40
```

<210> SEQ ID NO 93
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 93

```
Glu Gly Gly Gly Ser
1               5
```

<210> SEQ ID NO 94
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 94

```
Glu Gly Gly Gly Thr
1               5
```

<210> SEQ ID NO 95

```
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 95

Ser Glu Gly Gly Gly
 1               5

<210> SEQ ID NO 96
<211> LENGTH: 7
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 96

Gly Gly Gly Ser Gly Gly Gly
 1               5

<210> SEQ ID NO 97
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 97

Ser Gly Gly Gly Ser Gly Ser Gly
 1               5

<210> SEQ ID NO 98
<211> LENGTH: 9
<212> TYPE: PRT
<213> ORGANISM: Artificial Sequence
<220> FEATURE:
<223> OTHER INFORMATION: Entropic bristle domain (EBD) sequence derived
      from filamentous phage fd adsorption protein pIII
      (SEQ ID No. 17)

<400> SEQUENCE: 98

Ser Gly Gly Gly Ser Glu Gly Gly Gly
 1               5

<210> SEQ ID NO 99
<211> LENGTH: 13
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 99

Phe Ser Phe Gly Thr Ser Gln Pro Asn Asn Thr Pro Ser
 1               5                  10

<210> SEQ ID NO 100
<211> LENGTH: 17
<212> TYPE: PRT
<213> ORGANISM: Artificial Sequence
<220> FEATURE:
```

```
<223> OTHER INFORMATION: Entropic bristle domain (EBD) sequence derived
      from yeast nucleoporin Nup2p protein (SEQ ID No.
      19)

<400> SEQUENCE: 100

Phe Ser Phe Ser Ile Pro Ser Lys Asn Thr Pro Asp Ala Ser Lys Pro
1               5                   10                  15

Ser

<210> SEQ ID NO 101
<211> LENGTH: 16
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 101

Phe Val Phe Gly Gln Ala Ala Ala Lys Pro Ser Leu Glu Lys Ser Ser
1               5                   10                  15

<210> SEQ ID NO 102
<211> LENGTH: 17
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 102

Phe Ser Phe Gly Val Pro Asn Ser Ser Lys Asn Glu Thr Ser Lys Pro
1               5                   10                  15

Val

<210> SEQ ID NO 103
<211> LENGTH: 17
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 103

Phe Thr Phe Gly Thr Lys His Ala Ala Asp Ser Gln Asn Asn Lys Pro
1               5                   10                  15

Ser

<210> SEQ ID NO 104
<211> LENGTH: 18
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 104

Phe Thr Phe Gly Ser Ser Ala Leu Ala Asp Asn Lys Glu Asp Val Lys
1               5                   10                  15

Lys Pro

<210> SEQ ID NO 105
```

```
<211> LENGTH: 19
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 105

Phe Ser Phe Gly Ile Asn Thr Asn Thr Thr Lys Thr Ala Asp Thr Lys
 1               5                  10                  15

Ala Pro Thr

<210> SEQ ID NO 106
<211> LENGTH: 26
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 106

Phe Ser Phe Gly Lys Thr Thr Ala Asn Leu Pro Ala Asn Ser Ser Thr
 1               5                  10                  15

Ser Pro Ala Pro Ser Ile Pro Ser Thr Gly
            20                  25

<210> SEQ ID NO 107
<211> LENGTH: 27
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 107

Phe Ser Phe Gly Pro Lys Lys Glu Asn Arg Lys Lys Asp Glu Ser Asp
 1               5                  10                  15

Ser Glu Asn Asp Ile Glu Ile Lys Gly Pro Glu
            20                  25

<210> SEQ ID NO 108
<211> LENGTH: 31
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 108

Phe Lys Phe Ser Gly Thr Val Ser Ser Asp Val Phe Lys Leu Asn Pro
 1               5                  10                  15

Ser Thr Asp Lys Asn Glu Lys Lys Thr Glu Thr Asn Ala Lys Pro
            20                  25                  30

<210> SEQ ID NO 109
<211> LENGTH: 33
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)
```

<400> SEQUENCE: 109

Phe Lys Phe Ser Leu Pro Phe Glu Gln Lys Gly Ser Gln Thr Thr Thr
1               5                   10                  15

Asn Asp Ser Lys Glu Glu Ser Thr Thr Glu Ala Thr Gly Asn Glu Ser
            20                  25                  30

Gln

<210> SEQ ID NO 110
<211> LENGTH: 34
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 110

Phe Thr Phe Gly Ser Thr Thr Ile Glu Lys Lys Asn Asp Glu Asn Ser
1               5                   10                  15

Thr Ser Asn Ser Lys Pro Glu Lys Ser Ser Asp Ser Asn Asp Ser Asn
            20                  25                  30

Pro Ser

<210> SEQ ID NO 111
<211> LENGTH: 36
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 111

Phe Ser Phe Gly Ile Ser Asn Gly Ser Glu Ser Lys Asp Ser Asp Lys
1               5                   10                  15

Pro Ser Leu Pro Ser Ala Val Asp Gly Glu Asn Asp Lys Lys Glu Ala
            20                  25                  30

Thr Lys Pro Ala
        35

<210> SEQ ID NO 112
<211> LENGTH: 38
<212> TYPE: PRT
<213> ORGANISM: Artificial Sequence
<220> FEATURE:
<223> OTHER INFORMATION: Entropic bristle domain (EBD) sequence derived
      from yeast nucleoporin Nup2p protein (SEQ ID No.
      19)

<400> SEQUENCE: 112

Phe Ser Phe Ser Ser Ala Thr Ser Thr Thr Glu Gln Thr Lys Ser Lys
1               5                   10                  15

Asn Pro Leu Ser Leu Thr Glu Ala Thr Lys Thr Asn Val Asp Asn Asn
            20                  25                  30

Ser Lys Ala Glu Ala Ser
        35

<210> SEQ ID NO 113
<211> LENGTH: 52
<212> TYPE: PRT
<213> ORGANISM: Artificial Sequence
<220> FEATURE:
<223> OTHER INFORMATION: Entropic bristle domain (EBD) sequence derived

```
      from yeast nucleoporin Nup2p protein (SEQ ID No.
      19)

<400> SEQUENCE: 113

Phe Ser Phe Gly Ala Ala Thr Pro Ser Ala Lys Glu Ala Ser Gln Glu
1               5                   10                  15

Asp Asp Asn Asn Asn Val Glu Lys Pro Ser Ser Lys Pro Ala Phe Asn
            20                  25                  30

Leu Ile Ser Asn Ala Gly Thr Glu Lys Glu Lys Glu Ser Lys Lys Asp
        35                  40                  45

Ser Lys Pro Ala
    50

<210> SEQ ID NO 114
<211> LENGTH: 4
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 114

Val Pro Gly Ala
1

<210> SEQ ID NO 115
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 115

Gly Ala Gly Gly Leu
1               5

<210> SEQ ID NO 116
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 116

Gly Ala Gly Gly Gly
1               5

<210> SEQ ID NO 117
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 117

Val Pro Gly Val Gly
1               5

<210> SEQ ID NO 118
<211> LENGTH: 8
<212> TYPE: PRT
<213> ORGANISM: Artificial Sequence
<220> FEATURE:
```

```
<223> OTHER INFORMATION: Entropic bristle domain (EBD) sequence derived
      from mouse elastin protein (SEQ ID No. 21)

<400> SEQUENCE: 118

Val Pro Gly Phe Gly Ala Gly Ala
 1               5

<210> SEQ ID NO 119
<211> LENGTH: 8
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 119

Val Pro Gly Ala Leu Pro Gly Ala
 1               5

<210> SEQ ID NO 120
<211> LENGTH: 9
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 120

Val Pro Gly Phe Gly Ala Gly Ala Gly
 1               5

<210> SEQ ID NO 121
<211> LENGTH: 9
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 121

Val Pro Ala Val Pro Gly Ala Gly Gly
 1               5

<210> SEQ ID NO 122
<211> LENGTH: 9
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 122

Val Pro Gly Gly Val Gly Val Gly Gly
 1               5

<210> SEQ ID NO 123
<211> LENGTH: 10
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 123

Val Gly Ala Gly Gly Phe Pro Gly Tyr Gly
 1               5                  10
```

```
<210> SEQ ID NO 124
<211> LENGTH: 12
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 124

Val Pro Gly Ala Val Pro Gly Gly Leu Pro Gly Gly
1               5                   10

<210> SEQ ID NO 125
<211> LENGTH: 15
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 125

Val Ser Pro Ala Ala Ala Ala Lys Ala Ala Lys Tyr Gly Ala Ala
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 126

Val Pro Gln Val Gly Ala Gly Ile Gly Ala Gly Gly Lys Pro Gly Lys
1               5                   10                  15

<210> SEQ ID NO 127
<211> LENGTH: 18
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 127

Val Pro Gly Gly Val Gly Val Gly Gly Ile Pro Gly Gly Val Gly Val
1               5                   10                  15

Gly Gly

<210> SEQ ID NO 128
<211> LENGTH: 21
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 128

Val Pro Gly Gly Val Gly Gly Ile Gly Gly Ile Gly Gly Leu Gly Val
1               5                   10                  15

Ser Thr Gly Ala Val
            20

<210> SEQ ID NO 129
<211> LENGTH: 27
<212> TYPE: PRT
<213> ORGANISM: Artificial Sequence
```

```
<220> FEATURE:
<223> OTHER INFORMATION: Entropic bristle domain (EBD) sequence derived
      from mouse elastin protein (SEQ ID No. 21)

<400> SEQUENCE: 129

Val Pro Gly Gly Ala Ala Gly Ala Ala Ala Ala Tyr Lys Ala Ala Ala
1               5                   10                  15

Lys Ala Gly Ala Gly Leu Gly Gly Val Gly Gly
            20                  25

<210> SEQ ID NO 130
<211> LENGTH: 28
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 130

Val Ser Pro Ala Ala Ala Ala Lys Ala Ala Ala Lys Ala Ala Lys Tyr
1               5                   10                  15

Gly Ala Arg Gly Gly Val Gly Ile Pro Thr Tyr Gly
            20                  25

<210> SEQ ID NO 131
<211> LENGTH: 30
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 131

Lys Pro Pro Lys Pro Tyr Gly Gly Ala Leu Gly Ala Leu Gly Tyr Gln
1               5                   10                  15

Gly Gly Gly Cys Phe Gly Lys Ser Cys Gly Arg Lys Arg Lys
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 132

Val Pro Gly Ala Gly Thr Pro Ala Ala Ala Ala Ala Ala Ala Ala Ala
1               5                   10                  15

Lys Ala Ala Ala Lys Ala Gly Leu Gly Pro Gly Val Gly Gly
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 133

Val Pro Gly Arg Val Ala Gly Ala Ala Pro Pro Ala Ala Ala Ala Ala
1               5                   10                  15

Ala Ala Lys Ala Ala Ala Lys Ala Ala Gln Tyr Gly Leu Gly
            20                  25                  30
```

```
<210> SEQ ID NO 134
<211> LENGTH: 30
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 134

Val Pro Gly Val Gly Leu Pro Gly Val Tyr Pro Gly Gly Val Leu Pro
1               5                   10                  15

Gly Thr Gly Ala Arg Phe Pro Gly Val Gly Val Leu Pro Gly
            20                  25                  30

<210> SEQ ID NO 135
<211> LENGTH: 33
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 135

Val Pro Thr Gly Thr Gly Val Lys Ala Lys Ala Pro Gly Gly Gly Gly
1               5                   10                  15

Ala Phe Ser Gly Ile Pro Gly Val Gly Pro Phe Gly Gly Gln Gln Pro
            20                  25                  30

Gly

<210> SEQ ID NO 136
<211> LENGTH: 34
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 136

Val Pro Gly Gly Val Tyr Tyr Pro Gly Ala Gly Ile Gly Gly Leu Gly
1               5                   10                  15

Gly Gly Gly Gly Ala Leu Gly Pro Gly Gly Lys Pro Pro Lys Pro Gly
            20                  25                  30

Ala Gly

<210> SEQ ID NO 137
<211> LENGTH: 35
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 137

Val Gly Ala Gly Ala Gly Leu Gly Gly Ala Ser Pro Ala Ala Ala Ala
1               5                   10                  15

Ala Ala Ala Lys Ala Ala Lys Tyr Gly Ala Gly Gly Ala Gly Ala Leu
            20                  25                  30

Gly Gly Leu
        35

<210> SEQ ID NO 138
<211> LENGTH: 40
```

```
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 138

Gly Leu Gly Gly Val Leu Gly Ala Arg Pro Phe Pro Gly Gly Gly Val
1               5                   10                  15

Ala Ala Arg Pro Gly Phe Gly Leu Ser Pro Ile Tyr Pro Gly Gly
            20                  25                  30

Ala Gly Gly Leu Gly Val Gly Gly
        35                  40

<210> SEQ ID NO 139
<211> LENGTH: 41
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 139

Val Pro Gly Ser Leu Ala Ala Ser Lys Ala Ala Lys Tyr Gly Ala Ala
1               5                   10                  15

Gly Gly Leu Gly Gly Pro Gly Gly Leu Gly Gly Pro Gly Gly Leu Gly
            20                  25                  30

Gly Pro Gly Gly Leu Gly Gly Ala Gly
        35                  40

<210> SEQ ID NO 140
<211> LENGTH: 45
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 140

Val Pro Gly Gly Pro Gly Val Arg Leu Pro Gly Ala Gly Ile Pro Gly
1               5                   10                  15

Val Gly Gly Ile Pro Gly Val Gly Gly Ile Pro Gly Val Gly Gly Pro
            20                  25                  30

Gly Ile Gly Gly Pro Gly Ile Val Gly Gly Pro Gly Ala
        35                  40                  45

<210> SEQ ID NO 141
<211> LENGTH: 50
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 141

Val Leu Pro Gly Val Gly Gly Gly Ile Pro Gly Gly Ala Gly Ala
1               5                   10                  15

Ile Pro Gly Ile Gly Gly Ile Ala Gly Ala Gly Thr Pro Ala Ala Ala
            20                  25                  30

Ala Ala Ala Lys Ala Ala Ala Lys Ala Ala Lys Tyr Gly Ala Ala Gly
        35                  40                  45

Gly Leu
    50
```

<210> SEQ ID NO 142
<211> LENGTH: 50
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 142

Val Pro Gly Gly Val Gly Pro Gly Gly Val Thr Gly Ile Gly Ala Gly
 1               5                  10                  15

Pro Gly Gly Leu Gly Gly Ala Gly Ser Pro Ala Ala Ala Lys Ser Ala
            20                  25                  30

Ala Lys Ala Ala Ala Lys Ala Gln Tyr Arg Ala Ala Ala Gly Leu Gly
        35                  40                  45

Ala Gly
    50

<210> SEQ ID NO 143
<211> LENGTH: 64
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)

<400> SEQUENCE: 143

Val Pro Leu Gly Tyr Pro Ile Lys Ala Pro Lys Leu Pro Gly Gly Tyr
 1               5                  10                  15

Gly Leu Pro Tyr Thr Asn Gly Lys Leu Pro Tyr Gly Val Ala Gly Ala
            20                  25                  30

Gly Gly Lys Ala Gly Tyr Pro Thr Gly Thr Gly Val Gly Ser Gln Ala
        35                  40                  45

Ala Ala Ala Ala Ala Lys Ala Ala Lys Tyr Gly Ala Gly Gly Ala Gly
    50                  55                  60

<210> SEQ ID NO 144
<211> LENGTH: 5
<212> TYPE: PRT
<213> ORGANISM: Artificial Sequence
<220> FEATURE:
<223> OTHER INFORMATION: Entropic bristle domain (EBD) sequence derived
      from mouse elastin protein (SEQ ID No. 21)
<220> FEATURE:
<221> NAME/KEY: MOD_RES
<222> LOCATION: (4)...(4)
<223> OTHER INFORMATION: Xaa is any amino acid except proline

<400> SEQUENCE: 144

Val Pro Gly Xaa Gly
 1               5

ENTROPIC BRISTLE DOMAIN SEQUENCES AND THEIR USE IN RECOMBINANT PROTEIN PRODUCTION

FIELD OF THE INVENTION

The present invention relates generally to compositions and methods for recombinant protein production and, more particularly, to fusion polypeptides, polynucleotides encoding fusion polypeptides, expression vectors, kits, and related methods for recombinant protein production.

DETAILED OF THE RELATED ART

A large percentage of the proteins identified via the different genome sequencing effort have been difficult to express and/or purify as recombinant proteins using standard methods. For example, a trial study using *Methanobacterium thermoautotrophicum* as a model system identified a number of problems associated with high throughput structure determination (Christendat et al. (2000) Prog. Biophys. Mol. Biol. 73(5): 339-345; Christendat et al. (2000) Nat Struct Biol 7(10): 903-909). The complete list of genome-encoded proteins was filtered to remove proteins with predicted transmembrane regions or homologues to known structures. When these filtered proteins were taken through the cloning, expression, and structural determination steps of a high throughput process, only about 50% of the selected proteins could be purified in a state suitable for structural studies, with roughly 45% of large expressed proteins and 30% of small expressed proteins failing due to insolubility. The study concluded that considerable effort must be invested in improving the attrition rate due to proteins with poor expression levels and unfavorable biophysical properties. (Christendat et al. (2000) Prog. Biophys. Mol. Biol. 73(5): 339-345; Christendat et al. (2000) Nat Struct Biol 7(10): 903-909).

Similar results have been observed for other prokaryotic proteomes. One study reported the successful cloning and attempted expression of 1376 (73%) of the predicted 1877 genes of the *Thermotoga maritima* proteome. However, crystallization conditions were able to be determined for only 432 proteins (23%). A significant component of the decrease between the cloned and crystallized success levels was due to poor protein solubility and stability (Kuhn et al. (2002) Proteins 49(1): 142-5).

Similarly low success rates have been reported for eukaryotic proteomes. A study of a sample set of human proteins, for example, reported that the failure rate using high-throughput methods for three classes of proteins based on cellular location was 50% for soluble proteins, 70% for extracellular proteins, and more than 80% for membrane proteins (Braun et al. (2002) Proc Natl Acad Sci USA 99(5): 2654-9).

Interactions between individual recombinant proteins are responsible for a significant number of the previously mentioned failures. In a high-throughput structural determination study, Christendat and colleagues found that 24 of 32 proteins that were classified by nuclear magnetic resonance as aggregated displayed circular dichroism spectra consistent with stable folded proteins, suggesting that these proteins were folded properly but aggregated due to surface interactions (Christendat et al. (2000) Prog. Biophys. Mol. Biol. 73(5): 339-345). One possible explanation for this is that these proteins function in vivo as part of multimeric units but when they are recombinantly expressed, dimerization domains are exposed that mediate protein-protein interactions.

Prior methods used to increase recombinant protein stability include production in *E. coli* strains that are deficient in proteases (Gottesman and Zipser (1978) J Bacteriol 133(2): 844-51) and production of fusions of bacterial protein fragments to a recombinant polypeptide/protein of interest (Itakura et al., Science, 1977. 198:1056-63; Shen, Proc Natl Acad Sci USA, 1984. 81:4627-31). has also been attempted to stabilize foreign proteins in *E. coli*. In addition, fusing a leader sequence to a recombinant protein may cause a gene product to accumulate in the periplasm or be excreted, which may result in increased recovery of properly folded soluble protein (Nilsson et al., EMBO J, 1985. 4:1075-80; Abrahmsen et al., Nucleic Acids Res, 1986. 14:7487-500). These strategies have advantages for some proteins but they generally do not succeed when used, for example, with membrane proteins or proteins capable of strong protein-protein interactions.

Fusion polypeptides have also been used as an approach for improving the solubility and folding of recombinant polypeptides/proteins produced in *E. coli* (Zhan et al., Gene, 2001. 281:1-9). Some commonly used fusion partners which have been linked to heterologous protein sequences of interest include calmodulin-binding peptide (CBP) (Vaillancourt et al., Biotechniques, 1997. 22:451-3), glutathione-S-transferase (GST) (Smith, Methods Enzymol, 2000. 326:254-70), thioredoxin (TRX) (Martin Hammarström et al., Protein Science, 2002. 11:313-321), and maltose-binding protein (MBP) (Sachdev et al., Methods Enzymol, 2000. 326:312-21). Glutathione-S-transferase and maltose-binding protein have been found to increase the recombinant protein purification success rate when fused to a heterologous sequence in a controlled trial of 32 human test proteins (Braun et al., Proc Natl Acad Sci USA, 2002. 99:2654-9). Further, maltose-binding protein domain fusions have been shown to increase the solubility of recombinant proteins (Kapust et al., Protein Sci, 1999. 8:1668-74; Braun et al., Proc Natl Acad Sci USA, 2002. 99:2654-9; Martin Hammarström et al., Protein Science, 2002. 11:313-321). Maltose-binding protein may further benefit recombinant protein solubility and folding in that it may have chaperone-like properties that assist in folding of the fusion partner (Richarme et al., J Biol Chem, 1997. 272: 15607-12; Bach et al., J Mol Biol, 2001. 312:79-93. However, these fusion approaches used to date have not been amendable to all classes of proteins, and have thus met with only limited success.

Entropic bristles have been used in a variety of polymers to reduce aggregation of small particles such as latex particles in paints and to stabilize a wide variety of other colloidal products (Hoh, Proteins, 1998. 32:223-228). Entropic bristles generally comprise amino acid residues that do not have a tendency to form secondary structure and in the process of random motion about their attachment points sweep out a significant region in space and entropically exclude other molecules by their random motion (Hoh, Proteins, 1998. 32:223-228). Entropic bristles are singular elements, comprising highly flexible, non-aggregating polymer chains, of which entropic brushes are assembled. In polymer chemistry, entropic bristles have been affixed to the surfaces of particles (e.g. latex beads), thereby forming entropic brushes which, in turn, prevent particle aggregation (*Stabilization by attached polymer: steric stabilization*, in *Polymeric stabilization of colloidal dispersions*, D. H. Napper, Editor. 1983, Academic Press: London. p. 18-30). EBDs can exclude large molecules but do not exclude small molecules such as water, salts, metal ions, or cofactors (Hoh, Proteins, 1998. 32:223-228).

EBDs can also function as steric stabilizers and operate through steric hindrance stabilization (*Stabilization by attached polymer: steric stabilization*, in *Polymeric stabilization of colloidal dispersions*, D. H. Napper, Editor. 1983, Academic Press: London. p. 18-30). Napper described characteristics that contribute to steric stabilization functions, including (1) they have an amphipathic sequence; (2) they are attached to the colloidal particle by one end rather than being totally adsorbed; (3) they are soluble in the medium used; (4) they are mutually repulsive; (5) they are thermodynamically stable; and (6) they exhibit stabilizing ability in proportion to their length. Steric stabilizers intended to function in aqueous media extend from the surface of colloidal molecules thus transforming their surfaces from hydrophobic to hydrophilic. The fact that sterically stabilized particles are thermodynamically stable leads them to spontaneously re-disperse when dried residue is reintroduced to solvent. Entropic bristles can adopt random-walk configurations in solution (Milner, Science, 1991. 251:905-914). These chains extend from an attachment point because of their affinity for the solvent. This affinity is due in part to the highly charged nature of the entropic bristle sequence.

While certain prior approaches have met with some success, there remains a need for new compositions and methods for improving the properties and characteristics of recombinant proteins, e.g., improving solubility, stability, yield and/or folding of recombinant proteins. The present invention addresses these needs and offers other related advantages by employing entropic bristle domain sequences as fusion partners in recombinant protein production, as described herein.

SUMMARY OF THE INVENTION

According to a general aspect of the present invention, there are provided isolated fusion polypeptides comprising at least one entropic bristle domain (EBD) sequence and at least one heterologous polypeptide sequence of interest. By providing an EBD sequence which effectively sweeps out the three-dimensional space surrounding a newly synthesized heterologous polypeptide, the fusion polypeptides of the invention offer a number of advantages over prior fusion polypeptides and methods relating thereto.

In one embodiment, a fusion polypeptide comprising an EBD sequence and a heterologous polypeptide sequence exhibits improved solubility relative to the corresponding heterologous polypeptide in the absence of the EBD sequence. In a related embodiment, the fusion polypeptide has at least 5% increased solubility relative to the heterologous polypeptide sequence, at least 25% increased solubility relative to the heterologous polypeptide sequence, or at least 50% increased solubility relative to the heterologous polypeptide sequence.

In another embodiment, a fusion polypeptide of the invention exhibits reduced aggregation relative to the level of aggregation of the heterologous polypeptide sequence in the absence of the EBD sequence. For example, a fusion polypeptide of the invention generally exhibits at least 10% reduced aggregation relative to the heterologous polypeptide sequence or at least 25% reduced aggregation relative to the heterologous polypeptide sequence.

In another embodiment, a fusion polypeptide of the invention exhibits improved self-folding relative to the heterologous polypeptide sequence in the absence of the EBD sequence.

In another embodiment of the present invention, an EBD sequence employed in a fusion polypeptide comprises an amino acid sequence that maintains a substantially random coil conformation.

In another embodiment, the EBD sequence of a fusion polypeptide of the invention comprises an amino acid sequence that is substantially mutually repulsive.

In another embodiment, the EBD sequence of a fusion polypeptide of the invention comprises an amino acid sequence that remains in substantially constant motion.

In a more particular embodiment, an EBD sequence of a fusion polypeptide of the invention is derived from a mammalian neurofilament protein. In a related embodiment, the EBD sequence of a fusion polypeptide of the invention is derived from a mammalian neurofilament NF-H protein. In another related embodiment, the EBD sequence of a fusion polypeptide of the invention is derived from a human neurofilament NF-H protein having the sequence set forth in SEQ ID NO: 1. In another related embodiment, the EBD sequence of a fusion polypeptide of the invention is derived from a mouse neurofilament NF-H protein having the sequence set forth in SEQ ID NO: 3.

In yet another related embodiment, the EBD sequence of a fusion polypeptide of the invention comprises a neurofilament NF-H sequence selected from the group consisting of SPEAEK (SEQ ID NO:23), SPAAVK (SEQ ID NO:24), SPAEAK (SEQ ID NO:25), SPAEPK (SEQ ID NO:26), SPAEVK (SEQ ID NO:27), SPATVK (SEQ ID NO:28), SPEKAK (SEQ ID NO:29), SPGEAK (SEQ ID NO:30), SPIEVK (SEQ ID NO:31), SPPEAK (SEQ ID NO:32), SPSEAK (SEQ ID NO:33), SPEKEAK (SEQ ID NO:34), SPAKEKAK (SEQ ID NO:35), SPEKEEAK (SEQ ID NO:36), SPTKEEAK (SEQ ID NO:37), SPVKEEAK (SEQ ID NO:38), SPVKAEAK (SEQ ID NO:39), SPVKEEAK (SEQ ID NO:40), SPVKEEVK (SEQ ID NO:41), SPVKEEEKP (SEQ ID NO:42), SPEKAKTLDVK (SEQ ID NO:43), SPADKFPEKAK (SEQ ID NO:44), SPEAKTPAKEEAR (SEQ ID NO:45), SPEKAKTPVKEGAK (SEQ ID NO:46), SPVKEEAKTPEKAK (SEQ ID NO:47), SPVKEGAKPPEKAKPLDVK (SEQ ID NO:48), SPVKEDIKPPAEAKSPEKAK (SEQ ID NO:49), SPLKEDAKAPEKEIPKKEEVK (SEQ ID NO:50), SPEKEEAKTSEKVAPKKEEVK (SEQ ID NO:51), SPEAQTPVQEEATVPTDIRPPEQVK (SEQ ID NO:52), SPVKEEVKAKEPPKKVEEEKTLPTPKTEAKESKKDE (SEQ ID NO:53).

In yet another related embodiment, the EBD sequence of a fusion polypeptide of the invention comprises at least 2-100 repeats of a neurofilament NF-H sequence set forth above, or a combination thereof.

According to another particular embodiment of the present invention, an EBD sequence of a fusion polypeptide is derived from a mammalian neurofilament protein NF-M. In a related embodiment, the EBD sequence of a fusion polypeptide of the invention is derived from a bovine neurofilament NF-M protein having the sequence set forth in SEQ ID NO: 5. In another related embodiment, the EBD sequence of a fusion polypeptide of the invention is derived from a chicken neurofilament NF-M protein having the sequence set forth in SEQ ID NO: 7. In yet another related embodiment, the EBD sequence of a fusion polypeptide of the invention is derived from a human neurofilament NF-M protein having the sequence set forth in SEQ ID NO: 9. In another related embodiment, the EBD sequence of a fusion polypeptide of the invention is derived from a mouse neurofilament NF-M protein having the sequence set forth in SEQ ID NO: 11. In yet another related embodiment, the EBD sequence of a fusion polypeptide of the invention is derived from a rat neurofilament NF-M protein having the sequence set forth in SEQ ID NO: 13. In another related embodiment, the EBD sequence of a fusion polypeptide of the invention is derived from a rabbit neurofilament NF-M protein having the sequence set forth in SEQ ID NO: 15.

In yet another related embodiment, the EBD sequence of a fusion polypeptide of the invention comprises a neurofilament NF-M sequence selected from the group consisting of SPPK (SEQ ID NO:54), SPVK (SEQ ID NO:55), SPAAK (SEQ ID NO:56), SPAPK (SEQ ID NO:57), SPEAK (SEQ ID NO:58), SPMPK (SEQ ID NO:59), SPPAK (SEQ ID NO:60), SPTAK (SEQ ID NO:61), SPTTK (SEQ ID NO:62), SPVAK (SEQ ID NO:63), SPVAK (SEQ ID NO:64), SPVPK (SEQ ID NO:65), SPVSK (SEQ ID NO:66), SPEKPA (SEQ ID NO:67), SPVEEKAK (SEQ ID NO:68), SPVEEKGK (SEQ ID NO:69), SPVEEVKP (SEQ ID NO:70), SPEKPATPKVT (SEQ ID NO:71), SPEKPRTPEKPA (SEQ ID NO:72), SPEKPTTPEKVV (SEQ ID NO:73), SPEKPSSPLKDEKA (SEQ ID NO:74), SPVKEKAVEEMITIT (SEQ ID NO:75), SPVKEEAAEEAATITK (SEQ ID NO:76), SPVPKSPVEEVKPKAEATAG (SEQ ID NO:77), SPVKAESPVKEEVPAKPVKV (SEQ ID NO:78), SPEKEAKEEEKPQEKEKEKEK (SEQ ID NO:79), SPVKATTPEIKEEEGEKEEEGQE (SEQ ID NO:80), SPVEEVKPKPEAKAGKGEQKEE (SEQ ID NO:81), SPEKPATPEKPPTPEKAITPEKVR (SEQ ID NO:82), SPEKPATPEKPRTPEKPATPEKPR (SEQ ID NO:83), SPKEEKVEKKEEKPKDVPKKKAE (SEQ ID NO:84), SPKEEKAEKKEEKPKDVPEKKKAE (SEQ ID NO:85), SPVEEAKSKAEVGKGEQKEEEEKE (SEQ ID NO:86), SPKEEKVEKKEEKPKDVPDKKKAE (SEQ ID NO:87), SPVKEEAVAEVVTITKSVKVHLEKET (SEQ ID NO:88), SSEKDEGEQEEEEGETEAEGEGEEAEAKEEK (SEQ ID NO:89), SPVEEVKPKAEAGAEKGEQKEKVEEEKKEAKE (SEQ ID NO:90), SPVTEQAKAVQKAAAEVGKDQKAEKAAEKAAKEEKAA (SEQ ID NO:91), SPEAKEEEEEGEKEEEEEGQEEEEEEDEGVKSDQAEEGGSEKEG (SEQ ID NO:92).

According to another particular embodiment of the present invention, an EBD sequence of a fusion polypeptide is derived from a phage sequence. In a related embodiment, the EBD sequence of a fusion polypeptide of the invention is derived from a filamentous phage fd. In another related embodiment, the EBD sequence of a fusion polypeptide of the invention comprises at least one linker region derived from a filamentous phage fd adsorption protein pIII. In another related embodiment, the EBD sequence of a fusion polypeptide of the invention comprises a filamentous phage fd adsorption protein pIII having a sequence set forth in SEQ ID NO: 17. In another related embodiment, the EBD sequence of a fusion polypeptide of the invention comprises a filamentous phage fd adsorption protein pIII sequence selected from the group consisting of EGGGS (SEQ ID NO:93), EGGGT (SEQ ID NO:94), SEGGG (SEQ ID NO:95), GGGSGGG (SEQ ID NO:96), SGGGSGSG (SEQ ID NO:97), and SGGGSEGGG (SEQ ID NO:98).

In yet another related embodiment, the EBD sequence of a fusion polypeptide of the invention comprises at least 2-100 repeats of A filamentous phage fd adsorption protein pIII sequence set forth above, or a combination thereof.

In another particular embodiment of the invention, an EBD sequence of a fusion polypeptide of the invention is derived from a nuclear pore protein. In a more particular embodiment, the EBD sequence of a fusion polypeptide of the invention is derived from an yeast nuclear pore Nup2p protein having the sequence set forth in SEQ ID NO: 19. In a related embodiment, the EBD is derived from the yeast nucleoporin Nup2p protein and is selected from the group consisting of FSFGTSQPNNTPS (SEQ ID NO:99), FSFSIPSKNTPDASKPS (SEQ ID NO:100), FVFGQAAAKPSLEKSS (SEQ ID NO:101), FSFGVPNSSKNETSKPV (SEQ ID NO:102), FTFGTKHAADSQNNKPS (SEQ ID NO:103), FTFGSSSALADNKEDVKKP (SEQ ID NO:104), FSFGINT-NTTKTADTKAPT (SEQ ID NO:105), FSFGKTTANLPANSSTSPAPSIPSTG (SEQ ID NO:106), FSFGPKKENRKKDESDSENDIEIKGPE (SEQ ID NO:107), FKFSGTVSSDVFKLNPSTDKNEKKTETNAKP (SEQ ID NO:108), FKFSLPFEQKGSQTTTNDSKEESTTEATGNESQ (SEQ ID NO:109), FTFGSTTIEKKNDENSTSNSKPEKSSDSNDSNPS (SEQ ID NO:110), FSFGISNGSESKDSDKPSLPSAVDGENDKKEATKPA (SEQ ID NO:111), FSFSSATSTTEQTKSKNPLSLTEATKTNVDNNSKAEAS (SEQ ID NO:112) and FSFGAATPSAKEASQEDDNNNVEKPSSKPAFNLIS-NAGTEKEKESKKDSKPA (SEQ ID NO:113).

In yet another related embodiment, the EBD sequence of a fusion polypeptide of the invention comprises at least 2-100 repeats of a Nup2p sequence set forth above, or a combination thereof.

According to another particular embodiment of the present invention, an EBD sequence is a sequence derived from a mammalian elastin protein. In another related embodiment, the EBD sequence of a fusion polypeptide of the invention is derived from a mouse elastin having the sequence set forth in SEQ ID NO: 21.

In a related embodiment, the EBD comprises a sequence derived from an elastin protein and is selected from the group consisting of VPGA (SEQ ID NO:114), GAGGL (SEQ ID NO:115), GAGGG (SEQ ID NO:116), VPGVG (SEQ ID NO:117), VPGFGAGA (SEQ ID NO:118), VPGALPGA (SEQ ID NO:119), VPGFGAGAG (SEQ ID NO:120), VPAVPGAGG (SEQ ID NO:121), VPGGVGVGG (SEQ ID NO:122), VGAGGFPGYG (SEQ ID NO:123), VPGAVPGGLPGG (SEQ ID NO:124), VSPAAAAKAAKYGAA (SEQ ID NO:125), VPQVGAGIGAGGKPGK (SEQ ID NO:126), VPGGVGVGGIPGGVGVGG (SEQ ID NO:127), VPGGVGGIGGIGGLGVSTGAV (SEQ ID NO:128), VPGGAAGAAAAYKAAAKAGAGLGGVGG (SEQ ID NO:129), VSPAAAAKAAAKAAKYGARGGVGIPTYG (SEQ ID NO:130), KPPKPYGGALGALGYQGGGCFGKSCGRKRK (SEQ ID NO:131), VPGAGTPAAAAAAAAAKAAAKAGLGPGVGG (SEQ ID NO:132), VPGRVAGAAPPAAAAAAAKAAAKAAQYGLG (SEQ ID NO:133), VPGVGLPGVYPGGVLPGTGARFPGVGVLPG (SEQ ID NO:134), VPTGTGVKAKAPGGGGAFSGIPGVGPFGGQQPG (SEQ ID NO:135), VPGGVYYPGAGIGGLGGGGGALGPGGKPPKPGAG (SEQ ID NO:136), VGAGAGLGGASPAAAAAAAKAAKYGAG-GAGALGGL (SEQ ID NO:137), GLGGVLGARPFPGGGVAARPGFGLSPIYPGGGAGGLGVGG (SEQ ID NO:138), VPGSLAASKAAKYGAAGGLGGPGGLGG-PGGLGGPGGLGGAG (SEQ ID NO:139), VPGGPGVRLPGAGIPGVGGIPGVGGIPGVGGPGIGGPGIVGGPGA (SEQ ID NO:140), VLPGVGGGIPGGAGAIPGIGGIA-GAGTPAAAAAAKAAAKAAKYGAAGGL (SEQ ID NO:141), VPGGVGPGGVTGIGAGPGGLGGAGSPAAAKSAAKAAAKAQYRAAAGLGAG (SEQ ID NO:142), and VPLGYPIKAPKLPGGYGLPYTNGKLPYGVAGAGGKAGYPTGTGVGSQAAAAAAK AAKYGAGGAG (SEQ ID NO:143).

In yet another related embodiment, the EBD sequence of a fusion polypeptide of the invention comprises at least 2-100 repeats of an elastin sequence set forth above, or a combination thereof.

In another embodiment, the EBD sequence of a fusion polypeptide of the invention comprises a combination of any one or more of the EBD sequences set forth herein.

In yet another embodiment of the invention, an EBD sequence of a fusion polypeptide of the invention comprises a combination of NF-H and NF-M sequences set forth herein.

In yet another embodiment of the invention, an EBD sequence of a fusion polypeptide of the invention comprises a combination of NF-H and Nup2p sequences set forth herein.

In yet another embodiment of the invention, an EBD sequence of a fusion polypeptide of the invention comprises a combination of NF-M and Nup2p sequence set forth herein.

In yet another embodiment of the invention, an EBD sequence of a fusion polypeptide of the invention comprises a combination of NF-H and filamentous phage fd adsorption protein pIII sequences set forth herein.

In yet another embodiment of the invention, an EBD sequence of a fusion polypeptide of the invention comprises a combination of NF-M and filamentous phage fd adsorption protein pIII sequences set forth herein.

In yet another embodiment of the invention, an EBD sequence of a fusion polypeptide of the invention comprises a combination of Nup2p and filamentous phage fd adsorption protein pIII sequences set forth herein.

In yet another embodiment of the invention, an EBD sequence of a fusion polypeptide of the invention comprises a combination of NF-H, NF-M and filamentous phage fd adsorption protein pIII sequences set forth herein.

In yet another embodiment of the invention, an EBD sequence of a fusion polypeptide of the invention comprises a combination of NF-H, NF-M and Nup2p sequences set forth herein.

In yet another embodiment of the invention, an EBD sequence of a fusion polypeptide of the invention comprises a combination of Nup2p, NF-M and filamentous phage fd adsorption protein pIII sequences set forth herein.

In yet another embodiment of the invention, an EBD sequence of a fusion polypeptide of the invention comprises a combination of NF-H, Nup2p and filamentous phage fd adsorption protein pIII sequences set forth herein.

In yet another embodiment of the invention, an EBD sequence of a fusion polypeptide of the invention comprises a combination of Nup2p, NF-H, NF-M and filamentous phage fd adsorption protein pIII sequences set forth herein.

According to another embodiment of the invention, an EBD sequence of a fusion polypeptide of the invention comprises a variant version of an amino acid sequence of NF-H described herein, where resulting sequence preserves amino acid composition of the parent sequence.

According to another embodiment of the invention, an EBD sequence of a fusion polypeptide of the invention comprises a variant version of an amino acid sequence of NF-M described herein, where resulting sequence preserves amino acid composition of the parent sequence.

According to another embodiment of the invention, an EBD sequence of a fusion polypeptide of the invention comprises a variant version of an amino acid sequence of Nup2p described herein, where resulting sequence preserves amino acid composition of the parent sequence.

According to another embodiment of the invention, an EBD sequence of a fusion polypeptide of the invention comprises a variant version of an amino acid sequence of filamentous phage fd adsorption protein pIII described herein, where resulting sequence preserves amino acid composition of the parent sequence.

According to another embodiment of the invention, an EBD sequence of a fusion polypeptide of the invention comprises a variant version of an amino acid sequence of elastin described herein, where resulting sequence preserves amino acid composition of the parent sequence.

According to another embodiment of the invention, an EBD sequence of a fusion polypeptide of the invention generally comprises between about 5-600 amino acid residues, between about 5-300 amino acid residues or between about 5-100 amino acid residues, however other polypeptide lengths may also be used.

In another embodiment, an EBD sequence of a fusion polypeptide of the invention is cleavable, e.g., can be removed and/or separated from the heterologous polypeptide sequence after recombinant expression by, for example, enzymatic or chemical cleavage methods.

In another embodiment, an EBD sequence of a fusion polypeptide of the invention is covalently linked at the N-terminus of the heterologous polypeptide sequence of interest. In another embodiment, an EBD sequence of a fusion polypeptide of the invention is covalently linked at the C-terminus of the heterologous polypeptide sequence of interest. In yet another embodiment, an EBD sequence of a fusion polypeptide of the invention is covalently linked at the N- and C-termini of the heterologous polypeptide sequence of interest.

In another embodiment of the invention, the charge of an EBD sequence of a fusion polypeptide of the invention is modulated by, for example, enzymatic and/or chemical methods, in order to modulate the activity of the EBD sequence. In a particular embodiment, the charge of the EBD sequence is modulated by phosphorylation.

According to another aspect of the invention, an isolated polynucleotide is provided, wherein the polynucleotide encodes a fusion polypeptide as described herein.

According to yet another aspect of the invention, there is provided an expression vector comprising an isolated polynucleotide encoding a fusion polypeptide as described herein. In a related embodiment, an expression vector is provided comprising a polynucleotide encoding an EBD sequence and further comprising a cloning site for insertion of a polynucleotide encoding a heterologous polypeptide of interest.

According to yet another aspect of the invention, there is provided a host cell comprising an expression vector as described herein.

According to yet another aspect of the invention, there is provided a kit comprising an isolated polynucleotide as described herein, an isolated polypeptide as described herein and/or an isolated host cell as described herein.

Yet another aspect of the invention provides a method for producing a recombinant protein comprising the steps of: introducing into a host cell an expression vector comprising a polynucleotide sequence encoding a fusion polypeptide, the fusion polypeptide comprising at least one entropic bristle domain sequence and at least one polypeptide sequence of interest; and expressing the fusion polypeptide in the host cell. In another embodiment, the method further comprises the step of isolating the fusion polypeptide from the host cell. In another related embodiment, the method further comprises the step of removing the entropic bristle domain sequence from the fusion polypeptide before or after isolating the fusion polypeptide from the host cell.

These and other aspects of the present invention will become apparent upon reference to the following detailed description. All references disclosed herein and in the enclosed Application Data Sheet are hereby incorporated by reference in their entirety as if each was incorporated individually.

BRIEF DESCRIPTION OF THE SEQUENCE IDENTIFIERS

SEQ ID NO: 1 is the amino acid sequence of a human NF-H protein, Swiss-Prot accession number P12036, having an illustrative EB-domain corresponding to residues 414-1026.

SEQ ID NO: 2 is a polynucleotide sequence encoding the amino acid sequence of SEQ ID NO: 1, GenBank accession number BC073969, having an illustrative EB-domain corresponding to residues 1242-3081.

SEQ ID NO: 3 is the amino acid sequence of a mouse NF-H protein, Swiss-Prot accession number P19246, having an illustrative EB domain corresponding to residues 409-1087.

SEQ ID NO: 4 is a polynucleotide sequence encoding the amino acid sequence of SEQ ID NO: 3, GenBank accession number M35131, having an illustrative EB-domain corresponding to residues 1227-3219.

SEQ ID NO: 5 is the amino acid sequence of a bovine NF-M protein, Swiss-Prot accession number O77788; having an illustrative EB domain corresponding to residues 412-925.

SEQ ID NO: 6 is a polynucleotide sequence encoding protein residues 116-925 of bovine NF-M, GenBank accession number AF091342, having an illustrative EB domain corresponding to residues 891-2433.

SEQ ID NO: 7 is the amino acid sequence of a chicken NF-M protein, Swiss-Prot accession number P16053, having an illustrative EB domain corresponding to residues 407-857.

SEQ ID NO: 8 is a polynucleotide sequence encoding the protein fragment 259-857 of chicken NF-M, GenBank accession number X05558, having an illustrative EB domain corresponding to residues 177-1530.

SEQ ID NO: 9 is the amino acid sequence of a human NF-M protein, Swiss-Prot accession number P07197, having an illustrative EB domain corresponding to residues 412-915.

SEQ ID NO: 10 is a polynucleotide sequence encoding the amino acid sequence of SEQ ID NO: 9, GenBank accession number Y00067, having an illustrative EB domain corresponding to residues 1236-2751.

SEQ ID NO: 11 is the amino acid sequence of a mouse NF-M protein, Swiss-Prot accession number P08553, having an illustrative EB domain corresponding to residues 411-848.

SEQ ID NO: 12 is a polynucleotide sequence encoding the amino acid sequence of SEQ ID NO: 11, GenBank accession number X05640, having an illustrative EB domain corresponding to residues 1233-2550.

SEQ ID NO: 13 is the amino acid sequence of a rat NF-M protein, Swiss-Prot accession number P12839, having an illustrative EB domain corresponding to residues 411-845.

SEQ ID NO: 14 is a polynucleotide sequence encoding the amino acid sequence of SEQ ID NO: 13, GenBank accession number Z12152, having an illustrative EB domain corresponding to residues 1233-2538.

SEQ ID NO: 15 is the amino acid sequence of a rabbit NF-M protein, Swiss-Prot accession number P54938, having an illustrative EB domain corresponding to residues 198-644.

SEQ ID NO: 16 is a polynucleotide sequence encoding the amino acid sequence of SEQ ID NO: 15, GenBank accession number Z47378, having an illustrative EB domain corresponding to residues 594-1938.

SEQ ID NO: 17 is the amino acid sequence of a phage fd pIII protein, Swiss-Prot accession number P69168, having illustrative EB-domains corresponding to residues 86-104 and 236-274.

SEQ ID NO: 18 is a polynucleotide sequence encoding the amino acid sequence of SEQ ID NO: 17, GenBank accession number V00604, having illustrative EB domains corresponding to residues 258-312 and 708-822.

SEQ ID NO: 19 is the amino acid sequence of a Yeast Nup2p protein, Swiss-Prot accession number P32499, having an illustrative EB-domain corresponding to residues 189-582.

SEQ ID NO: 20 is a polynucleotide sequence encoding the amino acid sequence of SEQ ID NO: 19, GenBank accession number X69964, having an illustrative EB domain corresponding to residues 567-1748.

SEQ ID NO: 21 is the amino acid sequence of a mouse elastin protein, Swiss-Prot accession number P54320, the entire sequence of which represents an illustrative EB domain.

SEQ ID NO: 22 is a polynucleotide sequence encoding the amino acid sequence of SEQ ID NO: 21, GenBank accession number U08210.

SEQ ID Nos: 23 to 144 represent further illustrative EBD sequences according to the present invention.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

As used herein, the terms "polypeptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-expression modifications of the polypeptide, for example, glycosylations, acetylations, phosphorylations and the like, as well as other modifications known in the art, both naturally occurring and non-naturally occurring. Polypeptides of the invention may be prepared using any of a variety of well known recombinant and/or synthetic techniques, illustrative examples of which are further discussed below.

As noted above, the present invention, in a general aspect, relates to isolated fusion polypeptides comprising at least one entropic bristle domain (EBD) sequence and at least one heterologous polypeptide sequence. By providing an EBD sequence which sweeps out the three-dimensional space surrounding a newly synthesized heterologous polypeptide, the EBD sequences of the invention effectively exclude other polypeptides and thereby minimize aggregation with other newly synthesized heterologous polypeptides during recombinant polypeptide production.

In addition, an EBD sequence of the invention can provide steric stabilization to recombinant polypeptides, a property that is relatively independent of concentration, and can thus minimize problems associated with high-level recombinant production of polypeptides and proteins (e.g., precipitation, toxicity and/or inclusion body formation). Thus, EBD fusion polypeptides described herein exhibit both steric effects (via the entropic bristle's motion) and electrostatic effects (via the bristle's highly charged sequence) to minimize interactions between recombinant polypeptides expressed as fusions according to the present invention. These characteristics allow EBD polypeptide sequences to more effectively solubilize recombinantly expressed polypeptides than, for example, other fusion partners which do not have a steric exclusion component that contributes to their activity.

Therefore, according to one embodiment of the invention, fusion polypeptides comprising an EBD sequence and a heterologous polypeptide are provided which exhibit improved solubility relative to the corresponding heterologous polypeptide in the absence of the EBD sequence. In one embodiment, for example, the fusion polypeptide has at least 5% increased solubility relative to the heterologous polypeptide sequence alone. In another related embodiment, the fusion polypeptide has at least 25% increased solubility relative to the heterologous polypeptide sequence. In yet another related embodiment, the fusion polypeptide has at least 50% increased solubility relative to the heterologous polypeptide sequence.

The extent of improved solubility provided by an EBD sequence described herein can be determined using any of a number of available approaches (see for example, Kapust, R. B. and D. S. Waugh, *Escherichia coli maltose-binding protein is uncommonly effective at promoting the solubility of polypeptides to which it is fused*. Protein Sci, 1999. 8:1668-74; Fox, J. D., et al., *Maltodextrin-binding proteins from diverse bacteria and archaea are potent solubility enhancers*. FEBS Lett, 2003. 537:53-7; Dyson M R, Shadbolt S P, Vincent K J, Perera R L, McCafferty J. Production of soluble mammalian proteins in *Escherichia coli*: identification of protein features that correlate with successful expression. BMC Biotechnol. 2004 Dec. 14; 4(1):32).

Cells from single, drug resistant colony of *E. coli* overproducing the fusion polypeptide are grown to saturation in LB broth (Miller J H. 1972. *Experiments in molecular genetics*. Cold Spring Harbor, N.Y.: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and a soluble protein sample is collected from the supernatant after the insoluble debris is pelleted by centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli*. Coomassie-stained gels will be scanned with a gel-scanning densitometer and the pixel densities of the bands corresponding to the fusion proteins are obtained directly by volumetric integration. In each lane, the collective density of all *E. coli* proteins that are larger than the largest fusion protein are also determined by volumetric integration and used to normalize the values in each lane relative to the others. The percent solubility of each fusion protein is calculated by dividing the amount of soluble fusion protein by the total amount of fusion protein in the cells, after first subtracting the normalized background values obtained from negative control lanes (cells containing no expression vector). Descriptive statistical data (e.g., the mean and standard deviation) is then generated using standard methods.

The presence of an EBD sequence in fusion polypeptides of the present invention can also serve to reduce the extent of aggregation of a heterologous polypeptide sequence. In one embodiment, for example, the fusion polypeptide exhibits at least 10% reduced aggregation relative to the heterologous polypeptide. In another embodiment, the fusion polypeptide has at least 25% reduced aggregation relative to the heterologous polypeptide.

The extent of reduced aggregation provided by the fusion polypeptides of the present invention can be determined using any of a number of available techniques (see for example, Kapust, R. B. and D. S. Waugh, *Escherichia coli maltose-binding protein is uncommonly effective at promoting the solubility of polypeptides to which it is fused*. Protein Sci, 1999. 8:1668-74; Fox, J. D., et al., *Maltodextrin-binding proteins from diverse bacteria and archaea are potent solubility enhancers*. FEBS Lett, 2003. 537:53-7).

Cells from single, drug resistant colony of *E. coli* overproducing the fusion polypeptide are grown to saturation in LB broth (Miller J H. 1972. *Experiments in molecular genetics*. Cold Spring Harbor, N.Y.: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and an insoluble protein sample is collected from the pellet after the centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli*. Coomassie-stained gels are scanned with a gel-scanning densitometer and the pixel densities of the bands corresponding to the fusion proteins are obtained directly by volumetric integration. In each lane, the collective density of all insoluble *E. coli* proteins that are larger than the largest fusion protein is also determined by volumetric integration and used to normalize the values in each lane relative to the others. The percent insolubility of each fusion protein is calculated by dividing the amount of insoluble fusion protein by the total amount of fusion protein in the cells, after first subtracting the normalized background values obtained from negative control lanes (cells containing no expression vector). Descriptive statistical data (e.g., the mean and standard deviation) is generated by standard methods.

The presence of an EBD sequence in the fusion polypeptides of the present invention can also serve to improve the folding characteristics of the fusion polypeptides relative to the corresponding heterologous polypeptide, e.g., by minimizing interference caused by interaction with other proteins.

Assays for evaluating the folding characteristics of a fusion polypeptide of the invention can be carried out using conventional techniques, such as circular dichroism spectroscopy in far ultra-violet region, circular dichroism in near ultra-violet region, nuclear magnetic resonance spectroscopy, infra-red spectroscopy, Raman spectroscopy, intrinsic fluorescence spectroscopy, extrinsic fluorescence spectroscopy, fluorescence resonance energy transfer, fluorescence anisotropy and polarization, steady-state fluorescence, time-domain fluorescence, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD comprises an amino acid sequence that maintains a substantially random coil conformation. Whether a given amino acid sequence maintains a substantially random coil conformation can be determined by circular dichroism spectroscopy in far ultra-violet region, nuclear magnetic resonance spectroscopy, infra-red spectroscopy, Raman spectroscopy, fluorescence spectroscopy, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD sequence comprises an amino acid sequence that is substantially mutually repulsive. This property of being mutually repulsive can be determined by simple calculations of charge distribution within the polypeptide sequence.

In yet another embodiment of the invention, an EBD sequence comprises an amino acid sequence that remains in substantially constant motion, particularly in an aqueous environment. The property of being in substantially constant motion can be determined by nuclear magnetic resonance spectroscopy, small-angle X-ray scattering, small angle neutron scattering, dynamic light scattering, intrinsic fluorescence spectroscopy, extrinsic fluorescence spectroscopy, fluorescence resonance energy transfer, fluorescence anisotropy and polarization, steady-state fluorescence, time-domain fluorescence.

According to a more particular embodiment of the present invention, an EBD sequence is derived from one of the three subunits that make up mammalian axon neurofilaments (including human, bovine, chicken, rabbit, mouse, and rat neurofilaments). Axon neurofilaments are major cytoskeletal components of the axonal cell. One of the functions of neurofilaments is to maintain the bore of the axon. Spacing between the filaments is maintained by the action of an entropic brush formed by entropic bristles carried by certain of the neurofilament subunits. The combination of the entropic bristles along the length of the fiber results in the formation of an entropic brush that functions to sterically exclude interfiber contact by thermally-driven motion, thereby maintaining the bore of the axon. Interfilament spacing is thought to be maintained by long-range interactions between the entropic brushes formed by the EBDs that project from the NF-M and NF-H monomers (Brown and Hoh, 1997).

Therefore, in another embodiment of the invention, an EBD sequence of the invention comprises a C-terminal entropic bristle sequence of an NF-M or NF-H neurofilament protein. For example, in one embodiment, an EBD sequence of the invention comprises at least one amino acid sequence, SPEAEK (SEQ ID NO:23), derived from the neurofilament triplet H protein. In a related embodiment, multiple repeats of the SPEAEK (SEQ ID NO:23) sequence are provided within the same isolated fusion polypeptide. In a more particular embodiment, about 1-10, 1-50 or 1-100 repeats of the sequence SPEAEK (SEQ ID NO:23) are provide in a polypeptide.

In another embodiment of the invention, an EBD sequence is a sequence derived from a phage protein. In a more particular embodiment, the EBD sequence comprises at least one sequence derived from the linker region of a filamentous phage, such as the filamentous phage fd. In a more particular embodiment, the EBD sequence comprises at least one sequence derived from the linker region derived from the filamentous phage fd adsorption protein pIII. In a more particular embodiment, the EBD sequence comprises at least one sequence derived from the 36 amino acid linker region derived from filamentous phage fd adsorption protein pIII. In a more particular embodiment, an EBD sequence of the invention comprises between about 1-10, 1-50 or 1-100 repeats of the amino acid sequence EGGGS (SEQ ID NO:93), derived from the linker region of a filamentous phage fd adsorption protein pIII.

In another embodiment of the invention, an EBD sequence is a sequence derived from nucleoporin. In eukaryotic cells, the translocation of biomolecules between the nucleus and cytosol occurs through nuclear pore complexes (NPCs), supramolecular protein structures embedded in the double lipid membrane of the nuclear envelope (Nakielny, S., and Dreyfuss, G. (1999) *Cell* 99, 677-690; Pemberton, L. F., Blobel, G., and Rosenblum, J. S. (1998) *Curr. Opin. Cell Biol.* 10, 392-399; Rout, M., and Aitchison, J. (2001) *J. Biol. Chem.* 276, 16593-16596). For example, the *Saccharomyces cerevisiae* NPC is a 60-MDa structure (Yang, Q., Rout, M. P., and Akey, C. W. (1998) *Mol. Cell* 1, 223-234) formed by 30 different nucleoporins present in multiple copies per NPC (Rout, M. P., Aitchison, J. D., Suprapto, A., Hjertaas, K., Zhao, Y., and Chait, B. T. (2000) *J. Cell Biol.* 148, 635-651). The yeast NPC contains a core ring structure with 8-fold symmetry measuring 95 nm in diameter and 35 nm in depth (Yang, Q., Rout, M. P., and Akey, C. W. (1998) *Mol. Cell* 1, 223-234). It is believed that nucleoporins form a barrier meshwork that excludes most macromolecules larger than a threshold size from entering the NPC (Rout, M., and Aitchison, J. (2001) *J. Biol. Chem.* 276, 16593-16596; Rout, M. P., Aitchison, J. D., Suprapto, A., Hjertaas, K., Zhao, Y., and Chait, B. T. (2000) *J. Cell Biol.* 148, 635-651; Denning D P, Uversky V, Patel S S, Fink A L, Rexach M (2002) The *Saccharomyces cerevisiae* nucleoporin Nup2p is a natively unfolded protein. J Biol. Chem. 277(36):33447-55).

Therefore, in another embodiment of the invention, an EBD sequence of the invention comprises a central fragment of yeast nucleoporin Nup2p, such as those described herein. For example, in one embodiment, an EBD sequence of the invention comprises at least one amino acid sequence, FSFGTSQPNNTPS (SEQ ID NO:99), derived from the yeast nucleoporin porin protein Nup2p. In a related embodiment, multiple repeats of the FSFGTSQPNNTPS (SEQ ID NO:99) sequence are provided within the same isolated fusion polypeptide. In a more particular embodiment, about 1-10, 1-50 or 1-100 repeats of the sequence FSFGTSQPNNTPS (SEQ ID NO:99) are provide in a polypeptide.

In another embodiment of the invention, an EBD sequence is a sequence derived from an elastin-like polypeptide (ELP). ELPs comprise multiple repeats of the elastin-derived pentamer VPGxG (SEQ ID NO:144) where x, the guest residue, is not proline. ELPs are disordered and highly solvated at normal temperatures. They undergo inverse transition at elevated temperatures (the $T_t$ of a particular ELP sequence). The conformation of ELPs transitions from extended to collapsed and is dependent on temperature and salt concentration. Purification of proteins using ELPs may be carried out using inverse transition cycling. The ELP is soluble at temperatures below its T. and insoluble at temperatures above its $T_t$. Using ELPs to purify protein may be accomplished by making a fusion construct that includes the target heterologous protein and a suitable ELP multimer, e.g., comprising about 5-100 residues.

As will be understood by those skilled in the art, the propensity of a polypeptide chain to maintain a substantially random coil and flexible conformation is encoded in its amino acid composition rather than in its amino acid sequence (Uversky V N, Gillespie J R, Fink A L (2000) Why are "natively unfolded" proteins unstructured under physiologic conditions? Proteins. 41(3):415-27). This means that polypeptides sharing similar amino acid compositions will be similarly unfolded. The function of EBDs to increase protein solubility is based at least in part on their random coil and flexible conformation. Therefore, in one preferred embodiment of the invention, an EBD sequence of the invention comprises a scrambled variant sequence of a mammalian NF-H protein. In another embodiment of the invention, an EBD sequence of the invention comprises a scrambled variant sequence of a mammalian NF-M protein. In yet another embodiment of the invention, an EBD sequence of the invention comprises a scrambled variant sequence of a Nup2 protein. In another embodiment of the invention, an EBD sequence of the invention comprises a scrambled variant sequence of a mammalian elastin protein. In yet another embodiment of the invention, an EBD sequence of the invention comprises a scrambled variant sequence of a filamentous phage fd adsorption protein pIII.

In another embodiment of the invention, an EBD sequence of the invention comprises a scrambled variant sequence corresponding to any combination of fragments derived from sequence of a mammalian NF-H protein. In yet another embodiment of the invention, an EBD sequence of the invention comprises a scrambled variant sequence corresponding to any combination of fragments derived from sequence of a mammalian NF-M protein. In another embodiment of the invention, an EBD sequence of the invention comprises a scrambled variant sequence corresponding to any combination of fragments derived from sequence of a Nup2p protein. In another embodiment of the invention, an EBD sequence of the invention comprises a scrambled variant sequence corresponding to any combination of fragments derived from sequence of an elastin protein. In yet another embodiment of the invention, an EBD sequence of the invention comprises a scrambled variant sequence corresponding to any combination of fragments derived from sequence of a filamentous phage fd adsorption protein pIII.

In another embodiment of the invention, an EBD sequence of the invention comprises a scrambled variant sequence corresponding to multiple repeats of any combination of fragments derived from sequence of a mammalian NF-H protein. In yet another embodiment of the invention, an EBD sequence of the invention comprises a scrambled variant sequence corresponding to multiple repeats of any combination of fragments derived from sequence of a mammalian NF-M protein. In one more embodiment of the invention, an EBD sequence of the invention comprises a scrambled variant sequence corresponding to multiple repeats of any combination of fragments derived from sequence of a Nup2p protein. In another embodiment of the invention, an EBD sequence of the invention comprises a scrambled variant sequence corresponding to multiple repeats of any combination of fragments derived from sequence of an elastin protein. In yet another embodiment of the invention, an EBD sequence of the invention comprises a scrambled variant sequence corresponding to multiple repeats of any combination of fragments derived from sequence of a filamentous phage fd adsorption protein pIII.

In another embodiment of the invention, an EBD sequence of the invention comprises a scrambled variant sequence corresponding to any pairwise or multiple combinations of fragments derived from sequence of a mammalian NF-H protein, a mammalian NF-M protein, a Nup2p protein, an elastin protein and a filamentous phage fd adsorption protein pIII.

In yet another embodiment of the invention, an EBD sequence of the invention comprises a scrambled variant sequence corresponding to multiple repeats of any pairwise or multiple combinations of fragments derived from sequence of a mammalian NF-H protein, a mammalian NF-M protein, a Nup2p protein, an elastin protein and a filamentous phage fd adsorption protein pIII.

In another embodiment, the fusion polypeptides of the invention further comprise independent cleavable linkers, which allow an EBD sequence, for example at either the N or C terminus, to be easily cleaved from a heterologous polypeptide sequence of interest. Such cleavable linkers are known and available in the art. This embodiment thus provides improved isolation and purification of a heterologous polypeptide sequence and facilitates downstream high-throughput processes.

The present invention also provides polypeptide fragments of an EBD polypeptide sequence described herein, wherein the fragment comprises at least about 5, 10, 15, 20, 25, 50, or 100 contiguous amino acids, or more, including all intermediate lengths, of an EBD polypeptide sequence set forth herein, or those encoded by a polynucleotide sequence set forth herein. In a preferred embodiment, an EBD fragment provides similar or improved activity relative to the activity of the EBD sequence from which it is derived (wherein the activity includes, for example, one or more of improved solubility, improved folding, reduced aggregation and/or improved yield, when in fusion with a heterologous polypeptide sequence of interest.

In another aspect, the present invention provides variants of an EBD polypeptide sequence described herein. EBD polypeptide variants will typically exhibit at least about 70%, 75%, 80%, 85%, 90%, 91%, 92%, 93%, 94%, 95%, 96%, 97%, 98%, or 99% or more identity (e.g., determined as described below), along its length, to an EBD polypeptide sequence set forth herein. Preferably the EBD variant provides similar or improved activity relative to the activity of the EBD sequence from which the variant was derived (wherein the activity includes one or more of improved solubility, improved folding, reduced aggregation and/or improved yield, when in fusion with a heterologous polypeptide sequence of interest.

An EBD polypeptide variant thus refers to a polypeptide that differs from an EBD polypeptide sequence disclosed herein in one or more substitutions, deletions, additions and/or insertions. Such variants may be naturally occurring or may be synthetically generated, for example, by modifying one or more of the EBD polypeptide sequences of the invention and evaluating their activity as described herein and/or using any of a number of techniques well known in the art.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the EBD polynucleotides and polypeptides of the present invention and still obtain a functional molecule that encodes a variant or derivative polypeptide with desirable activity. When it is desired to alter the amino acid sequence of an EBD polypeptide to create an equivalent or an improved EBD variant or EBD fragment, one skilled in the art can readily change one or more of the codons of the encoding DNA sequence, for example according to Table 1.

For example, certain amino acids may be substituted for other amino acids in a protein structure without appreciable loss of desired activity. It is thus contemplated that various changes may be made in the EBD polypeptide sequences of the invention, or corresponding DNA sequences which encode said EBD polypeptide sequences, without appreciable loss of their desired activity.

TABLE 1

| Amino Acids | | Codons | | | | | |
|---|---|---|---|---|---|---|---|
| Alanine | Ala | A GCA | GCC | GCG | GCU | | |
| Cysteine | Cys | C UGC | UGU | | | | |
| Aspartic acid | Asp | D GAC | GAU | | | | |
| Glutamic acid | Glu | E GAA | GAG | | | | |
| Phenylalanine | Phe | F UUC | UUU | | | | |
| Glycine | Gly | G GGA | GGC | GGG | GGU | | |
| Histidine | His | H CAC | CAU | | | | |
| Isoleucine | Ile | I AUA | AUC | AUU | | | |
| Lysine | Lys | K AAA | AAG | | | | |
| Leucine | Leu | L UUA | UUG | CUA | CUC | CUG | CUU |
| Methionine | Met | M AUG | | | | | |
| Asparagine | Asn | N AAC | AAU | | | | |
| Proline | Pro | P CCA | CCC | CCG | CCU | | |
| Glutamine | Gln | Q CAA | CAG | | | | |
| Arginine | Arg | R AGA | AGG | CGA | CGC | CGG | CGU |
| Serine | Ser | S AGC | AGU | UCA | UCC | UCG | UCU |
| Threonine | Thr | T ACA | ACC | ACG | ACU | | |
| Valine | Val | V GUA | GUC | GUG | GUU | | |
| Tryptophan | Trp | W UGG | | | | | |
| Tyrosine | Tyr | Y UAC | UAU | | | | |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn has potential bearing on the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Therefore, according to certain embodiments, amino acids within an EBD sequence of the invention may be substituted by other amino acids having a similar hydropathic index or score. Preferably, any such changes result in an EBD sequence with a similar level of activity as the unmodified EBD sequence. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Thus, an amino acid can be substituted for another having a similar hydrophilicity value and in many cases still retain a desired level of activity. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like.

In addition, any polynucleotide of the invention, such as a polynucleotide encoding an EBD polypeptide sequence, or a vector comprising a polynucleotide encoding an EBD polypeptide sequence, may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions within an EBD sequence of the invention may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

In an illustrative embodiment, a variant EBD polypeptide differs from the corresponding unmodified EBD sequence by substitution, deletion or addition of five percent of the original amino acids or fewer. Variants may also (or alternatively) be modified by, for example, the deletion or addition of amino acids that have minimal influence on the desired activity.

A polypeptide of the invention may further comprise a signal (or leader) sequence at the N-terminal end of the polypeptide, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

As noted above, the present invention provides EBD polypeptide variant sequences which share some degree of sequence identity with an EBD polypeptide specifically described herein, such as those having at least 40%, 50%, 60%, 70%, 80%, 90% or 95% identity with an EBD polypeptide sequence described herein. When comparing polypeptide sequences to evaluate their extent of shared sequence identity, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington D.C. Vol. 5, Suppl. 3, pp. 345-358; Hein J. (1990) *Unified Approach to Alignment and Phylogenes*, pp. 626-645 *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In another aspect of the invention, there is provided an isolated polynucleotide sequence encoding a fusion polypeptide, the fusion polypeptide comprising at least one entropic bristle domain sequence and at least one heterologous polypeptide sequence of interest. In a related aspect, the invention provides expression vectors comprising a polynucleotide encoding an EBD fusion polypeptide of the invention. In another related aspect, an expression vector of the invention comprises a polynucleotide encoding one or more EBD sequence and further comprises a multiple cloning site for the insertion of a polynucleotide encoding a heterologous polypeptide sequence of interest.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references).

The terms "DNA" and "polynucleotide" are used essentially interchangeably herein to refer to a DNA molecule that has been isolated free of total genomic DNA of a particular species. "Isolated", as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will also be recognized, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

In addition to the EBD polynucleotide sequences set forth herein, the present invention also provides EBD polynucleotide variants having substantial identity to an EBD polynucleotide sequence disclosed herein, for example those comprising at least 50% sequence identity, preferably at least, 55%, 60%, 65%, 70%, 75%, 80%, 85%, 90%, 95%, 96%, 97%, 98%, or 99% or higher, sequence identity compared to an EBD polynucleotide sequence of this invention using the methods described herein, (e.g., BLAST analysis using standard parameters, as described below). One skilled in this art will recognize that these values can be appropriately adjusted to determine corresponding identity of polypeptides encoded by two polynucleotide sequences by taking into account codon degeneracy, amino acid similarity, reading frame positioning and the like.

Typically, EBD polynucleotide variants will contain one or more substitutions, additions, deletions and/or insertions, preferably such that the activity (e.g., improved folding, reduced aggregation and/or improved yield, when in fusion with a heterologous sequence of interest) of the polypeptide encoded by the variant polynucleotide is not substantially diminished relative to the corresponding unmodified polynucleotide sequence.

In additional embodiments, the present invention provides polynucleotide fragments comprising or consisting of various lengths of contiguous stretches of sequence identical to or complementary to one or more of the EBD polynucleotide sequences disclosed herein. For example, polynucleotides are provided by this invention that comprise or consist of at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence. Preferably, an EBD polynucleotide fragment of the invention encodes a fusion polypeptide that retains one or more desired activities, e.g., improved folding, reduced aggregation and/or improved yield, when in fusion with a heterologous sequence of interest.

The EBD polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

It will be appreciated by those of ordinary skill in the art that, as a result of the degeneracy of the genetic code, there are many nucleotide sequences that will encode a polypeptide as described herein. Some of these polynucleotides bear minimal homology to the native polynucleotide sequence. Nonetheless, polynucleotides that vary due to differences in codon usage are specifically contemplated by the present invention. Further, different alleles of an EBD polynucleotide sequence provided herein are within the scope of the present invention. Alleles are endogenous sequences that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In another embodiment of the invention, a mutagenesis approach, such as site-specific mutagenesis, may be employed for the preparation of variants and/or derivatives of the EBD polynucleotides and polypeptides described herein. By this approach, for example, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the present invention contemplates the mutagenesis of the disclosed polynucleotide sequences to alter one or more activities/properties of the encoded polypeptide. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length may be employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention wherein one or more desired activities is improved or modified.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein may be used. Longer contiguous identical or complementary sequences, e.g., those of about 20, 30, 40, 50, 100, 200, 500, 1000 (including all intermediate lengths) and even up to full length sequences will also be of use in certain embodiments.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

As noted, the EBD fusion polynucleotides, polypeptides and vectors of the present invention are advantageous in the context of recombinant polypeptide production, particularly where it is desired to achieve, for example, improved solubility, improved yield, improved folding and/or reduced aggregation of a heterologous polypeptide to which an EBD polypeptide sequence has been operably fused. Therefore, another aspect of the invention provides methods for producing a recombinant protein, for example by introducing into a host cell an expression vector comprising a polynucleotide sequence encoding a fusion polypeptide as described herein, e.g., a fusion polypeptide comprising at least one EBD sequence and at least one heterologous polypeptide sequence of interest; and expressing the fusion polypeptide in the host cell. In a related embodiment, the method further comprises the step of isolating the fusion polypeptide from the host cell. In another embodiment, the method further comprises the step of removing an entropic bristle domain sequence from the fusion polypeptide before or after isolating the fusion polypeptide from the host cell.

For recombinant production of a fusion polypeptide of the invention, DNA sequences encoding the polypeptide components of a fusion polypeptide (e.g., one or more EBD sequences and a heterologous polypeptide sequence of interest) may be assembled using conventional methodologies. In one example, the components may be assembled separately and ligated into an appropriate expression vector. For example, the 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the activities of both component polypeptides.

A peptide linker sequence may be employed to separate an EBD polypeptide sequence from a heterologous polypeptide sequence by some defined distance, for example a distance sufficient to ensure that the advantages of the invention are achieved, e.g., advantages such as improved folding, reduced aggregation and/or improved yield. Such a peptide linker sequence may be incorporated into the fusion polypeptide using standard techniques well known in the art. Suitable peptide linker sequences may be chosen based, for example, on the factors such as: (1) their ability to adopt a flexible extended conformation; and (2) their inability to adopt a secondary structure that could interfere with the activity of the EBD sequence. Illustrative peptide linker sequences, for example, may contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length, for example.

The ligated DNA sequences of a fusion polynucleotide are operably linked to suitable transcriptional and/or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The EBD and heterologous polynucleotide sequences may comprise a sequence as described herein, or may comprise a sequence that has been modified to facilitate recombinant polypeptide production. As will be understood by those of skill in the art, it may be advantageous in some instances to produce polypeptide-encoding polynucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In a particular embodiment, a fusion polynucleotide is engineered to further comprise a cleavage site located between the EBD polypeptide-encoding sequence and the heterologous polypeptide sequence, so that the heterologous polypeptide may be cleaved and purified away from an EBD polypeptide sequence at any desired stage following expression of the fusion polypeptide. Illustratively, a fusion polynucleotide of the invention may be designed to include heparin, thrombin, or factor Xa protease cleavage sites.

In order to express a desired polypeptide, the nucleotide sequences encoding the polypeptide, or functional equivalents, may be inserted into appropriate expression vector, i.e., a vector which contains the necessary elements for the transcription and translation of an inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264: 5503-5509); and the like. Proteins made in such systems may be designed to include heparin, thrombin, or factor Xa protease cleavage sites so that the cloned polypeptide of interest can be released from the EBD moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.− or aprt.sup.− cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the polypeptide from cell culture. The polypeptide produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to polynucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. Further discussion of vectors which comprise fusion proteins can be found in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Polypeptide synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect, the present invention further provides binding agents, such as antibodies and antigen-binding fragments thereof, that specifically bind to an EBD sequence according to the present invention, or to a portion, variant or derivative thereof. Such binding agents may be used, for example, to detect the presence of a polypeptide comprising an EBD sequence, to facilitate purification of a polypeptide comprising an EBD sequence, and the like. An antibody, or antigen-binding fragment thereof, is said to "specifically bind" to a polypeptide if it reacts at a detectable level (within, for example, an ELISA assay) with the polypeptide, and does not react detectably with unrelated polypeptides under similar conditions.

Antibodies and other binding agents can be prepared using conventional methodologies. For example, monoclonal antibodies specific for a polypeptide of interest may be prepared using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349: 293-299; Lobuglio et al. (1989) *Proc. Nat. Acad. Sci. USA* 86:4220-4224; Shaw et al. (1987) *J Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al., (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

Yet another aspect of the invention provides kits comprising one or more compositions described herein, e.g., an isolated EBD polynucleotide, polypeptide, antibody, vector, host cell, etc. In a particular embodiment, the invention provides a kit containing an expression vector comprising a polynucleotide sequence encoding an EBD polypeptide sequence and a multiple cloning site for easily introducing into the vector a polynucleotide sequence encoding a heterologous polypeptide sequence of interest. In another embodiment, the expression vector further comprises an engineered cleavage site to facilitate separation of the an EBD polypeptide sequence from the heterologous polypeptide sequence of interest following recombinant production.

The following Examples are offered by way of illustration and not by way of limitation.

EXAMPLES

Example 1

Use of Neurofilament Triplet M Protein (NF-M) in an Entropic Bristle Domain Vector.

The heterogeneity in the charge distribution of the human NF-M protein sequence was determined (shown below). The observed heterogeneity of the sequence suggests that EBDs with different characteristics may result for different regions of the sequence. For example, a 422-600 fragment is predominantly negatively charged. This fragment could be used as a basis to design EBDs for negatively charged proteins. The charge distribution in the 601-916 fragment is very heterogeneous. It can be used as a basis to design EBDs both for positively- and negatively-charged proteins.

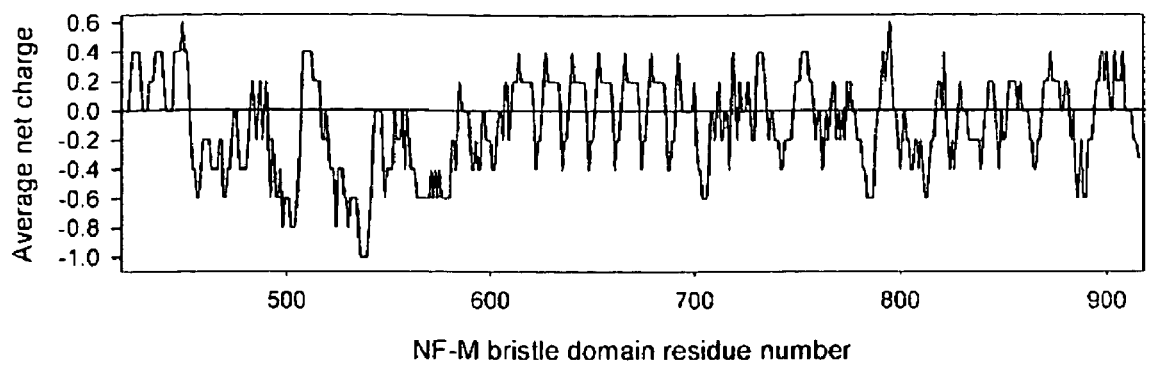
*Figure 1. Average net charge of a 5 residue moving window for residues 422 to 916 of human neurofilament medium (NF-M) protein sequence.*

Cloning of EBD sequence: We obtained the full-length cDNA for human NF-M from Origene Technologies (Rockville, Md.) and cloned the coding region for a 494-residue EBD sequence (residues 422 to 916 of the NF-M protein) into a pMALc2E vector from which the maltose-binding protein coding region had been deleted. Restriction sites suitable for cloning the test proteins were engineered at the appropriate locations. The proximity of the start codon in the cloned target sequences to the Shine Delgarno sequence of the vector was the same as that in pMALc2E. This construct is referred to as pEBDM.

Preparation of heterologous sequence: The coding region of a heterologous sequence of interest may be examined for rare E. coli codons and restrictions sites for a suitable cloning strategy. Prior to cloning, incompatible codons and restriction sites may be altered by site directed mutagenesis. The heterologous protein coding region, not including the stop codon, is PCR-amplified using primers containing the relevant restriction sites for the 5' and the 3' ends of the test protein open reading frame respectively.

Assembly of EBD expression vector: The PCR-amplified open reading frame of the heterologous polypeptide sequence of interest is ligated into the pEBDM vector backbone following digestion with appropriate restriction enzymes. In addition to cloning the heterologous sequence into an EBD expression vector, the test proteins may be cloned, for example, into an MBP expression vector (e.g., pMAL™-c2E, which already contains a maltose-binding protein coding region) as well as a control vector. The pMAL™-c2E serves as a positive control. To construct the control vector backbone, a Kpnl site is added to pMAL™-c2E at base 1524 by site-directed mutagenesis of 4 bases. This allows excision of the MBP coding region (including the start codon) by Kpnl digestion and re-ligation.

Protein expression and solubility analysis are carried out essentially according to the procedures of Kapust and Waugh. Briefly, the construct is transformed into E. coli BL21/DE3 cells (Stratagene, LaJolla, Calif.). This cell line provides increased protein stability due to its deficiency in both the OmpT and Lon proteases. The transformed cells are grown at 37° C. with shaking in LB broth supplemented with the appropriate antibiotics, diluted 50 fold, and grown to an $OD_{600}$ of 0.6 before induction. Recombinant protein productions is induced by adding IPTG to a final concentration of 1 mM, grown for more 3 hours, and harvested by centrifugation. The pellets are resuspended in 0.1 volume of lysis buffer and sonicated to disrupt cells. A sample of this crude lysate is reserved and used for total protein analyses. After the crude lysate is cleared by centrifugation, a sample of the cleared lysate will be used for soluble protein analyses. These samples are run on SDS-PAGE gels using standard procedures and visualized by Coomassie staining. The non-degraded soluble recombinant protein is apparent as a heavy band of the appropriate size.

The stained gels are scanned using an Epson Perfection 3200 scanner (Epson, Long Beach, Calif.) and the density of the protein bands is quantified using Total Lab image analysis software (Nonlinear Dynamics, Newcastle upon Tyne, UK). The densities of the bands corresponding to the fusion protein are normalized by dividing by the combined density of all the E. coli proteins larger than the largest fusion protein. Percent solubility is calculated by dividing the normalized density of the fusion protein band in the cleared lysate (soluble protein) lane by the normalized density of the fusion protein band in the crude lysate (total protein) protein lane after subtracting the normalized background density obtained from lanes containing equivalent protein extracts from E. coli cells grown with an empty vector. Mean and standard deviation are calculated for at least three independent experiments.

What is claimed is:

1. An isolated fusion polypeptide comprising an entropic bristle domain (EBD) sequence as set forth in SEQ ID NO: 83 and at least one heterologous polypeptide sequence, wherein the fusion polypeptide has increased solubility relative to the heterologous polypeptide sequence, reduced aggregation relative to the heterologous polypeptide sequence and/or improved folding relative to the heterologous polypeptide sequence.

2. The polypeptide according to claim 1, wherein the polypeptide further comprises a cleavable linker.

3. An isolated polynucleotide encoding a fusion polypeptide, wherein the fusion polypeptide comprises an entropic bristle domain (EBD) sequence as set forth in SEQ ID NO: 83 and at least one heterologous polypeptide sequence, wherein the fusion polypeptide has increased solubility relative to the heterologous polypeptide sequence, reduced aggregation relative to the heterologous polypeptide sequence and/or improved folding relative to the heterologous polypeptide sequence.

4. An expression vector comprising an isolated polynucleotide according to claim 3.

5. A host cell comprising an expression vector according to claim 4.

6. A kit comprising an isolated polynucleotide according to claim 3.

7. A kit comprising an expression vector according to claim 4.

8. A kit comprising a host cell according to claim 5.

9. A method for producing a recombinant protein comprising the steps of:
   (a) introducing into a host cell a polynucleotide according to claim 3 or an expression vector according to claim 4; and
   (b) expressing in the host cell a fusion polypeptide comprising an EBD sequence and at least one heterologous polypeptide sequence.

* * * * *